(12) United States Patent
Dlugos, Jr. et al.

(10) Patent No.: US 8,337,389 B2
(45) Date of Patent: Dec. 25, 2012

(54) METHODS AND DEVICES FOR DIAGNOSING PERFORMANCE OF A GASTRIC RESTRICTION SYSTEM

(75) Inventors: Daniel F. Dlugos, Jr., Middletown, OH (US); Mark S. Ortiz, Milford, OH (US); Amy L. Marcotte, Mason, OH (US); Randal T. Byrum, South Lebanon, OH (US); David N. Plescia, Cincinnati, OH (US); Jason L. Harris, Mason, OH (US); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1010 days.

(21) Appl. No.: 12/020,880

(22) Filed: Jan. 28, 2008

(65) Prior Publication Data
US 2009/0192533 A1   Jul. 30, 2009

(51) Int. Cl.
*A61F 13/00* (2006.01)
*A61F 2/00* (2006.01)
*A61B 5/103* (2006.01)
*A61B 5/117* (2006.01)
(52) U.S. Cl. .......................... 600/37; 600/587
(58) Field of Classification Search .................. 600/587, 600/593, 29–32, 37; 128/897–899; 606/139–141, 606/157, 201–203, 213, 228, 151, 192; 604/27–28, 604/909
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |

(Continued)

FOREIGN PATENT DOCUMENTS

CA  1059035  7/1979

(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner* — Jeffrey G Hoekstra
*Assistant Examiner* — H. Q. Nguyen
(74) *Attorney, Agent, or Firm* — Nutter McClennen & Fish LLP

(57) ABSTRACT

Methods and devices are provided for diagnosing performance of a gastric restriction system. In general, the methods and devices can enable patients, health care providers, and others to use pressure data as a feedback mechanism to monitor efficacy of an implantable restriction device and to identify, train, and/or prescribe treatment plan options. Pressure data monitoring can be used locally and/or remotely to monitor a restriction in a patient and compare gathered pressure data with a typical pressure of the restriction. Based on the results of the comparison, possible problems related to the patient and the restriction can be identified and diagnosed with possible cause(s) and solution(s). Notice of any detected possible problems, causes, and/or solutions can be provided to a user.

27 Claims, 26 Drawing Sheets

U.S. PATENT DOCUMENTS

| | | |
|---|---|---|
| 236,373 A | 1/1881 | Spilman |
| 322,388 A | 7/1885 | Lord |
| 400,401 A | 3/1889 | Gutzkow |
| D23,637 S | 9/1894 | Casad |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Hughel et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |

| | | | | | | |
|---|---|---|---|---|---|---|
| 3,167,044 | A | 1/1965 | Henrickson | 3,463,338 A | 8/1969 | Schneider |
| 3,171,549 | A | 3/1965 | Orloff | 3,469,818 A | 9/1969 | Cowan |
| 3,172,700 | A | 3/1965 | Haas | 3,470,725 A | 10/1969 | Brown et al. |
| 3,173,269 | A | 3/1965 | Imbertson | 3,472,230 A | 10/1969 | Fogarty |
| 3,182,494 | A | 5/1965 | Beatty et al. | 3,478,344 A | 11/1969 | Schwitzgebel et al. |
| 3,187,181 | A | 6/1965 | Keller | 3,482,449 A | 12/1969 | Werner |
| 3,187,745 | A | 6/1965 | Baum et al. | 3,482,816 A | 12/1969 | Arnold |
| 3,190,388 | A | 6/1965 | Moser et al. | 3,487,959 A | 1/1970 | Pearne et al. |
| 3,205,547 | A | 9/1965 | Riekse | 3,491,842 A | 1/1970 | Delacour et al. |
| 3,208,255 | A | 9/1965 | Burk | 3,492,638 A | 1/1970 | Lane |
| 3,209,570 | A | 10/1965 | Hills | 3,502,829 A | 3/1970 | Reynolds |
| 3,221,468 | A | 12/1965 | Casey | 3,503,116 A | 3/1970 | Strack |
| 3,228,703 | A | 1/1966 | Wilson | 3,504,664 A | 4/1970 | Haddad |
| 3,229,684 | A | 1/1966 | Nagumo et al. | 3,505,808 A | 4/1970 | Eschle |
| 3,236,088 | A | 2/1966 | Moller | 3,509,754 A | 5/1970 | Massingill et al. |
| 3,238,624 | A | 3/1966 | McCabe | 3,512,517 A | 5/1970 | Kadish et al. |
| 3,240,510 | A | 3/1966 | Spouge | 3,514,919 A | 6/1970 | Ashton at al. |
| 3,245,642 | A | 4/1966 | Dicke | 3,516,220 A | 6/1970 | Buford at al. |
| 3,255,568 | A | 6/1966 | Martin et al. | 3,517,553 A | 6/1970 | Williams at al. |
| 3,260,091 | A | 7/1966 | Shaw, Jr. | 3,527,226 A | 9/1970 | Hakin at al. |
| 3,265,822 | A | 8/1966 | Moulten | 3,529,908 A | 9/1970 | Smith |
| 3,266,487 | A | 8/1966 | Watkins et al. | 3,530,449 A | 9/1970 | Anderson |
| 3,273,447 | A | 9/1966 | Frank | 3,533,403 A | 10/1970 | Woodson |
| 3,283,352 | A | 11/1966 | Hu | 3,534,728 A | 10/1970 | Barrows |
| 3,290,919 | A | 12/1966 | Malinak et al. | 3,534,872 A | 10/1970 | Roth et al. |
| 3,292,493 | A | 12/1966 | Franklin | 3,535,914 A | 10/1970 | Veith et al. |
| 3,292,888 | A | 12/1966 | Fischer | 3,539,009 A | 11/1970 | Kudlaty |
| 3,294,988 | A | 12/1966 | Packard | 3,543,744 A | 12/1970 | LePar |
| 3,299,603 | A | 1/1967 | Shaw | 3,545,275 A | 12/1970 | Harrison et al. |
| 3,299,882 | A | 1/1967 | Masino | 3,550,583 A | 12/1970 | Chiku |
| 3,301,514 | A | 1/1967 | Sugaya | 3,550,847 A | 12/1970 | Scott |
| 3,302,457 | A | 2/1967 | Mayes | 3,563,094 A | 2/1971 | Rieschel |
| 3,306,384 | A | 2/1967 | Ross | 3,563,245 A | 2/1971 | McLean et al. |
| 3,313,314 | A | 4/1967 | Burke et al. | 3,566,083 A | 2/1971 | McMillin |
| 3,316,935 | A | 5/1967 | Kaiser et al. | 3,566,875 A | 3/1971 | Stoehr |
| 3,320,750 | A | 5/1967 | Haise et al. | 3,568,367 A | 3/1971 | Myers |
| 3,321,035 | A | 5/1967 | Tarpley | 3,568,636 A | 3/1971 | Lockwood |
| 3,332,788 | A | 7/1967 | Barnby | 3,576,554 A | 4/1971 | Temps, Jr. et al. |
| 3,334,510 | A | 8/1967 | Hallesy | 3,580,082 A | 5/1971 | Strack |
| 3,339,401 | A | 9/1967 | Peters | 3,581,402 A | 6/1971 | London et al. |
| 3,340,868 | A | 9/1967 | Darling | 3,583,387 A | 6/1971 | Garner et al. |
| 3,347,162 | A | 10/1967 | Braznell | 3,587,204 A | 6/1971 | George |
| 3,350,944 | A | 11/1967 | De Michele | 3,590,809 A | 7/1971 | London |
| 3,353,364 | A | 11/1967 | Blanding et al. | 3,590,818 A | 7/1971 | Lemole |
| 3,353,481 | A | 11/1967 | Antonucci | 3,590,992 A | 7/1971 | Soderstrom et al. |
| 3,356,334 | A | 12/1967 | Scaramucci | 3,592,183 A | 7/1971 | Watkins et al. |
| 3,356,510 | A | 12/1967 | Barnby | 3,594,519 A | 7/1971 | Schmidlin |
| 3,357,218 | A | 12/1967 | Mitchell | 3,602,885 A | 8/1971 | Grajeda |
| 3,357,461 | A | 12/1967 | Friendship | 3,610,016 A | 10/1971 | Bultman |
| 3,359,741 | A | 12/1967 | Nelson | 3,610,851 A | 10/1971 | Krupski |
| 3,361,300 | A | 1/1968 | Kaplan | 3,611,811 A | 10/1971 | Lissau |
| 3,364,929 | A | 1/1968 | Ide et al. | 3,614,926 A | 10/1971 | Brechtel |
| 3,365,684 | A | 1/1968 | Stemke | 3,614,955 A | 10/1971 | Mirowski et al. |
| 3,378,456 | A | 4/1968 | Roberts | 3,619,742 A | 11/1971 | Rud, Jr. |
| 3,380,445 | A | 4/1968 | Frasier | 3,623,371 A | 11/1971 | Jullien-Davin |
| 3,380,649 | A | 4/1968 | Roberts | 3,624,854 A | 12/1971 | Strong |
| 3,385,022 | A | 5/1968 | Anderson | 3,630,242 A | 12/1971 | Schieser et al. |
| 3,389,355 | A | 6/1968 | Schroeder, Jr. | 3,631,847 A | 1/1972 | Hobbs, II |
| 3,393,612 | A | 7/1968 | Gorgens at al. | 3,633,881 A | 1/1972 | Yurdin |
| 3,396,561 | A | 8/1968 | Day | 3,635,061 A | 1/1972 | Rydell et al. |
| 3,399,667 | A | 9/1968 | Nishimoto et al. | 3,635,074 A | 1/1972 | Moos et al. |
| 3,400,734 | A | 9/1968 | Rosenberg | 3,638,496 A | 2/1972 | King |
| 3,403,237 | A | 9/1968 | Wysong | 3,644,883 A | 2/1972 | Borman et al. |
| 3,409,924 | A | 11/1968 | Slama | 3,648,687 A | 3/1972 | Ramsey, III |
| 3,411,347 | A | 11/1968 | Wirth at al. | 3,651,289 A | 3/1972 | Nagashima et al. |
| 3,417,476 | A | 12/1968 | Martens | 3,651,405 A | 3/1972 | Whitney et al. |
| 3,420,325 | A | 1/1969 | McAlister et al. | 3,653,671 A | 4/1972 | Shipes |
| 3,422,324 | A | 1/1969 | Webb | 3,659,615 A | 5/1972 | Enger |
| 3,426,165 | A | 2/1969 | Beaman | 3,677,685 A | 7/1972 | Aoki et al. |
| 3,438,391 | A | 4/1969 | Yocum | 3,686,958 A | 8/1972 | Porter et al. |
| 3,443,608 | A | 5/1969 | Copping et al. | 3,688,568 A | 9/1972 | Karper at al. |
| 3,445,335 | A | 5/1969 | Gluntz | 3,701,392 A | 10/1972 | Wirth et al. |
| 3,447,281 | A | 6/1969 | Bufford et al. | 3,702,677 A | 11/1972 | Heffington |
| 3,450,153 | A | 6/1969 | Hildebrandt et al. | 3,703,099 A | 11/1972 | Rouse et al. |
| 3,453,546 | A | 7/1969 | Fryer | 3,712,138 A | 1/1973 | Alinari et al. |
| 3,453,848 | A | 7/1969 | Williamson | 3,713,124 A | 1/1973 | Durland et al. |
| 3,456,134 | A | 7/1969 | Ko | 3,719,524 A | 3/1973 | Ripley et al. |
| 3,457,909 | A | 7/1969 | Laird | 3,721,412 A | 3/1973 | Kindorf |
| 3,460,557 | A | 8/1969 | Gallant | 3,723,247 A | 3/1973 | Leine at al. |

| | | | | | |
|---|---|---|---|---|---|
| 3,724,000 A | 4/1973 | Eakman | 3,893,451 A | 7/1975 | Durand et al. |
| 3,727,463 A | 4/1973 | Intraub | 3,895,681 A | 7/1975 | Griffin et al. |
| 3,727,616 A | 4/1973 | Lenzkes | 3,899,862 A | 8/1975 | Muys et al. |
| 3,730,174 A | 5/1973 | Madison | 3,904,234 A | 9/1975 | Hill et al. |
| 3,730,560 A | 5/1973 | Abildgaard et al. | 3,908,334 A | 9/1975 | Rychiger et al. |
| 3,731,679 A | 5/1973 | Wilhelmson et al. | 3,908,461 A | 9/1975 | Turpen |
| 3,731,681 A | 5/1973 | Blackshear et al. | 3,908,721 A | 9/1975 | McGahey et al. |
| 3,732,731 A | 5/1973 | Fussell, Jr. | 3,910,087 A | 10/1975 | Jones |
| 3,735,040 A | 5/1973 | Punt et al. | 3,912,168 A | 10/1975 | Mullins et al. |
| 3,736,930 A | 6/1973 | Georgi | 3,912,304 A | 10/1975 | Abildgaard et al. |
| 3,738,356 A | 6/1973 | Workman | 3,918,286 A | 11/1975 | Whitehead |
| 3,740,921 A | 6/1973 | Meyer et al. | 3,918,291 A | 11/1975 | Pauly et al. |
| 3,746,111 A | 7/1973 | Berthiaume et al. | 3,920,965 A | 11/1975 | Sohrwardy et al. |
| 3,748,678 A | 7/1973 | Ballou | 3,921,682 A | 11/1975 | McGahey et al. |
| 3,749,098 A | 7/1973 | De Bennetot et al. | 3,922,951 A | 12/1975 | Linsinger et al. |
| 3,749,422 A | 7/1973 | Abildgaard et al. | 3,923,060 A | 12/1975 | Ellinwood, Jr. |
| 3,749,423 A | 7/1973 | Abildgaard et al. | 3,924,635 A | 12/1975 | Hakim et al. |
| 3,750,194 A | 8/1973 | Summers | 3,928,980 A | 12/1975 | Ganzinotti et al. |
| 3,757,770 A | 9/1973 | Brayshaw et al. | 3,929,175 A | 12/1975 | Coone |
| 3,759,095 A | 9/1973 | Short, Jr. et al. | 3,930,682 A | 1/1976 | Booth |
| 3,760,638 A | 9/1973 | Lawson et al. | 3,930,852 A | 1/1976 | Tanaka et al. |
| 3,763,960 A | 10/1973 | John et al. | 3,936,028 A | 2/1976 | Norton et al. |
| 3,765,142 A | 10/1973 | Lindquist et al. | 3,940,122 A | 2/1976 | Janzen et al. |
| 3,765,494 A | 10/1973 | Kielman, Jr. | 3,940,630 A | 2/1976 | Bergonz |
| 3,769,156 A | 10/1973 | Brecy et al. | 3,942,299 A | 3/1976 | Bory et al. |
| 3,769,830 A | 11/1973 | Porter et al. | 3,942,382 A | 3/1976 | Hok et al. |
| 3,774,243 A | 11/1973 | Ng et al. | 3,942,516 A | 3/1976 | Glynn et al. |
| 3,776,333 A | 12/1973 | Mathauser | 3,942,536 A | 3/1976 | Mirowski et al. |
| 3,778,051 A | 12/1973 | Allen et al. | 3,943,915 A | 3/1976 | Severson |
| 3,780,578 A | 12/1973 | Sellman et al. | 3,945,704 A | 3/1976 | Kraus et al. |
| 3,781,902 A | 12/1973 | Shim et al. | 3,946,613 A | 3/1976 | Silver |
| 3,783,585 A | 1/1974 | Hoyland | 3,946,615 A | 3/1976 | Hluchan |
| 3,789,667 A | 2/1974 | Porter et al. | 3,946,724 A | 3/1976 | La Balme et al. |
| 3,796,095 A | 3/1974 | Fussell, Jr. | 3,948,141 A | 4/1976 | Shinjo et al. |
| 3,807,219 A | 4/1974 | Wallskog | 3,949,388 A | 4/1976 | Fuller |
| 3,811,429 A | 5/1974 | Fletcher et al. | 3,953,289 A | 4/1976 | Costes et al. |
| 3,815,722 A | 6/1974 | Sessoms | 3,954,271 A | 5/1976 | Tredway, Sr. |
| 3,818,765 A | 6/1974 | Eriksen et al. | 3,958,558 A | 5/1976 | Dunphy et al. |
| 3,820,400 A | 6/1974 | Russo | 3,961,425 A | 6/1976 | Swanson et al. |
| 3,820,795 A | 6/1974 | Taylor | 3,961,646 A | 6/1976 | Schon et al. |
| 3,823,610 A | 7/1974 | Fussell, Jr. | 3,962,895 A | 6/1976 | Rydell et al. |
| 3,825,065 A | 7/1974 | Lloyd et al. | 3,962,921 A | 6/1976 | Lips |
| 3,825,963 A | 7/1974 | Abildgaard et al. | 3,963,019 A | 6/1976 | Quandt |
| 3,825,964 A | 7/1974 | Groswith, III et al. | 3,964,485 A | 6/1976 | Neumeier |
| 3,828,672 A | 8/1974 | Gazzola et al. | 3,964,770 A | 6/1976 | Abildgaard et al. |
| 3,828,766 A | 8/1974 | Krasnow | 3,967,737 A | 7/1976 | Peralta et al. |
| 3,831,588 A | 8/1974 | Rindner | 3,968,473 A | 7/1976 | Patton et al. |
| 3,831,942 A | 8/1974 | Del Mar | 3,968,694 A | 7/1976 | Clark |
| 3,833,238 A | 9/1974 | Liard et al. | 3,972,320 A | 8/1976 | Kalman |
| 3,834,167 A | 9/1974 | Tabor | 3,973,753 A | 8/1976 | Wheeler |
| 3,834,739 A | 9/1974 | Abildgaard et al. | 3,973,858 A | 8/1976 | Poisson et al. |
| 3,835,523 A | 9/1974 | Stansfield et al. | 3,974,655 A | 8/1976 | Halpern et al. |
| 3,839,708 A | 10/1974 | Bredesen et al. | 3,974,865 A | 8/1976 | Fenton et al. |
| 3,842,483 A | 10/1974 | Cramer | 3,977,391 A | 8/1976 | Fleischmann |
| 3,842,668 A | 10/1974 | Lippke et al. | 3,980,871 A | 9/1976 | Lindstrom et al. |
| 3,845,664 A | 11/1974 | Perry, Jr. | 3,982,571 A | 9/1976 | Fenton et al. |
| 3,845,751 A | 11/1974 | Runstetler | 3,983,948 A | 10/1976 | Jeter |
| 3,845,757 A | 11/1974 | Weyer | 3,985,133 A | 10/1976 | Jenkins et al. |
| 3,847,434 A | 11/1974 | Weman et al. | 3,987,860 A | 10/1976 | Jabsen |
| 3,850,208 A | 11/1974 | Hamilton | 3,989,005 A | 11/1976 | Bowler, Jr. et al. |
| 3,853,117 A | 12/1974 | Murr | 3,991,749 A | 11/1976 | Zent |
| 3,854,469 A | 12/1974 | Giori et al. | 3,992,948 A | 11/1976 | D'Antonio et al. |
| 3,855,902 A | 12/1974 | Kirst et al. | 3,993,149 A | 11/1976 | Harvey |
| 3,857,399 A | 12/1974 | Zacouto et al. | 3,996,927 A | 12/1976 | Frank |
| 3,857,452 A | 12/1974 | Hartman | 3,996,962 A | 12/1976 | Sutherland |
| 3,857,745 A | 12/1974 | Grausch et al. | 4,003,141 A | 1/1977 | Le Roy |
| 3,858,581 A | 1/1975 | Kamen | 4,005,282 A | 1/1977 | Jennings |
| 3,863,622 A | 2/1975 | Buuck | 4,005,593 A | 2/1977 | Goldberg |
| 3,863,933 A | 2/1975 | Tredway | 4,006,735 A | 2/1977 | Hittman et al. |
| 3,867,950 A | 2/1975 | Fischell | 4,009,375 A | 2/1977 | White et al. |
| 3,868,008 A | 2/1975 | Brumbaugh | 4,009,591 A | 3/1977 | Hester |
| 3,868,679 A | 2/1975 | Arneson | 4,010,449 A | 3/1977 | Faggin et al. |
| 3,871,599 A | 3/1975 | Takada et al. | 4,014,319 A | 3/1977 | Favre et al. |
| 3,872,285 A | 3/1975 | Shum et al. | 4,014,321 A | 3/1977 | March |
| 3,874,388 A | 4/1975 | King et al. | 4,016,764 A | 4/1977 | Rice |
| 3,876,980 A | 4/1975 | Haemmig et al. | 4,017,329 A | 4/1977 | Larson |
| 3,878,908 A | 4/1975 | Andersson et al. | 4,018,134 A | 4/1977 | Linsinger et al. |
| 3,881,528 A | 5/1975 | Mackenzie | 4,022,190 A | 5/1977 | Meyer |
| 3,893,111 A | 7/1975 | Cotter | 4,024,864 A | 5/1977 | Davies et al. |

| | | | | | | |
|---|---|---|---|---|---|---|
| 4,025,912 A | 5/1977 | Rice | | 4,160,448 A | 7/1979 | Jackson |
| 4,026,276 A | 5/1977 | Chubbuck | | 4,160,971 A | 7/1979 | Jones et al. |
| 4,027,661 A | 6/1977 | Lyon et al. | | 4,166,469 A | 9/1979 | Littleford |
| 4,031,899 A | 6/1977 | Renirie et al. | | 4,167,304 A | 9/1979 | Gelbke |
| 4,036,775 A | 7/1977 | Trautvetter et al. | | 4,167,952 A | 9/1979 | Reinicke |
| 4,039,069 A | 8/1977 | Kwan et al. | | 4,168,567 A | 9/1979 | Leguy et al. |
| 4,041,954 A | 8/1977 | Ohara et al. | | 4,170,280 A | 10/1979 | Schwarz |
| 4,042,504 A | 8/1977 | Drori et al. | | 4,171,218 A | 10/1979 | Hoshino et al. |
| 4,045,345 A | 8/1977 | Drori et al. | | 4,183,124 A | 1/1980 | Hoffman |
| 4,047,851 A | 9/1977 | Bender | | 4,183,247 A | 1/1980 | Allen et al. |
| 4,048,494 A | 9/1977 | Liesting et al. | | 4,185,641 A | 1/1980 | Minior et al. |
| 4,048,879 A | 9/1977 | Cox | | 4,186,287 A | 1/1980 | Scott |
| 4,049,004 A | 9/1977 | Walters | | 4,186,749 A | 2/1980 | Fryer |
| 4,051,338 A | 9/1977 | Harris, III | | 4,186,751 A | 2/1980 | Fleischmann |
| 4,052,991 A | 10/1977 | Zacouto et al. | | 4,190,057 A | 2/1980 | Hill et al. |
| 4,055,074 A | 10/1977 | Thimons et al. | | 4,191,004 A | 3/1980 | Gmuer et al. |
| 4,055,175 A | 10/1977 | Clemens et al. | | 4,191,187 A | 3/1980 | Wright et al. |
| 4,056,854 A | 11/1977 | Boretos et al. | | 4,192,192 A | 3/1980 | Schnell |
| 4,058,007 A | 11/1977 | Exner et al. | | 4,193,397 A | 3/1980 | Tucker et al. |
| 4,062,351 A | 12/1977 | Hastwell et al. | | 4,204,547 A | 5/1980 | Allocca |
| 4,062,354 A | 12/1977 | Taylor et al. | | 4,206,755 A | 6/1980 | Klein et al. |
| 4,062,360 A | 12/1977 | Bentley | | 4,206,761 A | 6/1980 | Cosman |
| 4,063,439 A | 12/1977 | Besson et al. | | 4,206,762 A | 6/1980 | Cosman |
| 4,064,882 A | 12/1977 | Johnson et al. | | 4,207,903 A | 6/1980 | O'Neill |
| 4,070,239 A | 1/1978 | Bevilacqua | | 4,212,074 A | 7/1980 | Kuno et al. |
| 4,072,047 A | 2/1978 | Reismuller et al. | | 4,217,221 A | 8/1980 | Masso |
| 4,073,292 A | 2/1978 | Edelman | | 4,217,588 A | 8/1980 | Freeny, Jr. |
| 4,075,099 A | 2/1978 | Pelton et al. | | 4,220,189 A | 9/1980 | Marquez |
| 4,075,602 A | 2/1978 | Clothier | | 4,221,219 A | 9/1980 | Tucker |
| 4,077,072 A | 3/1978 | Dezura et al. | | 4,221,523 A | 9/1980 | Eberle |
| 4,077,394 A | 3/1978 | McCurdy | | 4,222,377 A | 9/1980 | Burton |
| 4,077,405 A | 3/1978 | Haerten et al. | | 4,223,837 A | 9/1980 | Gubbiotti et al. |
| 4,077,882 A | 3/1978 | Gangemi | | 4,226,124 A | 10/1980 | Kersten et al. |
| 4,078,620 A | 3/1978 | Westlake et al. | | 4,226,229 A | 10/1980 | Eckhart et al. |
| 4,080,653 A | 3/1978 | Barnes, Jr. et al. | | 4,227,533 A | 10/1980 | Godfrey |
| 4,084,752 A | 4/1978 | Hagiwara et al. | | 4,231,376 A | 11/1980 | Lyon et al. |
| 4,086,488 A | 4/1978 | Hill | | 4,232,682 A | 11/1980 | Veth |
| 4,087,568 A | 5/1978 | Fay et al. | | 4,237,900 A | 12/1980 | Schulman et al. |
| 4,088,417 A | 5/1978 | Kosmowski | | 4,241,247 A | 12/1980 | Byrne et al. |
| 4,089,329 A | 5/1978 | Couvillon, Jr. et al. | | 4,241,870 A | 12/1980 | Marcus |
| 4,090,802 A | 5/1978 | Bilz et al. | | 4,245,593 A | 1/1981 | Stein |
| 4,092,719 A | 5/1978 | Salmon et al. | | 4,246,877 A | 1/1981 | Kennedy |
| 4,092,925 A | 6/1978 | Fromson | | 4,247,850 A | 1/1981 | Marcus |
| 4,096,866 A | 6/1978 | Fischell | | 4,248,238 A | 2/1981 | Joseph et al. |
| 4,098,293 A | 7/1978 | Kramer et al. | | 4,248,241 A | 2/1981 | Tacchi |
| 4,103,496 A | 8/1978 | Colamussi et al. | | 4,256,094 A | 3/1981 | Kapp et al. |
| 4,106,370 A | 8/1978 | Kraus et al. | | 4,256,118 A | 3/1981 | Nagel et al. |
| 4,107,689 A | 8/1978 | Jellinek | | 4,262,343 A | 4/1981 | Claycomb |
| 4,107,995 A | 8/1978 | Ligman et al. | | 4,262,632 A | 4/1981 | Hanton et al. |
| 4,108,148 A | 8/1978 | Cannon, III | | 4,265,241 A | 5/1981 | Portner et al. |
| 4,108,575 A | 8/1978 | Schal et al. | | 4,265,252 A | 5/1981 | Chubbuck et al. |
| 4,109,148 A | 8/1978 | Jaulmes et al. | | 4,271,018 A | 6/1981 | Drori et al. |
| 4,109,518 A | 8/1978 | Dooley et al. | | 4,273,070 A | 6/1981 | Hoefelmayr et al. |
| 4,109,644 A | 8/1978 | Kojima | | 4,274,444 A | 6/1981 | Ruyak |
| 4,111,056 A | 9/1978 | Mastromatteo | | 4,275,600 A | 6/1981 | Turner et al. |
| 4,111,629 A | 9/1978 | Nussbaumer et al. | | 4,275,913 A | 6/1981 | Marcus |
| 4,114,424 A | 9/1978 | Johnson | | 4,278,540 A | 7/1981 | Drori et al. |
| 4,114,606 A | 9/1978 | Seylar | | 4,280,036 A | 7/1981 | Fukatsu et al. |
| 4,120,097 A | 10/1978 | Jeter | | 4,280,775 A | 7/1981 | Wood |
| 4,120,134 A | 10/1978 | Scholle | | 4,281,666 A | 8/1981 | Cosman |
| 4,121,635 A | 10/1978 | Hansel | | 4,281,667 A | 8/1981 | Cosman |
| 4,123,310 A | 10/1978 | Varon et al. | | 4,284,073 A | 8/1981 | Krause et al. |
| 4,124,023 A | 11/1978 | Fleischmann et al. | | 4,285,770 A | 8/1981 | Chi et al. |
| 4,127,110 A | 11/1978 | Bullara | | 4,291,699 A | 9/1981 | Geddes et al. |
| 4,130,169 A | 12/1978 | Denison | | 4,295,963 A | 10/1981 | Drori et al. |
| 4,131,596 A | 12/1978 | Allen | | 4,297,927 A | 11/1981 | Kuroda et al. |
| 4,133,355 A | 1/1979 | Mayer | | 4,303,075 A | 12/1981 | Heilman et al. |
| 4,133,367 A | 1/1979 | Abell | | 4,305,402 A | 12/1981 | Katims |
| 4,140,131 A | 2/1979 | Dutcher et al. | | 4,312,374 A | 1/1982 | Drori et al. |
| 4,141,348 A | 2/1979 | Hittman | | 4,314,480 A | 2/1982 | Becker |
| 4,141,349 A | 2/1979 | Ory et al. | | 4,316,693 A | 2/1982 | Baxter et al. |
| 4,143,661 A | 3/1979 | LaForge et al. | | 4,325,387 A | 4/1982 | Helfer |
| 4,146,029 A | 3/1979 | Ellinwood, Jr. | | 4,327,804 A | 5/1982 | Reed |
| 4,147,161 A | 4/1979 | Ikebe et al. | | 4,328,654 A | 5/1982 | Van Ginkel et al. |
| 4,148,096 A | 4/1979 | Haas et al. | | 4,332,254 A | 6/1982 | Lundquist |
| 4,149,423 A | 4/1979 | Frosch et al. | | 4,339,831 A | 7/1982 | Johnson |
| 4,151,823 A | 5/1979 | Grosse et al. | | 4,342,218 A | 8/1982 | Fox |
| 4,153,085 A | 5/1979 | Adams | | 4,342,308 A | 8/1982 | Trick |
| 4,156,422 A | 5/1979 | Hildebrandt et al. | | 4,346,604 A | 8/1982 | Snook et al. |

| | | | | | |
|---|---|---|---|---|---|
| 4,347,851 A | 9/1982 | Jundanian | 4,473,078 A | 9/1984 | Angel |
| 4,350,647 A | 9/1982 | de la Cruz | 4,476,721 A | 10/1984 | Hochreuther et al. |
| 4,350,970 A | 9/1982 | von Tomkewitsch et al. | 4,478,213 A | 10/1984 | Redding |
| 4,351,037 A | 9/1982 | Scherbatskoy | 4,478,538 A | 10/1984 | Kakino et al. |
| 4,351,116 A | 9/1982 | Scott, Jr. | 4,483,196 A | 11/1984 | Kurtz et al. |
| 4,356,486 A | 10/1982 | Mount | 4,484,135 A | 11/1984 | Ishihara et al. |
| 4,360,010 A | 11/1982 | Finney | 4,485,813 A | 12/1984 | Anderson et al. |
| 4,360,277 A | 11/1982 | Daniel et al. | 4,489,916 A | 12/1984 | Stevens |
| 4,361,153 A | 11/1982 | Slocum et al. | 4,492,632 A | 1/1985 | Mattson |
| 4,363,236 A | 12/1982 | Meyers | 4,494,411 A | 1/1985 | Koschke et al. |
| 4,364,276 A | 12/1982 | Shimazoe et al. | 4,494,950 A | 1/1985 | Fischell |
| 4,365,425 A | 12/1982 | Gotchel | 4,497,176 A | 2/1985 | Rubin et al. |
| 4,368,937 A | 1/1983 | Palombo et al. | 4,497,201 A | 2/1985 | Allen et al. |
| 4,369,013 A | 1/1983 | Abildgaard et al. | 4,499,394 A | 2/1985 | Koal |
| 4,373,527 A | 2/1983 | Fischell | 4,499,691 A | 2/1985 | Karazim et al. |
| 4,376,523 A | 3/1983 | Goyen et al. | 4,499,750 A | 2/1985 | Gerber et al. |
| 4,378,809 A | 4/1983 | Cosman | 4,503,678 A | 3/1985 | Wimbush et al. |
| 4,380,427 A | 4/1983 | Hehl et al. | 4,511,974 A | 4/1985 | Nakane et al. |
| 4,385,636 A | 5/1983 | Cosman | 4,513,295 A | 4/1985 | Jones et al. |
| 4,386,422 A | 5/1983 | Mumby et al. | 4,515,004 A | 5/1985 | Jaenson |
| 4,387,907 A | 6/1983 | Hiestand et al. | 4,515,750 A | 5/1985 | Pardini et al. |
| 4,392,368 A | 7/1983 | Folkesson et al. | 4,516,866 A | 5/1985 | Yamauchi et al. |
| 4,393,899 A | 7/1983 | Tsuji et al. | 4,518,637 A | 5/1985 | Takeda et al. |
| 4,393,951 A | 7/1983 | Horst-Rudolf et al. | 4,519,401 A | 5/1985 | Ko et al. |
| 4,395,232 A | 7/1983 | Koch | 4,520,443 A | 5/1985 | Yuki et al. |
| 4,395,258 A | 7/1983 | Wang et al. | 4,522,213 A | 6/1985 | Wallroth et al. |
| 4,395,916 A | 8/1983 | Martin | 4,527,568 A | 7/1985 | Rickards et al. |
| 4,398,983 A | 8/1983 | Suzuki et al. | 4,529,401 A | 7/1985 | Leslie et al. |
| 4,399,705 A | 8/1983 | Weiger et al. | 4,531,526 A | 7/1985 | Genest |
| 4,399,707 A | 8/1983 | Wamstad | 4,531,936 A | 7/1985 | Gordon |
| 4,399,809 A | 8/1983 | Baro et al. | 4,536,000 A | 8/1985 | Rohm et al. |
| 4,399,821 A | 8/1983 | Bowers | 4,537,005 A | 8/1985 | Hoyland et al. |
| 4,403,984 A | 9/1983 | Ash et al. | 4,537,129 A | 8/1985 | Heinemann et al. |
| 4,404,968 A | 9/1983 | Evans, Sr. | 4,538,616 A | 9/1985 | Rogoff |
| 4,404,974 A | 9/1983 | Titus | 4,540,404 A | 9/1985 | Wolvek |
| 4,405,318 A | 9/1983 | Whitney et al. | 4,542,461 A | 9/1985 | Eldridge et al. |
| 4,407,125 A | 10/1983 | Parsons et al. | 4,544,369 A | 10/1985 | Skakoon et al. |
| 4,407,271 A | 10/1983 | Schiff | 4,545,185 A | 10/1985 | Chikatani et al. |
| 4,407,296 A | 10/1983 | Anderson | 4,546,524 A | 10/1985 | Kreft |
| 4,407,326 A | 10/1983 | Wilhelm | 4,548,209 A | 10/1985 | Wielders et al. |
| 4,408,597 A | 10/1983 | Tenney, Jr. | 4,552,150 A | 11/1985 | Zacouto et al. |
| 4,408,615 A | 10/1983 | Grossman | 4,553,226 A | 11/1985 | Scherbatskoy |
| 4,415,071 A | 11/1983 | Butler et al. | 4,556,063 A | 12/1985 | Thompson et al. |
| 4,416,282 A | 11/1983 | Saulson et al. | 4,557,269 A | 12/1985 | Reynolds et al. |
| 4,418,899 A | 12/1983 | Zimmermann et al. | 4,557,332 A | 12/1985 | Denison et al. |
| 4,419,393 A | 12/1983 | Hanson et al. | 4,559,815 A | 12/1985 | Needham et al. |
| 4,421,505 A | 12/1983 | Schwartz | 4,560,979 A | 12/1985 | Rosskopf et al. |
| 4,424,720 A | 1/1984 | Bucchianeri | 4,561,442 A | 12/1985 | Vollmann et al. |
| 4,428,228 A | 1/1984 | Banzhaf et al. | 4,562,751 A | 1/1986 | Nason et al. |
| 4,428,365 A | 1/1984 | Hakky et al. | 4,563,175 A | 1/1986 | LaFond |
| 4,430,899 A | 2/1984 | Wessel et al. | 4,565,116 A | 1/1986 | Hehl et al. |
| 4,431,009 A | 2/1984 | Marino, Jr. et al. | 4,566,456 A | 1/1986 | Koning et al. |
| 4,431,365 A | 2/1984 | Sturtz, Jr. | 4,569,623 A | 2/1986 | Goldmann |
| 4,432,363 A | 2/1984 | Kakegawa et al. | 4,570,351 A | 2/1986 | Szanto et al. |
| 4,435,173 A | 3/1984 | Siposs et al. | 4,571,161 A | 2/1986 | Leblanc et al. |
| 4,439,186 A | 3/1984 | Kuhl et al. | 4,571,995 A | 2/1986 | Timme |
| 4,441,491 A | 4/1984 | Evans, Sr. | 4,573,835 A | 3/1986 | Eckardt et al. |
| 4,441,501 A | 4/1984 | Parent | 4,574,792 A | 3/1986 | Trick |
| 4,444,194 A | 4/1984 | Burcham | 4,576,181 A | 3/1986 | Wallace et al. |
| 4,444,498 A | 4/1984 | Heinemann | 4,576,183 A | 3/1986 | Plicchi et al. |
| 4,445,385 A | 5/1984 | Endo | 4,577,512 A | 3/1986 | Lowenheck et al. |
| 4,446,711 A | 5/1984 | Valente | 4,581,018 A | 4/1986 | Jassawalla et al. |
| 4,447,224 A | 5/1984 | DeCant, Jr. et al. | 4,581,915 A | 4/1986 | Haulsee et al. |
| 4,449,493 A | 5/1984 | Kopec et al. | 4,587,840 A | 5/1986 | Dobler et al. |
| 4,450,811 A | 5/1984 | Ichikawa et al. | 4,589,805 A | 5/1986 | Duffner et al. |
| 4,451,033 A | 5/1984 | Nestegard | 4,592,339 A | 6/1986 | Kuzmak et al. |
| 4,453,537 A | 6/1984 | Spitzer | 4,592,340 A | 6/1986 | Boyles |
| 4,453,578 A | 6/1984 | Wilder | 4,593,703 A | 6/1986 | Cosman |
| 4,460,835 A | 7/1984 | Masuoka et al. | 4,595,228 A | 6/1986 | Chu |
| 4,464,170 A | 8/1984 | Clemens et al. | 4,596,563 A | 6/1986 | Pande |
| 4,465,015 A | 8/1984 | Osta et al. | 4,599,943 A | 7/1986 | Kobler et al. |
| 4,465,474 A | 8/1984 | Mardorf et al. | 4,600,855 A | 7/1986 | Strachan et al. |
| 4,466,290 A | 8/1984 | Frick | 4,602,541 A | 7/1986 | Benzinger et al. |
| 4,468,172 A | 8/1984 | Dixon et al. | 4,604,089 A | 8/1986 | Santangelo et al. |
| 4,468,762 A | 8/1984 | Jurgens et al. | 4,605,354 A | 8/1986 | Daly |
| 4,469,365 A | 9/1984 | Marcus et al. | 4,606,419 A | 8/1986 | Perini |
| 4,471,182 A | 9/1984 | Wielgos et al. | 4,606,478 A | 8/1986 | Hack et al. |
| 4,471,786 A | 9/1984 | Inagaki et al. | 4,610,256 A | 9/1986 | Wallace |
| 4,473,067 A | 9/1984 | Schiff | 4,614,137 A | 9/1986 | Jones |

| | | | | | | |
|---|---|---|---|---|---|---|
| 4,617,016 | A | 10/1986 | Blomberg et al. | 4,777,953 A | 10/1988 | Ash et al. |
| 4,618,861 | A | 10/1986 | Gettens et al. | 4,779,626 A | 10/1988 | Peel et al. |
| 4,620,807 | A | 11/1986 | Polit | 4,781,192 A | 11/1988 | Demer |
| 4,621,331 | A | 11/1986 | Iwata et al. | 4,782,826 A | 11/1988 | Fogarty |
| 4,622,871 | A | 11/1986 | Van Sickle et al. | 4,783,106 A | 11/1988 | Nutter |
| 4,626,462 | A | 12/1986 | Kober et al. | 4,788,847 A | 12/1988 | Sterghos |
| 4,633,304 | A | 12/1986 | Nagasaki et al. | 4,791,318 A | 12/1988 | Lewis et al. |
| 4,633,878 | A | 1/1987 | Bombardieri et al. | 4,794,803 A | 1/1989 | Osterhout et al. |
| 4,635,182 | A | 1/1987 | Hintz | 4,796,641 A | 1/1989 | Mills et al. |
| 4,637,736 | A | 1/1987 | Andeen et al. | 4,798,211 A | 1/1989 | Goor et al. |
| 4,638,665 | A | 1/1987 | Benson et al. | 4,798,227 A | 1/1989 | Goodwin |
| 4,644,246 | A | 2/1987 | Knapen et al. | 4,799,491 A | 1/1989 | Eckerle |
| 4,646,553 | A | 3/1987 | Tufte et al. | 4,799,625 A | 1/1989 | Weaver, Jr. et al. |
| 4,648,363 | A | 3/1987 | Kronich | 4,802,488 A | 2/1989 | Eckerle |
| 4,648,406 | A | 3/1987 | Miller | 4,803,987 A | 2/1989 | Calfee et al. |
| 4,658,358 | A | 4/1987 | Leach et al. | 4,804,368 A | 2/1989 | Skakoon et al. |
| 4,658,760 | A | 4/1987 | Zebuhr | 4,807,321 A | 2/1989 | Grasselli et al. |
| 4,660,568 | A | 4/1987 | Cosman | 4,808,167 A | 2/1989 | Mann et al. |
| 4,665,511 | A | 5/1987 | Rodney et al. | 4,812,823 A | 3/1989 | Dickerson |
| 4,665,896 | A | 5/1987 | LaForge et al. | 4,819,656 A | 4/1989 | Spector |
| 4,669,484 | A | 6/1987 | Masters | 4,820,265 A | 4/1989 | DeSatnick et al. |
| 4,672,974 | A | 6/1987 | Lee | 4,820,953 A | 4/1989 | Saubolle et al. |
| 4,674,457 | A | 6/1987 | Berger et al. | 4,821,167 A | 4/1989 | Wiebe |
| 4,674,546 | A | 6/1987 | Fournier et al. | 4,821,723 A | 4/1989 | Baker, Jr. et al. |
| 4,678,408 | A | 7/1987 | Nason et al. | 4,823,779 A | 4/1989 | Daly et al. |
| 4,681,559 | A | 7/1987 | Hooven | 4,830,006 A | 5/1989 | Haluska et al. |
| 4,683,850 | A | 8/1987 | Bauder et al. | 4,832,034 A | 5/1989 | Pizziconi et al. |
| 4,685,463 | A | 8/1987 | Williams | 4,833,384 A | 5/1989 | Munro et al. |
| 4,685,469 | A | 8/1987 | Keller et al. | 4,834,731 A | 5/1989 | Nowak et al. |
| 4,685,903 | A | 8/1987 | Cable et al. | 4,838,857 A | 6/1989 | Strowe et al. |
| 4,686,987 | A | 8/1987 | Salo et al. | 4,840,068 A | 6/1989 | Mayhew, Jr. |
| 4,687,530 | A | 8/1987 | Berscheid et al. | 4,840,350 A | 6/1989 | Cook et al. |
| 4,689,979 | A | 9/1987 | Otsuka et al. | 4,844,002 A | 7/1989 | Yasui et al. |
| 4,691,694 | A | 9/1987 | Boyd et al. | 4,846,153 A | 7/1989 | Berci |
| 4,691,710 | A | 9/1987 | Dickens et al. | 4,846,191 A | 7/1989 | Brockway et al. |
| 4,693,253 | A | 9/1987 | Adams | 4,846,664 A | 7/1989 | Hehl et al. |
| 4,695,237 | A | 9/1987 | Inaba et al. | 4,854,328 A | 8/1989 | Pollack |
| 4,696,189 | A | 9/1987 | Hochreuther et al. | 4,863,470 A | 9/1989 | Carter |
| 4,697,574 | A | 10/1987 | Karcher et al. | 4,865,587 A | 9/1989 | Walling |
| 4,698,038 | A | 10/1987 | Key et al. | 4,867,160 A | 9/1989 | Schaldach et al. |
| 4,700,497 | A | 10/1987 | Sato et al. | 4,867,498 A | 9/1989 | Delphia et al. |
| 4,700,610 | A | 10/1987 | Bauer et al. | 4,867,618 A | 9/1989 | Brohammer |
| 4,701,143 | A | 10/1987 | Key et al. | 4,869,252 A | 9/1989 | Gilli |
| 4,703,756 | A | 11/1987 | Gough et al. | 4,870,258 A | 9/1989 | Mochizuki et al. |
| 4,705,507 | A | 11/1987 | Boyles | 4,871,351 A | 10/1989 | Feingold et al. |
| 4,706,948 | A | 11/1987 | Kroecher et al. | 4,872,483 A | 10/1989 | Shah |
| 4,712,562 | A | 12/1987 | Ohayon et al. | 4,872,869 A | 10/1989 | Johns |
| 4,718,425 | A | 1/1988 | Tanaka et al. | 4,873,677 A | 10/1989 | Sakamoto et al. |
| 4,722,348 | A | 2/1988 | Ligtenberg et al. | 4,875,483 A | 10/1989 | Vollmann et al. |
| 4,724,806 | A | 2/1988 | Hartwig et al. | 4,880,004 A | 11/1989 | Baker, Jr. et al. |
| 4,724,830 | A | 2/1988 | Fischell | 4,882,678 A | 11/1989 | Hollis et al. |
| 4,725,826 | A | 2/1988 | Hunter | 4,886,392 A | 12/1989 | Iio et al. |
| 4,728,479 | A | 3/1988 | Merkovsky | 4,895,151 A | 1/1990 | Grevis et al. |
| 4,729,517 | A | 3/1988 | Krokor et al. | 4,896,594 A | 1/1990 | Baur et al. |
| 4,730,188 | A | 3/1988 | Milheiser | 4,898,158 A | 2/1990 | Daly et al. |
| 4,730,420 | A | 3/1988 | Stratmann et al. | 4,898,578 A | 2/1990 | Rubalcaba, Jr. |
| 4,730,619 | A | 3/1988 | Koning et al. | 4,899,751 A | 2/1990 | Cohen |
| 4,731,058 | A | 3/1988 | Doan | 4,899,752 A | 2/1990 | Cohen |
| 4,735,205 | A | 4/1988 | Chachques et al. | 4,902,277 A | 2/1990 | Mathies et al. |
| 4,738,267 | A | 4/1988 | Lazorthes et al. | 4,903,701 A | 2/1990 | Moore et al. |
| 4,738,268 | A | 4/1988 | Kipnis | 4,909,678 A | 3/1990 | Kakimoto et al. |
| 4,741,345 | A | 5/1988 | Matthews et al. | 4,913,147 A | 4/1990 | Fahlstrom et al. |
| 4,741,732 | A | 5/1988 | Crankshaw et al. | 4,919,143 A | 4/1990 | Ayers |
| 4,743,129 | A | 5/1988 | Keryhuel et al. | 4,924,872 A | 5/1990 | Frank |
| 4,745,541 | A | 5/1988 | Vaniglia et al. | 4,926,903 A | 5/1990 | Kawai et al. |
| 4,746,830 | A | 5/1988 | Holland | 4,932,406 A | 6/1990 | Berkovits |
| 4,750,495 | A | 6/1988 | Moore et al. | 4,934,369 A | 6/1990 | Maxwell |
| 4,752,115 | A | 6/1988 | Murray, Jr. et al. | 4,936,304 A | 6/1990 | Kresh et al. |
| 4,752,658 | A | 6/1988 | Mack | 4,940,037 A | 7/1990 | Eckert et al. |
| 4,757,463 | A | 7/1988 | Ballou et al. | 4,941,718 A | 7/1990 | Alexander, III et al. |
| 4,759,386 | A | 7/1988 | Grouw, III | 4,942,004 A | 7/1990 | Catanzaro |
| 4,763,649 | A | 8/1988 | Merrick | 4,944,050 A | 7/1990 | Shames et al. |
| 4,765,001 | A | 8/1988 | Smith | 4,944,298 A | 7/1990 | Sholder |
| 4,767,406 | A | 8/1988 | Wadham et al. | 4,944,307 A | 7/1990 | Hon et al. |
| 4,769,001 | A | 9/1988 | Prince | 4,945,761 A | 8/1990 | Lessi et al. |
| 4,772,896 | A | 9/1988 | Nakatsu | 4,949,724 A | 8/1990 | Mahutte et al. |
| 4,773,401 | A | 9/1988 | Citak et al. | 4,952,205 A | 8/1990 | Mauerer et al. |
| 4,774,950 | A | 10/1988 | Cohen | 4,952,928 A | 8/1990 | Carroll et al. |
| 4,774,955 | A | 10/1988 | Jones | 4,953,563 A | 9/1990 | Kaiser et al. |

| | | | | | |
|---|---|---|---|---|---|
| 4,954,677 A | 9/1990 | Alberter et al. | 5,089,979 A | 2/1992 | McEachern et al. |
| 4,958,630 A | 9/1990 | Rosenbluth et al. | 5,095,309 A | 3/1992 | Troyk et al. |
| 4,958,645 A | 9/1990 | Cadell et al. | 5,096,271 A | 3/1992 | Portman |
| 4,960,424 A | 10/1990 | Grooters | 5,097,831 A | 3/1992 | Lekholm |
| 4,960,966 A | 10/1990 | Evans et al. | 5,098,384 A | 3/1992 | Abrams |
| 4,967,585 A | 11/1990 | Grimaldo | 5,103,832 A | 4/1992 | Jackson |
| 4,967,761 A | 11/1990 | Nathanielsz | 5,105,810 A | 4/1992 | Collins et al. |
| 4,970,823 A | 11/1990 | Chen et al. | 5,107,850 A | 4/1992 | Olive |
| 4,971,251 A | 11/1990 | Dobrick et al. | 5,112,344 A | 5/1992 | Petros et al. |
| 4,977,896 A | 12/1990 | Robinson et al. | 5,113,859 A | 5/1992 | Funke et al. |
| 4,978,335 A | 12/1990 | Arthur, III | 5,113,869 A | 5/1992 | Nappholz et al. |
| 4,978,338 A | 12/1990 | Melsky et al. | 5,115,676 A | 5/1992 | Lee |
| 4,979,730 A | 12/1990 | Holbrook et al. | 5,117,825 A | 6/1992 | Grevious |
| 4,980,671 A | 12/1990 | McCurdy | 5,121,777 A | 6/1992 | Leininger et al. |
| 4,981,141 A | 1/1991 | Segalowitz | 5,127,451 A | 7/1992 | Fink, Jr. et al. |
| 4,981,173 A | 1/1991 | Perkins et al. | 5,129,394 A | 7/1992 | Mehra |
| 4,981,426 A | 1/1991 | Aoki et al. | 5,129,806 A | 7/1992 | Hehl et al. |
| 4,987,897 A | 1/1991 | Funke et al. | 5,131,145 A | 7/1992 | Badoureaux et al. |
| 4,988,337 A | 1/1991 | Ito et al. | 5,131,388 A | 7/1992 | Pless et al. |
| 4,992,794 A | 2/1991 | Brouwers et al. | 5,133,358 A | 7/1992 | Gustafson et al. |
| 4,997,556 A | 3/1991 | Yano et al. | 5,135,488 A | 8/1992 | Foote et al. |
| 5,001,528 A | 3/1991 | Bahraman | 5,139,484 A | 8/1992 | Hazon et al. |
| 5,003,807 A | 4/1991 | Terrell et al. | 5,144,949 A | 9/1992 | Olson |
| 5,003,975 A | 4/1991 | Hafelfinger et al. | 5,148,580 A | 9/1992 | Dyckow et al. |
| 5,003,976 A | 4/1991 | Alt et al. | 5,148,695 A | 9/1992 | Ellis |
| 5,004,472 A | 4/1991 | Wallace | 5,152,770 A | 10/1992 | Bengmark et al. |
| 5,004,873 A | 4/1991 | Schnut | 5,152,776 A | 10/1992 | Pinchuk |
| 5,005,574 A | 4/1991 | Fearnot et al. | 5,154,170 A | 10/1992 | Bennett et al. |
| 5,005,586 A | 4/1991 | Lahr | 5,154,171 A | 10/1992 | Chirife et al. |
| 5,006,844 A | 4/1991 | Ohta et al. | 5,154,693 A | 10/1992 | East et al. |
| 5,007,401 A | 4/1991 | Grohn et al. | 5,156,972 A | 10/1992 | Issachar et al. |
| 5,007,430 A | 4/1991 | Dardik | 5,158,078 A | 10/1992 | Bennett et al. |
| 5,007,919 A | 4/1991 | Silva et al. | 5,163,429 A | 11/1992 | Cohen |
| 5,009,662 A | 4/1991 | Wallace et al. | 5,167,615 A | 12/1992 | East et al. |
| 5,010,893 A | 4/1991 | Sholder | 5,168,757 A | 12/1992 | Rabenau et al. |
| 5,012,286 A | 4/1991 | Kawano et al. | 5,168,982 A | 12/1992 | Hakanen et al. |
| 5,012,810 A | 5/1991 | Strand et al. | 5,171,299 A | 12/1992 | Heitzmann et al. |
| 5,013,292 A | 5/1991 | Lemay et al. | 5,173,873 A | 12/1992 | Wu et al. |
| 5,014,040 A | 5/1991 | Weaver et al. | 5,174,286 A | 12/1992 | Chirife et al. |
| 5,019,032 A | 5/1991 | Robertson | 5,174,291 A | 12/1992 | Schoonen et al. |
| 5,019,041 A | 5/1991 | Robinson et al. | 5,176,502 A | 1/1993 | Sanderson et al. |
| 5,020,845 A | 6/1991 | Falcoff et al. | 5,178,197 A | 1/1993 | Healy |
| 5,021,046 A | 6/1991 | Wallace | 5,181,423 A | 1/1993 | Philipps et al. |
| 5,022,395 A | 6/1991 | Russie | 5,181,517 A | 1/1993 | Hickey |
| 5,024,965 A | 6/1991 | Chang et al. | 5,184,132 A | 2/1993 | Baird |
| 5,026,180 A | 6/1991 | Tajima et al. | 5,184,614 A | 2/1993 | Collins et al. |
| 5,026,360 A | 6/1991 | Johnsen et al. | 5,184,619 A | 2/1993 | Austin |
| 5,028,918 A | 7/1991 | Giles et al. | 5,185,535 A | 2/1993 | Farb et al. |
| 5,032,822 A | 7/1991 | Sweet | 5,186,224 A | 2/1993 | Schirmacher et al. |
| 5,036,869 A | 8/1991 | Inahara et al. | 5,188,106 A | 2/1993 | Nappholz et al. |
| 5,038,800 A | 8/1991 | Oba et al. | 5,188,604 A | 2/1993 | Orth |
| 5,041,086 A | 8/1991 | Koenig et al. | 5,192,314 A | 3/1993 | Daskalakis |
| 5,041,826 A | 8/1991 | Milheiser | 5,195,362 A | 3/1993 | Eason |
| 5,042,503 A | 8/1991 | Torok et al. | 5,197,322 A | 3/1993 | Indravudh |
| 5,044,770 A | 9/1991 | Haghkar | 5,199,427 A | 4/1993 | Strickland |
| 5,046,661 A | 9/1991 | Kimura et al. | 5,199,428 A | 4/1993 | Obel et al. |
| 5,048,060 A | 9/1991 | Arai et al. | 5,201,753 A | 4/1993 | Lampropoulos et al. |
| 5,050,922 A | 9/1991 | Falcoff | 5,204,670 A | 4/1993 | Stinton |
| 5,052,910 A | 10/1991 | Hehl et al. | 5,207,429 A | 5/1993 | Walmsley et al. |
| 5,053,008 A | 10/1991 | Bajaj | 5,209,223 A | 5/1993 | McGorry et al. |
| 5,057,078 A | 10/1991 | Foote et al. | 5,209,732 A | 5/1993 | Lampropoulos et al. |
| 5,058,583 A | 10/1991 | Geddes et al. | 5,211,129 A | 5/1993 | Taylor et al. |
| 5,061,239 A | 10/1991 | Shiels | 5,211,161 A | 5/1993 | Stef et al. |
| 5,062,052 A | 10/1991 | Sparer et al. | 5,212,476 A | 5/1993 | Maloney |
| 5,062,053 A | 10/1991 | Shirai et al. | 5,213,331 A | 5/1993 | Avanzini |
| 5,062,559 A | 11/1991 | Falcoff | 5,215,523 A | 6/1993 | Williams et al. |
| 5,064,974 A | 11/1991 | Vigneau et al. | 5,218,343 A | 6/1993 | Stobbe et al. |
| 5,067,960 A | 11/1991 | Grandjean et al. | 5,218,957 A | 6/1993 | Strickland |
| 5,068,779 A | 11/1991 | Sullivan et al. | 5,226,429 A | 7/1993 | Kuzmak |
| 5,069,680 A | 12/1991 | Grandjean et al. | 5,226,604 A | 7/1993 | Seiffert et al. |
| 5,077,102 A | 12/1991 | Chong | 5,230,694 A | 7/1993 | Rosenblum |
| 5,077,870 A | 1/1992 | Melbye et al. | 5,233,985 A | 8/1993 | Hudrlik |
| 5,078,139 A | 1/1992 | Strand et al. | 5,235,326 A | 8/1993 | Beigel et al. |
| 5,082,006 A | 1/1992 | Jonasson et al. | 5,244,269 A | 9/1993 | Harriehausen et al. |
| 5,083,563 A | 1/1992 | Collins et al. | 5,244,461 A | 9/1993 | Derlien et al. |
| 5,084,699 A | 1/1992 | DeMichele | 5,246,008 A | 9/1993 | Mueller et al. |
| 5,085,224 A | 2/1992 | Galen et al. | 5,249,858 A | 10/1993 | Nusser |
| 5,085,258 A | 2/1992 | Fink, Jr. et al. | 5,250,020 A | 10/1993 | Bley |
| 5,089,673 A | 2/1992 | Strzodka et al. | 5,254,096 A | 10/1993 | Rondelet et al. |

| | | | | | |
|---|---|---|---|---|---|
| 5,256,157 A | 10/1993 | Samiotes et al. | 5,456,690 A | 10/1995 | Duong-Van |
| 5,263,244 A | 11/1993 | Centa et al. | 5,461,390 A | 10/1995 | Hoshen |
| 5,263,981 A | 11/1993 | Polyak et al. | 5,464,435 A | 11/1995 | Neumann |
| 5,267,940 A | 12/1993 | Moulder | 5,467,627 A | 11/1995 | Smith et al. |
| 5,267,942 A | 12/1993 | Saperston | 5,474,226 A | 12/1995 | Joseph |
| 5,269,891 A | 12/1993 | Colin et al. | 5,479,818 A | 1/1996 | Walter et al. |
| 5,271,395 A | 12/1993 | Wahlstrand et al. | 5,482,049 A | 1/1996 | Addiss et al. |
| 5,274,859 A | 1/1994 | Redman et al. | 5,487,760 A | 1/1996 | Villafana |
| 5,280,789 A | 1/1994 | Potts | 5,493,738 A | 2/1996 | Sanderson et al. |
| 5,282,839 A | 2/1994 | Roline et al. | 5,494,036 A | 2/1996 | Uber, III et al. |
| 5,282,840 A | 2/1994 | Hudrlik | 5,494,193 A | 2/1996 | Kirschner et al. |
| 5,291,894 A | 3/1994 | Nagy et al. | 5,504,474 A | 4/1996 | Libman et al. |
| 5,292,219 A | 3/1994 | Merin et al. | 5,505,916 A | 4/1996 | Berry, Jr. |
| 5,295,967 A | 3/1994 | Rondelet et al. | 5,507,412 A | 4/1996 | Ebert et al. |
| 5,298,022 A | 3/1994 | Bernardi et al. | 5,507,737 A | 4/1996 | Palmskog et al. |
| 5,298,884 A | 3/1994 | Gilmore et al. | 5,507,785 A | 4/1996 | Deno |
| 5,300,093 A | 4/1994 | Koestner et al. | 5,509,888 A | 4/1996 | Miller |
| 5,300,120 A | 4/1994 | Knapp et al. | 5,509,891 A | 4/1996 | DeRidder |
| 5,304,112 A | 4/1994 | Mrklas et al. | 5,513,945 A | 5/1996 | Hartmann et al. |
| 5,305,923 A | 4/1994 | Kirschner et al. | 5,514,103 A | 5/1996 | Srisathapat et al. |
| 5,312,443 A | 5/1994 | Adams et al. | 5,518,504 A | 5/1996 | Polyak |
| 5,312,452 A | 5/1994 | Salo | 5,520,606 A | 5/1996 | Schoolman et al. |
| 5,312,453 A | 5/1994 | Shelton et al. | 5,523,740 A | 6/1996 | Burgmann et al. |
| 5,313,953 A | 5/1994 | Yomtov et al. | 5,534,018 A | 7/1996 | Wahlstrand et al. |
| 5,314,451 A | 5/1994 | Mulier | 5,535,752 A | 7/1996 | Halperin et al. |
| 5,314,457 A | 5/1994 | Jeutter et al. | 5,538,005 A | 7/1996 | Harrison et al. |
| 5,324,315 A | 6/1994 | Grevious | 5,541,857 A | 7/1996 | Walter et al. |
| 5,325,834 A | 7/1994 | Ballheimer et al. | 5,545,140 A | 8/1996 | Conero et al. |
| 5,326,249 A | 7/1994 | Weissfloch et al. | 5,545,151 A | 8/1996 | O'Connor et al. |
| 5,328,460 A | 7/1994 | Lord et al. | 5,545,186 A | 8/1996 | Olson et al. |
| 5,330,511 A | 7/1994 | Boute et al. | 5,545,214 A | 8/1996 | Stevens |
| 5,337,750 A | 8/1994 | Walloch | 5,547,470 A | 8/1996 | Johnson et al. |
| 5,341,430 A | 8/1994 | Aulia et al. | 5,551,427 A | 9/1996 | Altman |
| 5,342,401 A | 8/1994 | Spano et al. | 5,551,439 A | 9/1996 | Hickey |
| 5,342,406 A | 8/1994 | Thompson | 5,554,185 A | 9/1996 | Block et al. |
| 5,344,388 A | 9/1994 | Maxwell et al. | 5,558,644 A | 9/1996 | Boyd et al. |
| 5,347,476 A | 9/1994 | McBean, Sr. | 5,564,434 A | 10/1996 | Halperin et al. |
| 5,348,210 A | 9/1994 | Linzell et al. | 5,575,770 A | 11/1996 | Melsky et al. |
| 5,348,536 A | 9/1994 | Young et al. | 5,584,803 A | 12/1996 | Stevens et al. |
| 5,350,413 A | 9/1994 | Miller et al. | 5,586,629 A | 12/1996 | Shoberg et al. |
| 5,352,180 A | 10/1994 | Candelon et al. | 5,593,430 A | 1/1997 | Renger |
| 5,353,622 A | 10/1994 | Theener | 5,594,665 A | 1/1997 | Walter et al. |
| 5,353,800 A | 10/1994 | Pohndorf et al. | 5,596,986 A | 1/1997 | Goldfarb |
| 5,354,200 A | 10/1994 | Klein et al. | 5,597,284 A | 1/1997 | Weltlich et al. |
| 5,354,316 A | 10/1994 | Keimel | 5,610,083 A | 3/1997 | Chan et al. |
| 5,354,319 A | 10/1994 | Wyborny et al. | 5,611,768 A | 3/1997 | Tutrone, Jr. |
| 5,360,407 A | 11/1994 | Leonard et al. | 5,612,497 A | 3/1997 | Walter et al. |
| 5,365,462 A | 11/1994 | McBean, Sr. | 5,615,671 A | 4/1997 | Schoonen et al. |
| 5,365,619 A | 11/1994 | Solomon | 5,619,991 A | 4/1997 | Sloane |
| 5,365,985 A | 11/1994 | Todd et al. | 5,625,946 A | 5/1997 | Wildeson et al. |
| 5,368,040 A | 11/1994 | Carney | 5,626,623 A | 5/1997 | Kieval et al. |
| 5,370,665 A | 12/1994 | Hudrlik | 5,626,630 A | 5/1997 | Markowitz et al. |
| 5,373,852 A | 12/1994 | Harrison et al. | 5,630,836 A | 5/1997 | Prem et al. |
| 5,375,073 A | 12/1994 | McBean | 5,634,255 A | 6/1997 | Bishop et al. |
| 5,377,128 A | 12/1994 | McBean | 5,637,083 A | 6/1997 | Bertrand et al. |
| 5,378,231 A | 1/1995 | Johnson et al. | 5,643,207 A | 7/1997 | Rise |
| 5,382,232 A | 1/1995 | Hague et al. | 5,645,116 A | 7/1997 | McDonald |
| 5,383,915 A | 1/1995 | Adams | 5,650,766 A | 7/1997 | Burgmann et al. |
| 5,388,578 A | 2/1995 | Yomtov et al. | 5,673,585 A | 10/1997 | Bishop et al. |
| 5,388,586 A | 2/1995 | Lee et al. | 5,676,690 A | 10/1997 | Noren et al. |
| 5,388,831 A | 2/1995 | Quadri et al. | 5,681,285 A | 10/1997 | Ford et al. |
| 5,394,909 A | 3/1995 | Mitchell et al. | 5,686,831 A | 11/1997 | Vandervalk et al. |
| 5,402,944 A | 4/1995 | Pape et al. | 5,687,734 A | 11/1997 | Dempsey et al. |
| 5,406,957 A | 4/1995 | Tansey | 5,693,076 A | 12/1997 | Kaemmerer |
| 5,409,009 A | 4/1995 | Olson | 5,702,368 A | 12/1997 | Stevens et al. |
| 5,411,031 A | 5/1995 | Yomtov | 5,702,427 A | 12/1997 | Ecker et al. |
| 5,411,551 A | 5/1995 | Winston et al. | 5,702,431 A | 12/1997 | Wang et al. |
| 5,411,552 A | 5/1995 | Andersen et al. | 5,704,352 A | 1/1998 | Tremblay et al. |
| 5,416,372 A | 5/1995 | Ljungstroem et al. | 5,715,786 A | 2/1998 | Seiberth et al. |
| 5,417,226 A | 5/1995 | Juma | 5,715,837 A | 2/1998 | Chen |
| 5,417,717 A | 5/1995 | Salo et al. | 5,720,436 A | 2/1998 | Buschor et al. |
| 5,425,362 A | 6/1995 | Siker et al. | 5,730,101 A | 3/1998 | Aupperle et al. |
| 5,431,171 A | 7/1995 | Harrison et al. | 5,732,710 A | 3/1998 | Rabinovich et al. |
| 5,431,694 A | 7/1995 | Snaper et al. | 5,733,313 A | 3/1998 | Barreras, Sr. et al. |
| 5,433,694 A | 7/1995 | Lim et al. | 5,738,652 A | 4/1998 | Boyd et al. |
| 5,437,605 A | 8/1995 | Helmy et al. | 5,742,233 A | 4/1998 | Hoffman et al. |
| 5,443,215 A | 8/1995 | Fackler | 5,743,267 A | 4/1998 | Nikolic et al. |
| 5,447,519 A | 9/1995 | Peterson | 5,749,369 A | 5/1998 | Rabinovich et al. |
| 5,449,368 A | 9/1995 | Kuzmak | 5,749,909 A | 5/1998 | Schroeppel et al. |

| | | | | | | |
|---|---|---|---|---|---|---|
| 5,755,687 | A | 5/1998 | Donlon | 6,240,318 B1 | 5/2001 | Phillips |
| 5,755,748 | A | 5/1998 | Borza et al. | 6,245,102 B1 | 6/2001 | Jayaraman |
| 5,765,568 | A | 6/1998 | Sweezer, Jr. et al. | 6,248,080 B1 | 6/2001 | Miesel et al. |
| 5,769,812 | A | 6/1998 | Stevens et al. | 6,251,093 B1 | 6/2001 | Valley et al. |
| 5,771,903 | A | 6/1998 | Jakobsson | 6,269,819 B1 | 8/2001 | Oz et al. |
| 5,782,774 | A | 7/1998 | Shmulewitz | 6,277,078 B1 | 8/2001 | Porat et al. |
| 5,787,520 | A | 8/1998 | Dunbar | 6,292,697 B1 | 9/2001 | Roberts |
| 5,791,344 | A | 8/1998 | Schulman et al. | 6,309,350 B1 | 10/2001 | VanTassel et al. |
| 5,792,094 | A | 8/1998 | Stevens et al. | 6,315,769 B1 | 11/2001 | Peer et al. |
| 5,792,179 | A | 8/1998 | Sideris | 6,319,208 B1 | 11/2001 | Abita et al. |
| 5,795,325 | A | 8/1998 | Valley et al. | 6,328,699 B1 | 12/2001 | Eigler et al. |
| 5,796,827 | A | 8/1998 | Coppersmith et al. | 6,338,735 B1 | 1/2002 | Stevens |
| 5,800,375 | A | 9/1998 | Sweezer et al. | 6,357,438 B1 | 3/2002 | Hansen |
| 5,807,265 | A | 9/1998 | Itoigawa et al. | 6,360,122 B1 | 3/2002 | Fischell et al. |
| 5,807,336 | A | 9/1998 | Russo et al. | 6,360,822 B1 | 3/2002 | Robertson et al. |
| 5,810,015 | A | 9/1998 | Flaherty | 6,366,817 B1 | 4/2002 | Kung |
| 5,810,757 | A | 9/1998 | Sweezer, Jr. et al. | 6,379,308 B1 | 4/2002 | Brockway et al. |
| 5,814,016 | A | 9/1998 | Valley et al. | 6,379,380 B1 | 4/2002 | Satz |
| 5,817,093 | A | 10/1998 | Williamson, IV et al. | 6,398,752 B1 | 6/2002 | Sweezer, Jr. et al. |
| 5,833,603 | A | 11/1998 | Kovacs et al. | 6,409,674 B1 | 6/2002 | Brockway et al. |
| 5,836,300 | A | 11/1998 | Mault | 6,423,031 B1 | 7/2002 | Donlon |
| 5,836,886 | A | 11/1998 | Itoigawa et al. | 6,430,444 B1 | 8/2002 | Borza et al. |
| 5,840,081 | A | 11/1998 | Andersen et al. | 6,431,175 B1 | 8/2002 | Penner et al. |
| 5,849,225 | A | 12/1998 | Ebina et al. | 6,432,040 B1 | 8/2002 | Meah |
| 5,855,597 | A | 1/1999 | Jayaraman et al. | 6,443,887 B1 | 9/2002 | Derus et al. |
| 5,855,601 | A | 1/1999 | Bessler et al. | 6,443,893 B1 | 9/2002 | Schnakenberg et al. |
| 5,860,938 | A | 1/1999 | Lafontaine et al. | 6,450,173 B1 | 9/2002 | Forsell et al. |
| 5,861,018 | A | 1/1999 | Feierbach | 6,450,946 B1 | 9/2002 | Forsell et al. |
| 5,863,366 | A | 1/1999 | Snow | 6,453,907 B1 | 9/2002 | Forsell et al. |
| 5,868,702 | A | 2/1999 | Stevens et al. | 6,454,698 B1 | 9/2002 | Forsell et al. |
| 5,873,837 | A | 2/1999 | Lieber et al. | 6,454,699 B1 | 9/2002 | Forsell et al. |
| 5,875,953 | A | 3/1999 | Shioya et al. | 6,454,700 B1 | 9/2002 | Forsell et al. |
| 5,879,499 | A | 3/1999 | Corvi | 6,454,701 B1 | 9/2002 | Forsell et al. |
| 5,881,919 | A | 3/1999 | Womac et al. | 6,461,292 B1 | 10/2002 | Forsell et al. |
| 5,885,238 | A | 3/1999 | Stevens et al. | 6,461,293 B1 | 10/2002 | Forsell et al. |
| 5,887,475 | A | 3/1999 | Muldner | 6,463,329 B1 | 10/2002 | Goedeke |
| 5,899,927 | A | 5/1999 | Ecker et al. | 6,463,935 B1 | 10/2002 | Forsell et al. |
| 5,916,179 | A | 6/1999 | Sharrock | 6,464,628 B1 | 10/2002 | Forsell et al. |
| 5,916,237 | A | 6/1999 | Schu | 6,470,212 B1 | 10/2002 | Weijand et al. |
| 5,935,078 | A | 8/1999 | Feierbach | 6,470,892 B1 | 10/2002 | Forsell et al. |
| 5,938,669 | A | 8/1999 | Klaiber et al. | 6,471,635 B1 | 10/2002 | Forsell et al. |
| 5,951,487 | A | 9/1999 | Brehmeier-Flick et al. | 6,475,136 B1 | 11/2002 | Forsell et al. |
| 5,957,861 | A | 9/1999 | Combs et al. | 6,475,170 B1 | 11/2002 | Doron et al. |
| 5,967,986 | A | 10/1999 | Cimochowski et al. | 6,482,145 B1 | 11/2002 | Forsell et al. |
| 5,971,934 | A | 10/1999 | Scherer et al. | 6,482,171 B1 | 11/2002 | Corvi et al. |
| 5,974,873 | A | 11/1999 | Nelson et al. | 6,482,177 B1 | 11/2002 | Leinders et al. |
| 5,978,985 | A | 11/1999 | Thurman | 6,486,588 B2 | 11/2002 | Doron et al. |
| 5,995,874 | A | 11/1999 | Borza et al. | 6,503,189 B1 | 1/2003 | Forsell et al. |
| 6,015,386 | A | 1/2000 | Kensey et al. | 6,504,286 B1 | 1/2003 | Porat et al. |
| 6,015,387 | A | 1/2000 | Schwartz et al. | 6,531,739 B2 | 3/2003 | Cable et al. |
| 6,019,729 | A | 2/2000 | Itoigawa et al. | 6,533,719 B2 | 3/2003 | Kuyava et al. |
| 6,024,704 | A | 2/2000 | Meador et al. | 6,533,733 B1 | 3/2003 | Ericson et al. |
| 6,030,413 | A | 2/2000 | Lazarus | 6,542,350 B1 | 4/2003 | Rogers |
| 6,033,366 | A | 3/2000 | Brockway et al. | 6,558,321 B1 | 5/2003 | Burd et al. |
| 6,035,461 | A | 3/2000 | Nguyen | 6,558,994 B2 | 5/2003 | Cha et al. |
| 6,053,873 | A | 4/2000 | Govari et al. | 6,573,563 B2 | 6/2003 | Lee et al. |
| 6,056,723 | A | 5/2000 | Donlon | 6,582,462 B1 | 6/2003 | Andersen et al. |
| 6,058,330 | A | 5/2000 | Borza et al. | 6,599,250 B2 | 7/2003 | Webb et al. |
| 6,059,757 | A | 5/2000 | Macoviak et al. | 6,605,112 B1 | 8/2003 | Moll et al. |
| 6,067,474 | A | 5/2000 | Schulman et al. | 6,629,534 B1 | 10/2003 | St. Goar et al. |
| 6,067,991 | A | 5/2000 | Forsell et al. | 6,640,137 B2 | 10/2003 | MacDonald |
| 6,076,016 | A | 6/2000 | Feierbach | 6,641,610 B2 | 11/2003 | Wolf et al. |
| 6,083,174 | A | 7/2000 | Brehmeier-Flick et al. | 6,645,143 B2 | 11/2003 | VanTassel et al. |
| 6,090,096 | A | 7/2000 | St. Goar et al. | 6,673,109 B2 | 1/2004 | Cox |
| 6,102,678 | A | 8/2000 | Peclat et al. | 6,678,561 B2 | 1/2004 | Forsell et al. |
| 6,102,856 | A | 8/2000 | Groff et al. | 6,682,480 B1 | 1/2004 | Habib et al. |
| 6,102,922 | A | 8/2000 | Jakobsson et al. | 6,682,503 B1 | 1/2004 | Fariss et al. |
| 6,106,477 | A | 8/2000 | Miesel et al. | 6,682,559 B2 | 1/2004 | Myers et al. |
| 6,106,551 | A | 8/2000 | Crossett et al. | 6,695,866 B1 | 2/2004 | Kuehn et al. |
| 6,110,145 | A | 8/2000 | Macoviak | 6,709,385 B2 | 3/2004 | Forsell et al. |
| 6,113,553 | A | 9/2000 | Chubbuck | 6,718,200 B2 | 4/2004 | Marmaropoulos et al. |
| 6,131,664 | A | 10/2000 | Sonnier | 6,719,787 B2 | 4/2004 | Cox |
| 6,135,945 | A | 10/2000 | Sultan | 6,719,788 B2 | 4/2004 | Cox |
| 6,159,156 | A | 12/2000 | Van Bockel et al. | 6,719,789 B2 | 4/2004 | Cox |
| 6,162,180 | A | 12/2000 | Miesel et al. | 6,731,976 B2 | 5/2004 | Penn et al. |
| 6,162,245 | A | 12/2000 | Jayaraman et al. | 6,733,525 B2 | 5/2004 | Yang et al. |
| 6,168,614 | B1 | 1/2001 | Andersen et al. | 6,736,846 B2 | 5/2004 | Cox |
| 6,234,745 | B1 | 5/2001 | Pugh et al. | 6,752,813 B2 | 6/2004 | Goldfarb et al. |
| 6,240,316 | B1 | 5/2001 | Richmond et al. | 6,796,942 B1 | 9/2004 | Kreiner et al. |

| | | | | | | |
|---|---|---|---|---|---|---|
| 6,822,343 B2 | 11/2004 | Estevez | | 2005/0102026 A1 | 5/2005 | Turner et al. |
| 6,851,628 B1 | 2/2005 | Garrison et al. | | 2005/0159789 A1 | 7/2005 | Brockway et al. |
| 6,855,115 B2 | 2/2005 | Fonseca et al. | | 2005/0165317 A1 | 7/2005 | Turner et al. |
| 6,889,772 B2 | 5/2005 | Buytaert et al. | | 2005/0182330 A1 | 8/2005 | Brockway et al. |
| 6,890,300 B2 | 5/2005 | Lloyd et al. | | 2005/0187482 A1 | 8/2005 | O'Brien et al. |
| 6,896,651 B2 | 5/2005 | Gross et al. | | 2005/0187488 A1 | 8/2005 | Wolf |
| 6,896,690 B1 | 5/2005 | Lambrecht et al. | | 2005/0192642 A1 | 9/2005 | Forsell |
| 6,913,600 B2 | 7/2005 | Valley et al. | | 2005/0240155 A1 | 10/2005 | Conlon |
| 6,915,165 B2 | 7/2005 | Forsell et al. | | 2005/0240156 A1 | 10/2005 | Conlon |
| 6,926,246 B2 | 8/2005 | Ginggen et al. | | 2005/0250979 A1 | 11/2005 | Coe |
| 6,929,653 B2 | 8/2005 | Strecter | | 2005/0267406 A1 | 12/2005 | Hassler |
| 6,932,792 B1 | 8/2005 | St. Goar et al. | | 2005/0267500 A1 | 12/2005 | Hassler et al. |
| 6,951,229 B2 | 10/2005 | Garrison et al. | | 2005/0272968 A1 | 12/2005 | Byrum et al. |
| 6,951,571 B1 | 10/2005 | Srivastava | | 2005/0277960 A1 | 12/2005 | Hassler et al. |
| 6,953,429 B2 | 10/2005 | Forsell et al. | | 2005/0277974 A1 | 12/2005 | Hassler et al. |
| 6,961,619 B2 | 11/2005 | Casey | | 2005/0288604 A1 | 12/2005 | Eigler et al. |
| 6,970,742 B2 | 11/2005 | Mann et al. | | 2005/0288720 A1 | 12/2005 | Ross et al. |
| 6,979,350 B2 | 12/2005 | Moll et al. | | 2005/0288721 A1 | 12/2005 | Girouard et al. |
| 6,985,078 B2 | 1/2006 | Suzuki et al. | | 2005/0288739 A1 | 12/2005 | Hassler et al. |
| 6,989,027 B2 | 1/2006 | Allen et al. | | 2005/0288740 A1 | 12/2005 | Hassler et al. |
| 7,011,095 B2 | 3/2006 | Wolf et al. | | 2005/0288741 A1 | 12/2005 | Hassler et al. |
| 7,011,624 B2 | 3/2006 | Forsell et al. | | 2005/0288742 A1 | 12/2005 | Giordano et al. |
| 7,017,583 B2 | 3/2006 | Forsell et al. | | 2006/0002035 A1 | 1/2006 | Gao et al. |
| 7,018,406 B2 | 3/2006 | Seguin et al. | | 2006/0010090 A1 | 1/2006 | Brockway et al. |
| 7,021,402 B2 | 4/2006 | Beato et al. | | 2006/0020224 A1 | 1/2006 | Geiger |
| 7,025,727 B2 | 4/2006 | Brockway et al. | | 2006/0020305 A1 | 1/2006 | Desai et al. |
| 7,044,920 B2 | 5/2006 | Letort et al. | | 2006/0035446 A1 | 2/2006 | Chang et al. |
| 7,060,080 B2 | 6/2006 | Bachmann et al. | | 2006/0047205 A1 | 3/2006 | Ludomirsky et al. |
| 7,081,683 B2 | 7/2006 | Ariav et al. | | 2006/0049714 A1 | 3/2006 | Liu et al. |
| 7,109,933 B2 | 9/2006 | Ito et al. | | 2006/0058627 A1 | 3/2006 | Flaherty et al. |
| 7,131,447 B2 | 11/2006 | Sterman et al. | | 2006/0064134 A1 | 3/2006 | Mazar et al. |
| 7,131,945 B2 | 11/2006 | Fink et al. | | 2006/0085051 A1 | 4/2006 | Fritsch |
| 7,134,580 B2 | 11/2006 | Garrison et al. | | 2006/0089571 A1 | 4/2006 | Gertner |
| 7,144,400 B2 | 12/2006 | Byrum et al. | | 2006/0094966 A1 | 5/2006 | Brockway et al. |
| 7,147,640 B2 | 12/2006 | Huebner et al. | | 2006/0100531 A1 | 5/2006 | Moser |
| 7,153,262 B2 | 12/2006 | Stivoric et al. | | 2006/0113187 A1 | 6/2006 | Deng et al. |
| 7,187,978 B2 | 3/2007 | Malek et al. | | 2006/0122285 A1 | 6/2006 | Falloon et al. |
| 7,225,032 B2 | 5/2007 | Schmeling et al. | | 2006/0122863 A1 | 6/2006 | Gottesman et al. |
| 7,257,438 B2 | 8/2007 | Kinast | | 2006/0142635 A1 | 6/2006 | Forsell |
| 7,285,090 B2 | 10/2007 | Stivoric et al. | | 2006/0149124 A1 | 7/2006 | Forsell |
| 2001/0011543 A1 | 8/2001 | Forsell | | 2006/0149324 A1 | 7/2006 | Mann et al. |
| 2001/0041823 A1 | 11/2001 | Snyder et al. | | 2006/0149327 A1 | 7/2006 | Hedberg et al. |
| 2002/0049394 A1 | 4/2002 | Roy et al. | | 2006/0157701 A1 | 7/2006 | Bauer et al. |
| 2002/0120200 A1 | 8/2002 | Brockway et al. | | 2006/0161186 A1 | 7/2006 | Hassler et al. |
| 2002/0138009 A1 | 9/2002 | Brockway et al. | | 2006/0173238 A1* | 8/2006 | Starkebaum .......... 600/37 |
| 2002/0177782 A1 | 11/2002 | Penner | | 2006/0178617 A1 | 8/2006 | Adams et al. |
| 2003/0009201 A1 | 1/2003 | Forsell | | 2006/0178695 A1 | 8/2006 | Decant et al. |
| 2003/0030893 A1 | 2/2003 | Cornelius et al. | | 2006/0183967 A1 | 8/2006 | Lechner |
| 2003/0032857 A1 | 2/2003 | Forsell | | 2006/0184206 A1 | 8/2006 | Baker et al. |
| 2003/0037591 A1 | 2/2003 | Ashton et al. | | 2006/0189887 A1 | 8/2006 | Hassler et al. |
| 2003/0045775 A1 | 3/2003 | Forsell | | 2006/0189888 A1 | 8/2006 | Hassler et al. |
| 2003/0066536 A1 | 4/2003 | Forsell | | 2006/0189889 A1 | 8/2006 | Gertner |
| 2003/0088148 A1 | 5/2003 | Forsell | | 2006/0199997 A1 | 9/2006 | Hassler et al. |
| 2003/0092962 A1 | 5/2003 | Forsell | | 2006/0211912 A1 | 9/2006 | Dlugos et al. |
| 2003/0093117 A1 | 5/2003 | Saadat | | 2006/0211913 A1 | 9/2006 | Dlugos et al. |
| 2003/0100929 A1 | 5/2003 | Forsell | | 2006/0211914 A1 | 9/2006 | Hassler et al. |
| 2003/0105385 A1 | 6/2003 | Forsell | | 2006/0217668 A1 | 9/2006 | Schulze et al. |
| 2003/0109771 A1 | 6/2003 | Forsell | | 2006/0217673 A1 | 9/2006 | Schulze et al. |
| 2003/0114729 A1 | 6/2003 | Forsell | | 2006/0235310 A1 | 10/2006 | O'Brien et al. |
| 2003/0125605 A1 | 7/2003 | Forsell | | 2006/0235439 A1 | 10/2006 | Molitor et al. |
| 2003/0125768 A1 | 7/2003 | Peter | | 2006/0235448 A1 | 10/2006 | Roslin et al. |
| 2003/0135089 A1 | 7/2003 | Forsell | | 2006/0244914 A1 | 11/2006 | Cech et al. |
| 2003/0135090 A1 | 7/2003 | Forsell | | 2006/0247682 A1 | 11/2006 | Gerber et al. |
| 2003/0136417 A1 | 7/2003 | Fonseca et al. | | 2006/0247719 A1 | 11/2006 | Maschino et al. |
| 2003/0144648 A1 | 7/2003 | Forsell | | 2006/0247721 A1 | 11/2006 | Maschino et al. |
| 2003/0163079 A1 | 8/2003 | Burnett | | 2006/0247722 A1 | 11/2006 | Maschino et al. |
| 2003/0216666 A1 | 11/2003 | Ericson et al. | | 2006/0247723 A1 | 11/2006 | Gerber et al. |
| 2004/0054352 A1 | 3/2004 | Adams et al. | | 2006/0247724 A1 | 11/2006 | Gerber et al. |
| 2004/0113790 A1 | 6/2004 | Hamel et al. | | 2006/0247725 A1 | 11/2006 | Gerber et al. |
| 2004/0133092 A1 | 7/2004 | Kain | | 2006/0252982 A1 | 11/2006 | Hassler et al. |
| 2004/0147969 A1 | 7/2004 | Mann et al. | | 2006/0293625 A1 | 12/2006 | Hunt et al. |
| 2004/0172087 A1 | 9/2004 | Forsell | | 2006/0293626 A1 | 12/2006 | Byrum et al. |
| 2004/0186396 A1 | 9/2004 | Roy et al. | | 2006/0293627 A1 | 12/2006 | Byrum et al. |
| 2004/0254537 A1 | 12/2004 | Conlon et al. | | 2007/0010790 A1 | 1/2007 | Byrum et al. |
| 2005/0015014 A1 | 1/2005 | Fonseca et al. | | 2007/0027356 A1 | 2/2007 | Ortiz |
| 2005/0025979 A1 | 2/2005 | Sandt et al. | | 2007/0027493 A1 | 2/2007 | Ben-Haim et al. |
| 2005/0027175 A1 | 2/2005 | Yang | | 2007/0067206 A1 | 3/2007 | Haggerty et al. |
| 2005/0038328 A1 | 2/2005 | Stoehrer et al. | | 2007/0070906 A1 | 3/2007 | Thakur |
| 2005/0061079 A1 | 3/2005 | Schulman | | 2007/0072452 A1 | 3/2007 | Inagaki et al. |

| | | | |
|---|---|---|---|
| 2007/0081304 A1 | 4/2007 | Takeguchi | |
| 2007/0156013 A1 | 7/2007 | Birk | |
| 2007/0161958 A1 | 7/2007 | Glenn | |
| 2007/0167672 A1 | 7/2007 | Dlugos et al. | |
| 2007/0173881 A1 | 7/2007 | Birk et al. | |
| 2007/0179583 A1 | 8/2007 | Goetzinger et al. | |
| 2007/0208313 A1 | 9/2007 | Conlon et al. | |
| 2007/0225781 A1 | 9/2007 | Saadat et al. | |
| 2008/0009680 A1 | 1/2008 | Hassler | |

FOREIGN PATENT DOCUMENTS

| | | | |
|---|---|---|---|
| CA | 1119469 | | 3/1982 |
| CA | 1275135 | | 10/1990 |
| CA | 1277885 | | 12/1990 |
| CA | 1317482 | | 5/1993 |
| CA | 2082015 | | 5/1993 |
| CA | 1327191 | | 2/1994 |
| CA | 2119101 | | 9/1994 |
| CA | 2305998 | | 4/1999 |
| CN | 1059035 | | 2/1992 |
| CN | 1119469 | | 3/1996 |
| CN | 1241003 | | 1/2000 |
| EA | 4581 | | 6/2004 |
| EP | 125387 | B1 | 11/1984 |
| EP | 417171 | | 3/1991 |
| EP | 508141 | | 10/1992 |
| EP | 568730 | | 11/1993 |
| EP | 605302 | | 7/1994 |
| EP | 660482 | | 6/1995 |
| EP | 714017 | | 5/1996 |
| EP | 769340 | | 4/1997 |
| EP | 846475 | | 6/1998 |
| EP | 848780 | | 6/1998 |
| EP | 876808 | | 11/1998 |
| EP | 888079 | | 1/1999 |
| EP | 914059 | | 5/1999 |
| EP | 0941712 | A1 | 9/1999 |
| EP | 981293 | | 3/2000 |
| EP | 997680 | | 5/2000 |
| EP | 1003021 | | 5/2000 |
| EP | 1022983 | | 8/2000 |
| EP | 1050265 | | 11/2000 |
| EP | 1 115329 | | 7/2001 |
| EP | 1119314 | | 8/2001 |
| EP | 1128871 | | 9/2001 |
| EP | 1202674 | | 5/2002 |
| EP | 1213991 | | 6/2002 |
| EP | 1253877 | | 11/2002 |
| EP | 1253879 | | 11/2002 |
| EP | 1253880 | | 11/2002 |
| EP | 1253881 | | 11/2002 |
| EP | 1253883 | | 11/2002 |
| EP | 1253888 | | 11/2002 |
| EP | 1255511 | | 11/2002 |
| EP | 1255513 | | 11/2002 |
| EP | 1255514 | | 11/2002 |
| EP | 1263355 | | 12/2002 |
| EP | 1263357 | | 12/2002 |
| EP | 1284691 | | 2/2003 |
| EP | 1374758 | | 1/2004 |
| EP | 1488735 | | 12/2004 |
| EP | 1500411 | | 1/2005 |
| EP | 1510306 | | 3/2005 |
| EP | 1518514 | | 3/2005 |
| EP | 1545303 | | 6/2005 |
| EP | 1547549 | | 6/2005 |
| EP | 1563814 | | 8/2005 |
| EP | 1568338 | | 8/2005 |
| EP | 1582175 | | 10/2005 |
| EP | 1582176 | | 10/2005 |
| EP | 1584303 | | 10/2005 |
| EP | 1586283 | | 10/2005 |
| EP | 1591086 | | 11/2005 |
| EP | 1593359 | | 11/2005 |
| EP | 1598030 | | 11/2005 |
| EP | 1609440 | | 12/2005 |
| EP | 1674033 | | 6/2006 |
| EP | 1736123 | | 12/2006 |
| EP | 1799119 | | 6/2007 |
| EP | 1815881 A1 | | 8/2007 |
| EP | 1832252 A2 | | 9/2007 |
| FR | 2730158 A1 | | 8/1996 |
| GB | 2355937 | | 5/2001 |
| WO | WO-8911244 | | 11/1989 |
| WO | WO-8911701 | | 11/1989 |
| WO | WO-9004368 | | 5/1990 |
| WO | WO-9511057 | | 4/1995 |
| WO | WO-9715351 | | 5/1997 |
| WO | WO-9733513 | | 9/1997 |
| WO | WO-9833554 | | 8/1998 |
| WO | WO-9835610 | | 8/1998 |
| WO | WO-9901063 | | 1/1999 |
| WO | WO-9918850 | | 4/1999 |
| WO | WO-0004945 | | 2/2000 |
| WO | WO-0009047 A1 | | 2/2000 |
| WO | WO-0033738 | | 6/2000 |
| WO | WO-0072899 | | 12/2000 |
| WO | WO-0104487 | | 1/2001 |
| WO | WO-0108597 A1 | | 2/2001 |
| WO | WO-0112075 | | 2/2001 |
| WO | WO-0112076 | | 2/2001 |
| WO | WO-0112077 | | 2/2001 |
| WO | WO-0112078 | | 2/2001 |
| WO | WO-0121066 | | 3/2001 |
| WO | WO-0136014 | | 5/2001 |
| WO | WO-0145485 | | 6/2001 |
| WO | WO-0145486 | | 6/2001 |
| WO | WO-0147431 | | 7/2001 |
| WO | WO-0147432 | | 7/2001 |
| WO | WO-0147433 | | 7/2001 |
| WO | WO-0147434 | | 7/2001 |
| WO | WO-0147435 | | 7/2001 |
| WO | WO-0147440 | | 7/2001 |
| WO | WO-0147575 | | 7/2001 |
| WO | WO-0148451 | | 7/2001 |
| WO | WO-0149245 | | 7/2001 |
| WO | WO-0150832 | | 7/2001 |
| WO | WO-0150833 | | 7/2001 |
| WO | WO-0154626 | | 8/2001 |
| WO | WO-0158388 | | 8/2001 |
| WO | WO-0158390 | | 8/2001 |
| WO | WO-0158391 | | 8/2001 |
| WO | WO-0158393 | | 8/2001 |
| WO | WO-0160453 | | 8/2001 |
| WO | WO-0181890 | | 11/2001 |
| WO | WO-0200118 | | 1/2002 |
| WO | WO-0215769 | | 2/2002 |
| WO | WO-0226161 | | 4/2002 |
| WO | WO-02053228 | | 7/2002 |
| WO | WO-02055126 | | 7/2002 |
| WO | WO-02058551 | | 8/2002 |
| WO | WO-02065894 | | 8/2002 |
| WO | WO-02076289 | | 10/2002 |
| WO | WO-02082984 | | 10/2002 |
| WO | WO-02089655 | | 11/2002 |
| WO | WO-02090894 | | 11/2002 |
| WO | WO-02100481 | | 12/2002 |
| WO | WO-03002192 | | 1/2003 |
| WO | WO-03002193 | | 1/2003 |
| WO | WO-03020182 | | 3/2003 |
| WO | WO-03061467 | | 7/2003 |
| WO | WO-03061504 | | 7/2003 |
| WO | WO-03096889 | | 11/2003 |
| WO | WO-2004014245 A1 | | 2/2004 |
| WO | WO-2004014456 | | 2/2004 |
| WO | WO-2004019773 | | 3/2004 |
| WO | WO-2004058101 | | 7/2004 |
| WO | WO-2004066879 | | 8/2004 |
| WO | WO-2004110263 | | 12/2004 |
| WO | WO-2005000206 | | 1/2005 |
| WO | WO-2005007075 | | 1/2005 |
| WO | WO-2005107583 | | 11/2005 |
| WO | WO-2006001851 | | 1/2006 |
| WO | WO-2006035446 | | 4/2006 |
| WO | WO-2006108203 A2 | | 10/2006 |
| WO | WO-2006113187 | | 10/2006 |
| WO | WO-2006118790 A2 | | 11/2006 |
| WO | WO-2006122285 | | 11/2006 |

| | | |
|---|---|---|
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |
| WO | WO 2009050709 * | 4/2009 |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

European Search Report, Application No. 08253986.7, Issued Mar. 30, 2009, 5 pages.

European Search Report, Application No. 09250497.6, Issued May 13, 2009, 10 pages.

* cited by examiner

METHODS AND DEVICES FOR DIAGNOSING PERFORMANCE OF A GASTRIC RESTRICTION SYSTEM

FIELD OF THE INVENTION

The present invention relates to devices and methods for diagnosing performance of a gastric restriction system.

BACKGROUND OF THE INVENTION

Obesity is becoming a growing concern, particularly in the United States, as the number of obese people continues to increase and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a Huber needle and syringe were used to penetrate the patient's skin and add or remove fluid from the balloon via an injection port. More recently, implantable pumps have been developed which enable non-invasive adjustments of the band. An external programmer communicates with the implanted pump using telemetry to control the pump. During a scheduled visit, a physician places a handheld portion of the programmer near the gastric implant and transmits power and command signals to the implant. The implant in turn adjusts the fluid levels in the band and transmits a response command to the programmer.

During these gastric band adjustments, it has been difficult to determine how the adjustment is proceeding and whether the adjustment will have the intended effect. In an attempt to determine the efficacy of an adjustment, some physicians have utilized fluoroscopy with a Barium swallow as the adjustment is being performed. However, fluoroscopy is both expensive and undesirable due to the radiation doses incurred by both the physician and patient. Other physicians have instructed the patient to drink a glass of water during or after the adjustment to determine whether the water can pass through the adjusted stoma. This method, however, only assures that the patient is not obstructing and does not provide any information about the efficacy of the adjustment. Oftentimes, a physician may simply adopt a "try as you go" method based upon their prior experience, and the results of an adjustment may not be discovered until hours or days later, when the patient experiences a complete obstruction to the stomach cavity, or the band induces erosion of the stomach tissue due to excessive interface pressures against the band.

Accordingly, methods and devices are provided for use with an implantable restriction device, and in particular for diagnosing performance of an implantable restriction system.

SUMMARY OF THE INVENTION

The present invention generally provides methods and devices for diagnosing performance of a gastric restriction system. In one embodiment, a method of monitoring a restriction in a patient is provided that includes comparing a sequence of gathered pressure data values regarding a restriction device implanted in a patient to form a restriction against a baseline sequence of pressure data values characteristic of the patient. The method also includes determining, if the sequence of gathered pressure data values varies from the baseline sequence, a possible cause of the variation and, in some embodiments, a suggested corrective action to address the possible cause of the variation. The suggested corrective action can include any one of adjusting an amount of fluid disposed within the restriction device, advising the patient to more thoroughly chew food, advising the patient to seek medical attention, recommending that the patient adjust diet, and recommending that the patient adjust eating habits. The possible cause of the variation can be any one of too much fluid disposed within the restriction device and too little fluid disposed within the restriction device. In some embodiments, determining the possible cause of the variation can include determining whether the sequence of gathered pressure data values includes pressure data values above and/or below pressure data values included in the baseline sequence, whether a duration of the sequence of gathered pressure data values varies from a duration of the baseline sequence, and/or whether a frequency of data values included in the sequence of gathered pressure data values varies from a frequency of data values included in the baseline sequence.

The method can have any number of variations. In some embodiments, the method can also include gathering the sequence of pressure data values using an implantable pressure measuring device in communication with the restriction device. Another variation includes correlating the sequence of gathered pressure data with a record of patient satiety levels, while another variation includes correlating the sequence of gathered pressure data with a record of food eaten by the patient and determining, based on the correlation, if an eating habit modification should be suggested to the patient. The method can also include comparing the record of food eaten by the patient with the patient's weight loss trend and determining, based on the comparing, if a corrective action should be taken.

In another embodiment, a method of monitoring a restriction in a patient is provided that includes determining if a pressure within an implantable restriction device configured to form a restriction in a patient measured over a period of time differs from an expected pressure (e.g., an expected pressure for a typical patient or a pressure generated using historical pressure data for the implantable restriction device in the patient) over the period of time and, if so, triggering an alarm. Triggering the alarm can include displaying on a display device a notice that the pressure measured over the period of time was determined to differ from the expected pressure over the period of time. In some embodiments, the method can also include diagnosing at least one possible cause of the difference between the pressure measured over the period of time and the expected pressure over the period of time. The alarm to be triggered can be based on the at least one diagnosed possible cause.

In other aspects, a system for monitoring a restriction in a patient is provided. The system includes a pressure measuring element configured to measure a pressure within an implantable restriction device configured to form a restriction in a patient and a processor configured to compare a pressure profile including two or more pressure data values measured by the pressure measuring element with a baseline pressure profile for the patient and to determine if the pressure profile differs from the baseline pressure profile. In some embodiments, if the pressure profile differs from the baseline pressure profile, the processor is configured to determine at least one possible cause of the difference and a possible corrective action to address the difference. The baseline pressure profile can include, for example, typical pressure data values, for the patient or for a typical patient, over a time of day corresponding to a time of day when the pressure measuring element gathered the pressure data values included in the pressure profile.

The system can be implemented in a variety of ways. For example, the system can also include a base unit including the processor, wherein the base unit is at a location remote from the patient. In other embodiments, the system includes an external storage mechanism including the processor, wherein the external storage mechanism is at a location local to the patient. In some embodiments, the system also includes an external display device configured to provide a notice if the pressure profile differs from the baseline pressure profile. A user can, in some embodiments, use the display device to trigger a corrective action to address the difference. In some embodiments, the system also includes a storage mechanism configured to store pressure data values measured by the pressure measuring element. The processor can retrieve stored pressure data values from the storage mechanism and can, in some embodiments, be configured to generate a pressure profile using pressure data values retrieved from the storage mechanism.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for diagnosing performance of an implantable restriction system. In general, the devices and methods can enable patients, health care providers, and others to use pressure data as a feedback mechanism to monitor efficacy of an implantable restriction device and to identify, train, and/or prescribe treatment plan options. The pressure data can include any pressure data, such as all pressure data or only clinically relevant pressure data. Pressure data monitoring can be used locally and/or remotely to monitor a restriction in a patient and compare gathered pressure data with a typical pressure of the restriction. Based on the results of the comparison, possible problems related to the patient and the restriction can be identified and diagnosed with possible cause(s) and solution(s). Notice of any detected possible problems, causes, and/or solutions can be provided to a user. Such data analysis can thereby improve detection of and response time to possible problems with a patient's treatment plan, including activity of the patient and of the restriction device, thereby helping to improve effectiveness of the restriction device and increase motivation and satisfaction of the patient. For example, pressure measurements can be obtained from when a patient swallows a particular food portion, and based on analysis of such pressure feedback, the patient can be advised or taught to eat smaller portions, larger portions, or similar size portions. As another example, a patient can test desired foods for appropriateness based on pressure feedback together with portion size and/or based on any other parameters. In still another example, analysis of sensed pressure data can indicate a malfunction in the restriction system, thereby enabling prompt identification and treatment of the malfunction.

Figure 1A:
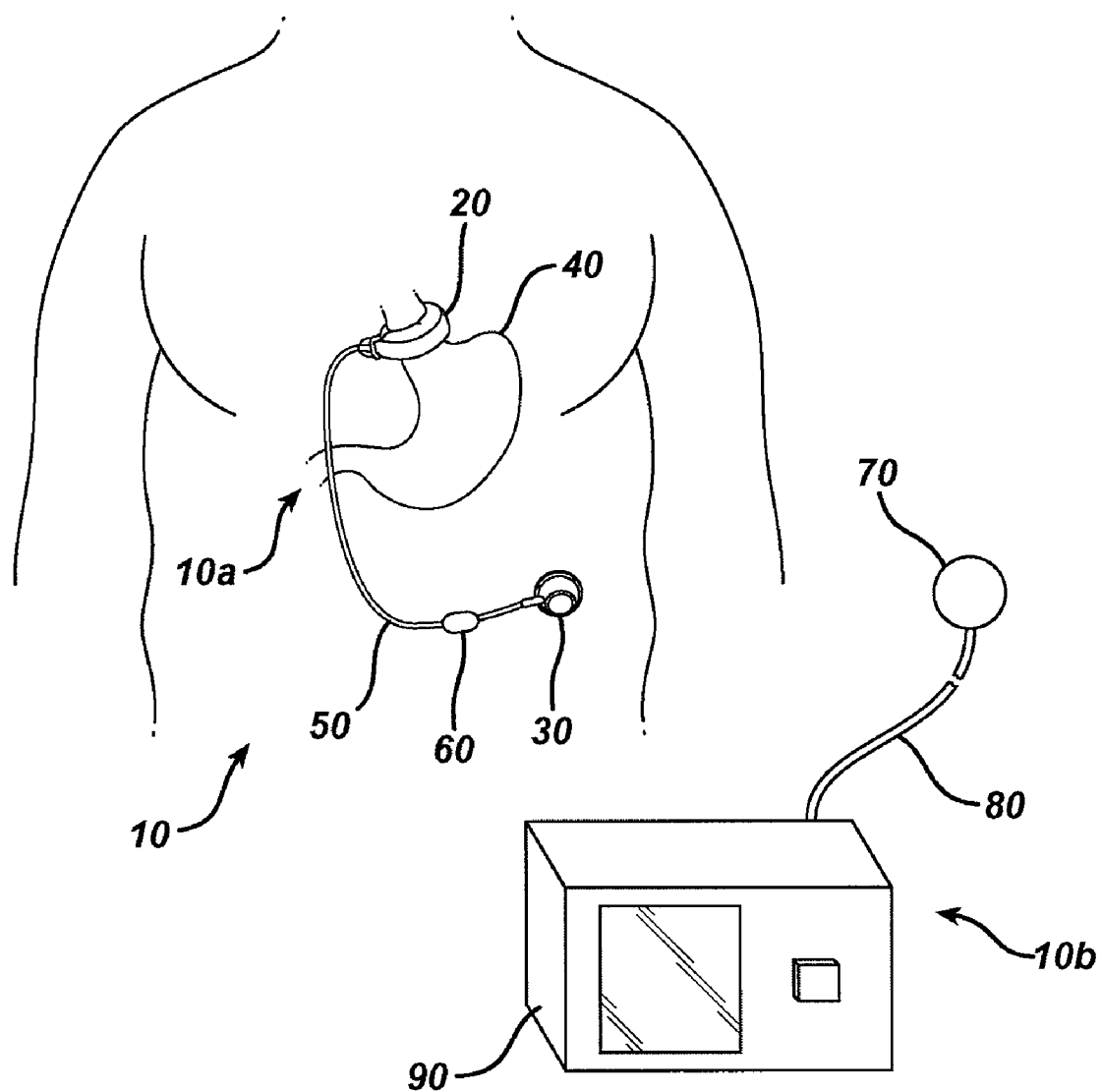
FIG. 1A is a schematic diagram of an embodiment of a food intake restriction system.
Figure 1B:
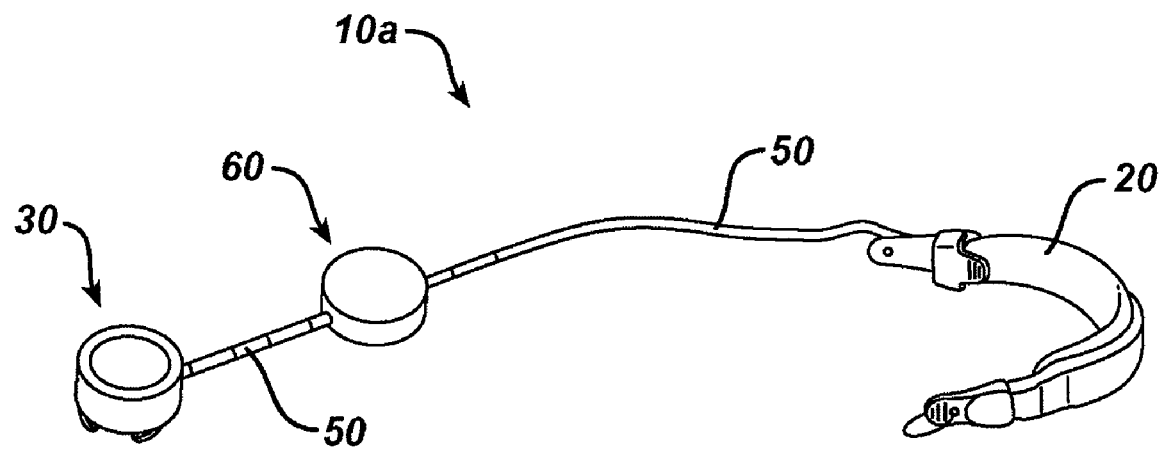
FIG. 1B is a perspective view of an embodiment of an implantable portion of the food intake restriction system of FIG. 1A.

While the present invention can be used with a variety of restriction systems known in the art, FIG. 1A illustrates one exemplary embodiment of a food intake restriction system 10 in use in a patient. As shown, the system 10 generally includes an implantable portion 10a and an external portion 10b. FIG. 1B illustrates the implantable portion 10a outside of a patient. As shown, the implantable portion 10a includes an adjustable gastric band 20 that is configured to be positioned around the upper portion of a patient's stomach 40 and an injection port housing 30 that is fluidly coupled to the adjustable gastric band 20, e.g., via a catheter 50. The injection port 30 is adapted to allow fluid to be introduced into and removed from the gastric band 20 to thereby adjust the size of the band 20 and thus the pressure applied to the stomach 40. The injection port 30 can thus be implanted at a location within the body that is accessible through tissue. Typically, injection ports are positioned in the lateral subcostal region of the patient's abdomen under the skin and layers of fatty tissue. Surgeons also typically implant injection ports on the sternum of the patient.

The internal portion 10a can also include a sensing or measuring device that is in fluid communication with the closed fluid circuit in the implantable portion 10a. In one embodiment, the sensing device is a pressure sensing device configured to measure the fluid pressure of the closed fluid circuit. While the pressure measuring device can have various configurations and can be positioned anywhere along the internal portion 10a, including within the injection port 30 and as described further below, in the illustrated embodiment the pressure measuring device is in the form of a pressure sensor that is disposed within a sensor housing 60 positioned adjacent to the injection port 30. The catheter 50 can include a first portion that is coupled between the gastric band 20 and the pressure sensor housing 60 and a second portion that is coupled between the pressure sensor housing 60 and the injection port 30. While it is understood that the sensing device can be configured to obtain data relating to one or more relevant parameters (including any data related to the parameter(s), such as all raw data or only clinically relevant data), generally it will be described herein in a context of a pressure sensing device.

In addition to sensing pressure of fluid within the internal portion 10a as described herein, pressure of fluid within the esophagus and/or the stomach 40 can also be sensed using any suitable device, such as an endoscopic manometer. By way of non-limiting example, such fluid pressure measurements can be compared against measured pressure of fluid within the internal portion 10a before, during, and/or after adjustment of pressure within the internal portion 10a. Other suitable uses for measured pressure within the esophagus and/or the stomach 40 will be appreciated by those skilled in the art.

As further shown in FIG. 1A, the external portion 10b generally includes a data reading device 70 that is configured to be positioned on the skin surface above the pressure sensor housing 60 (which can be implanted beneath thick tissue, e.g., over 10 cm thick) to non-invasively communicate with the pressure sensor housing 60 and thereby obtain pressure measurements. The data reading device 70 can optionally be electrically coupled (wirelessly or wired, as in this embodiment via an electrical cable assembly 80) to a control box 90 that can display the pressure measurements, other data obtained from the data reading device 70, and/or data alerts, as discussed further below. While shown in this example as located local to the patient, the control box 90 can be at a location local to or remote from the patient.

In some embodiments, the external portion 10b can include a sensing system configured to obtain data related to one or more relevant parameters, such as fluid pressure of the closed fluid circuit of the internal portion 10a. For example, pressure in the closed fluid circuit can be measured through a Huber needle in fluid communication with the injection port 30. An exemplary external pressure reading system is described in U.S. Publication No. 2006/0211912, entitled "External Pressure-Based Gastric Band Adjustment System and Method" which is hereby incorporated by reference.

Figure 2A:
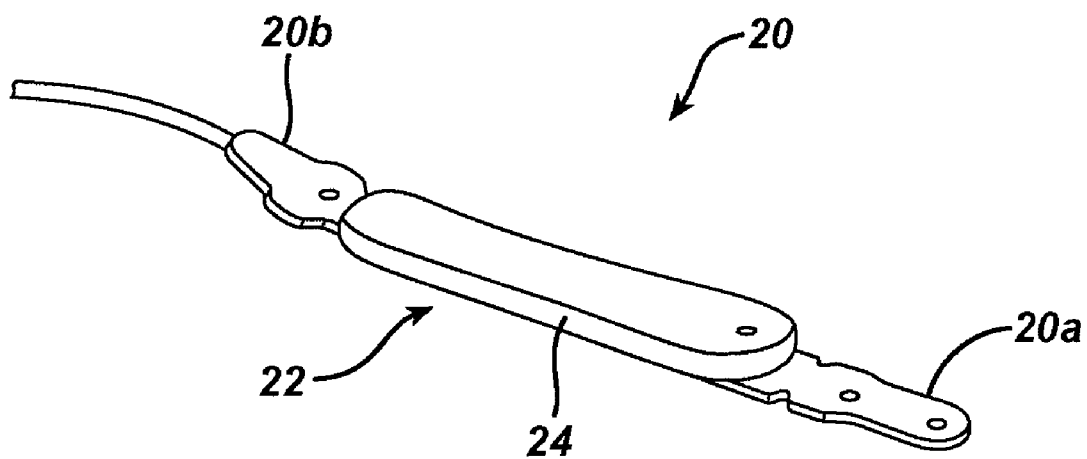
FIG. 2A is a perspective view of the food intake restriction device of FIG. 1A.

FIG. 2A shows the gastric band 20 in more detail. While the gastric band 20 can have a variety of configurations, and various gastric bands currently known in the art can be used with the present invention, in the illustrated embodiment the gastric band 20 has a generally elongate shape with a support structure 22 having first and second opposite ends 20a, 20b that can be formed in a loop such that the ends are secured to each other. Various mating techniques can be used to secure the ends 20a, 20b to one another. In the illustrated embodiment, the ends 20a, 20b are in the form of straps that mate together, with one laying on top of the other. In another embodiment, illustrated, for example, in FIGS. 1B and 2B, a support structure at one end of the gastric band 20 can include an opening through which the other end of the gastric band 20 can feed through to secure the ends to one another. The gastric band 20 can also include a variable volume member, such as an inflatable balloon 24, that is disposed or formed on one side of the support structure 22 and that is configured to be positioned adjacent to tissue. The balloon 24 can expand or contract against the outer wall of the stomach to form an adjustable stoma for controllably restricting food intake into the stomach.

A person skilled in the art will appreciate that the gastric band can have a variety of other configurations. Moreover, the various methods and devices disclosed herein have equal applicability to other types of implantable bands. For example, bands are used for the treatment of fecal incontinence, as described in U.S. Pat. No. 6,461,292 which is hereby incorporated by reference. Bands can also be used to treat urinary incontinence, as described in U.S. Publication No. 2003/0105385 which is hereby incorporated by reference. Bands can also be used to treat heartburn and/or acid reflux, as disclosed in U.S. Pat. No. 6,470,892 which is hereby incorporated by reference. Bands can also be used to treat impotence, as described in U.S. Publication No. 2003/0114729 which is hereby incorporated by reference.

Figure 2B:
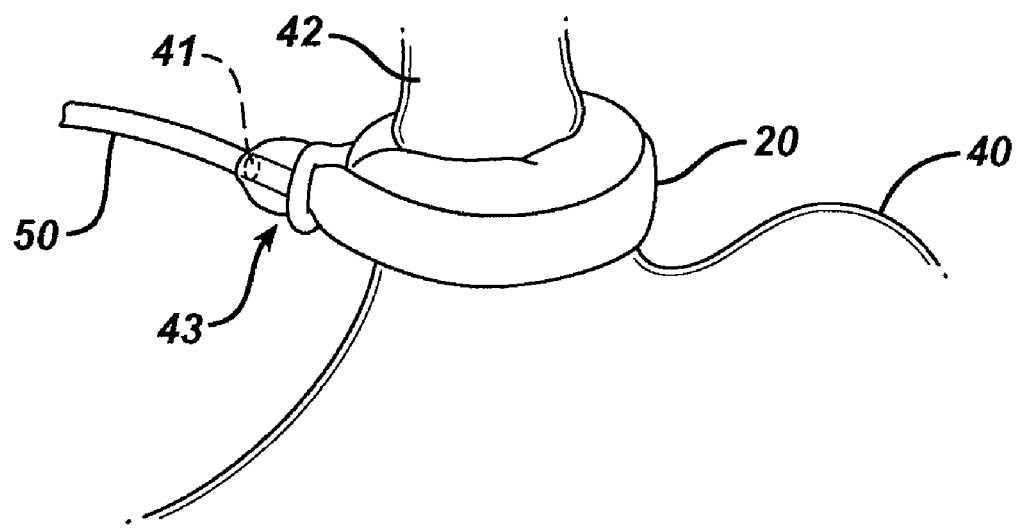
FIG. 2B is a schematic diagram of the food intake restriction device of FIG. 2A applied about the gastro-esophageal junction of a patient.

FIG. 2B shows the adjustable gastric band 20 applied about the gastro-esophageal junction of a patient. As shown, the band 20 at least substantially encloses the upper portion of the stomach 40 near the junction with the patient's esophagus 42. After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band 20. FIG. 2B also shows an alternate location of a sensing device 41, disposed in a buckle 43 of the band 20.

Figure 3:
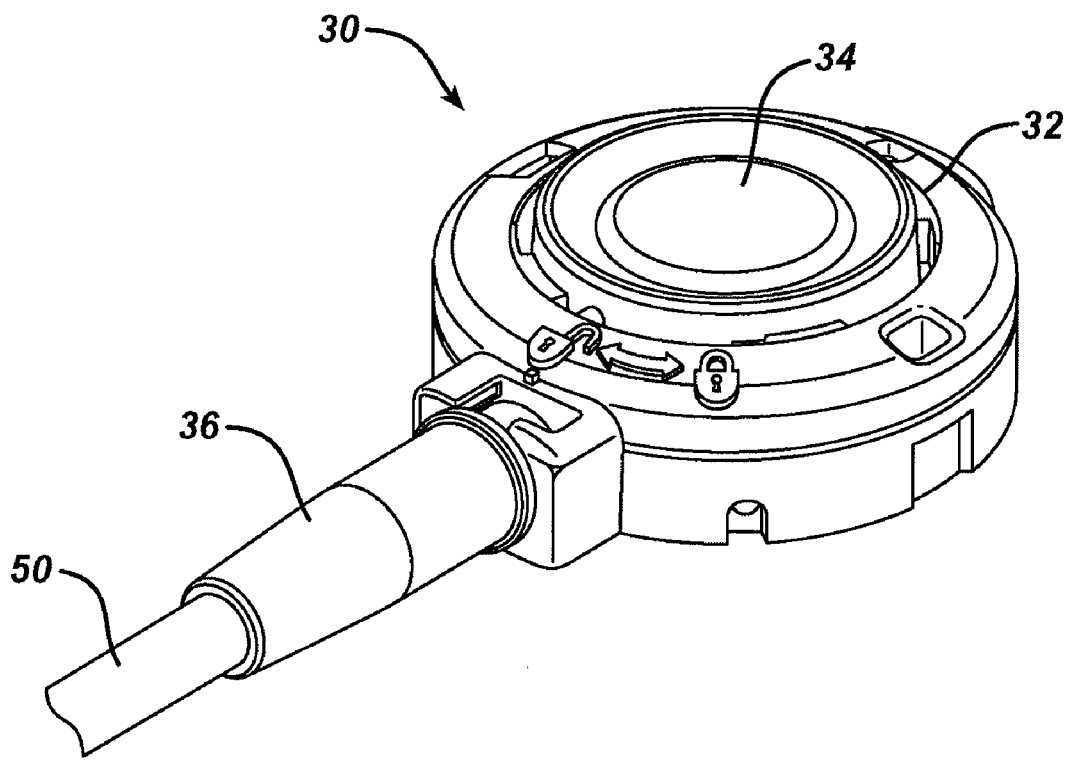
FIG. 3 is a perspective view of an embodiment of the injection port housing of FIG. 1A.

The fluid injection port 30 can also have a variety of configurations. In the embodiment shown in FIG. 3, the injection port 30 has a generally cylindrical housing with a distal or bottom surface and a perimeter wall extending proximally from the bottom surface and defining a proximal opening 32. The proximal opening 32 can include a needle-penetrable septum 34 extending there across and providing access to a fluid reservoir (not visible in FIG. 3) formed within the housing. The septum 34 is preferably placed in a proximal enough position such that the depth of the reservoir is sufficient enough to expose the open tip of a needle, such as a Huber needle, so that fluid transfer can take place. The septum 34 is preferably arranged so that it will self seal after being punctured by a needle and the needle is withdrawn. As further shown in FIG. 3, the port 30 can further include a catheter tube connection member 36 that is in fluid communication with the reservoir and that is configured to couple to a catheter (e.g., the catheter 50). A person skilled in the art will appreciate that the housing can be made from any number of materials, including stainless steel, titanium, ceramic, glass, or polymeric materials, and the septum 34 can likewise be made from any number of self healing, elastomeric materials, including silicone.

The reading device 70 can also have a variety of configurations, and one exemplary pressure reading device is disclosed in more detail in commonly-owned U.S. Publication No. 2006/0189888 and U.S. Publication No. 2006/0199997, which are hereby incorporated by reference. In general, the reading device 70 can non-invasively measure the pressure of the fluid within the implanted portion 10a even when the pressure sensing device is implanted beneath thick (at least over 10 cm, and possibly over 15 cm) subcutaneous fat tissue. The physician can hold the reading device 70 against the patient's skin near the location of the sensor housing 60 and/or other pressure sensing device location(s), obtain sensed pressure data and possibly other information as discussed herein, and observe the pressure reading (and/or other data) on a display on the control box 90. The data reading device 70 can also be removably attached to the patient, as discussed further below, such as during a prolonged examination, using straps, adhesives, and other well-known methods. The data reading device 70 can operate through conventional cloth or paper surgical drapes, and can also include a disposal cover (not shown) that may be replaced for each patient.

Figure 4:
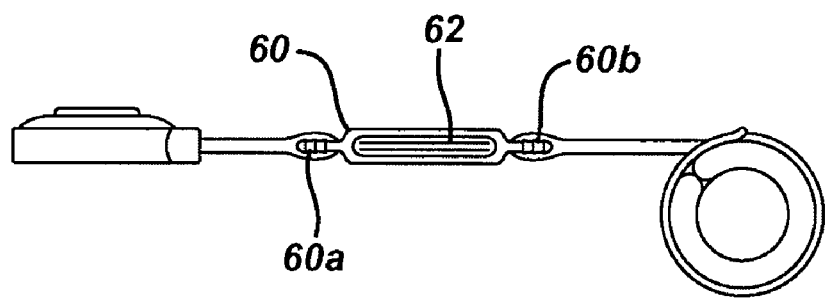
FIG. 4 is a perspective view of an embodiment of the sensor housing of FIG. 1A.

As indicated above, the system 10 can also include a pressure measuring device in communication with the closed fluid circuit and configured to measure pressure (e.g., fluid pressure) which corresponds to the amount of restriction applied by the adjustable gastric band 20 to the patient's stomach 40. In the illustrated embodiment, as shown in FIG. 4, the pressure measuring device is in the form of a pressure sensor 62 disposed within the sensor housing 60. The pressure measuring device can, however, be disposed anywhere within the closed hydraulic circuit of the implantable portion, and various exemplary locations and configurations are disclosed in more detail in commonly-owned U.S. Publication No. 2006/0211913 entitled "Non-Invasive Pressure Measurement In a Fluid Adjustable Restrictive Device," filed on Mar. 7, 2006 and hereby incorporated by reference. In general, the illustrated sensor housing 60 includes an inlet 60a and an outlet 60b that are in fluid communication with the fluid in the implantable portion 10a. An already-implanted catheter 50 can be retrofitted with the sensor housing 60, such as by severing the catheter 50 and inserting barbed connectors (or any other connectors, such as clamps, clips, adhesives, welding, etc.) into the severed ends of the catheter 50. The sensor 62 can be disposed within the housing 60 and be configured to respond to fluid pressure changes within the hydraulic circuit and convert the pressure changes into a usable form of data.

Various pressure sensors known in the art can be used as the pressure sensor 62, such as a wireless pressure sensor provided by CardioMEMS, Inc. of Atlanta, Ga., though a suitable MEMS pressure sensor may be obtained from any other source, including but not limited to Integrated Sensing Systems, Inc. (ISSYS) of Ypsilanti, Mich. and Remon Medical Technologies, Inc. of Waltham, Mass. One exemplary MEMS pressure sensor is described in U.S. Pat. No. 6,855,115, the disclosure of which is incorporated by reference herein for illustrative purposes only. It will also be appreciated by a person skilled in the art that suitable pressure sensors can include, but are not limited to, capacitive, piezoresistive, silicon strain gauge, or ultrasonic (acoustic) pressure sensors, as well as various other devices capable of measuring pressure.

Figure 5:
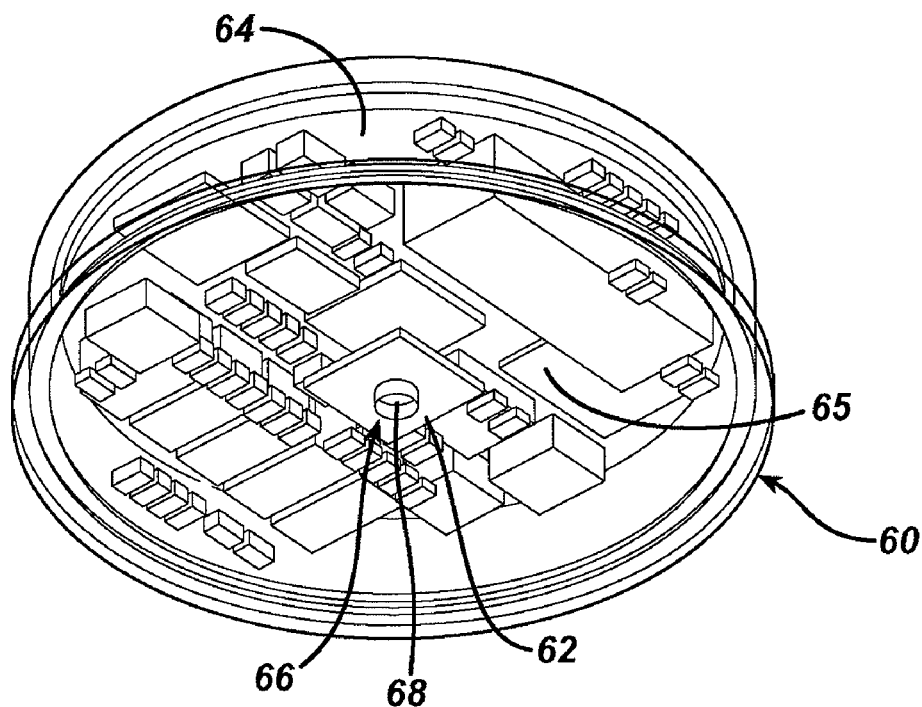
FIG. 5 illustrates an embodiment of the sensor housing of FIG. 1A.

One embodiment of a configuration of the sensor housing 60 having the sensor 62 disposed within it is shown in FIG. 5. The sensor housing 60 in this example can be made of a two piece construction including a circuit board, which can be made of a hermetic material to serve as a hermetic component (bottom), and a hermetic top of compatible material bonded together to prevent fluid from contacting any elements disposed within the sensor housing 60, except as discussed for the sensor 62. The sensor housing 60 can be made from any biocompatible material appropriate for use in a body, such as a polymer, biocompatible metal, ceramic, glass, and other similar types of material. Furthermore, the sensor housing 60 can be made from any one or more of transparent (as shown in FIG. 5), opaque, semi-opaque, and radio-opaque materials. A circuit board 64 including, among other elements, a microcontroller 65 (e.g., a processor), can also be disposed within the housing 60 to help process and communicate pressure measurements gathered by the sensor 62, and also possibly other data related to the band 20. (The circuit board 64 can also be part of the housing 60, as mentioned above.) As further discussed below, the circuit board 64 can also include a transcutaneous energy transfer (TET)/telemetry coil and a capacitor. Optionally, a temperature sensor can be integrated into the circuit board 64. The microcontroller 65, the TET/telemetry coil, the capacitor, and/or the temperature sensor can be in communication via the circuit board 64 or via any other suitable component(s). The TET/telemetry coil and capacitor can collectively form a tuned tank circuit for receiving power from the external portion 10b and transmitting pressure measurements to a pressure reading device, e.g., the reading device 70. Moreover, to the extent that a telemetry component associated with the pressure sensor 62 is unable to reach a telemetry device external to the patient without some assistance, such assistance can be provided by any suitable number of relays (not shown) or other devices.

Fluid can enter the sensor housing 60 through an opening 66 located anywhere on the housing's surface (here, its bottom surface) and come into contact with a pressure sensing surface 68 of the sensor 62. The sensor 62 is typically hermetically sealed to the motherboard such that fluid entering the opening 66 cannot infiltrate and affect operation of the sensor 62 except at the pressure sensing surface 68. The sensor 62 can measure the pressure of fluid coming into contact with the pressure sensing surface 68 as fluid flows in and out of the opening 66. For example, the pressure sensing surface 68 can include a diaphragm having a deformable surface such that when fluid flows through the opening 66, the fluid impacts the surface of the diaphragm, causing the surface to mechanically displace. The mechanical displacement of the diaphragm can be converted to an electrical signal by a variable resistance circuit including a pair of variable resistance, silicon strain gauges. One strain gauge can be attached to a center portion of diaphragm to measure the displacement of the diaphragm, while the second, matched strain gauge can be attached near the outer edge of diaphragm. The strain gauges can be attached to the diaphragm with adhesives or can be diffused into the diaphragm structure. As fluid pressure within band 20 fluctuates, the surface of the diaphragm can deform up or down, thereby producing a resistance change in the center strain gauge.

Figure 6:
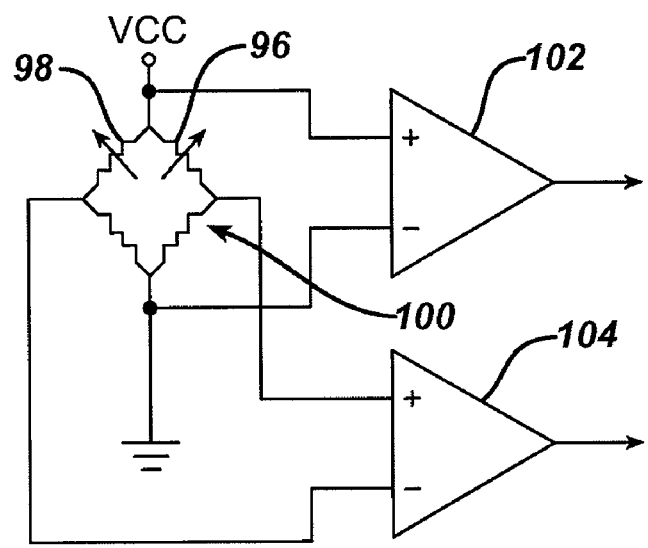
FIG. 6 is a schematic of an embodiment of a variable resistance circuit for the pressure sensor of FIG. 5.

One embodiment of a variable resistance circuit for the sensor 62 is shown in FIG. 6. The circuit includes first and second strain gauges 96, 98 that form the top two resistance elements of a half-compensated, Wheatstone bridge circuit 100. As the first strain gauge 96 reacts to the mechanical displacements of the sensor's diaphragm, the changing resistance of the first gauge 96 changes the potential across the top portion of the bridge circuit 100. The second strain gauge 98 is matched to the first strain gauge 96 and athermalizes the Wheatstone bridge circuit 100. First and second differential amplifiers 102, 104 are connected to the bridge circuit 100 to measure the change in potential within the bridge circuit 100 due to the variable resistance strain gauges 96, 98. In particular, the first differential amplifier 102 measures the voltage across the entire bridge circuit 100, while the second differential amplifier 104 measures the differential voltage across the strain gauge half of bridge circuit 100. The greater the differential between the strain gauge voltages, for a fixed voltage across the bridge, the greater the pressure difference. Output signals from the differential amplifiers 102, 104 can be applied to the microcontroller 65 integrated into the circuit board 64, and the microcontroller 65 can transmit the measured pressure data to a device external to the patient. If desired, a fully compensated Wheatstone bridge circuit can also be used to increase the sensitivity and accuracy of the pressure sensor 62. In a fully compensated bridge circuit, four strain gauges are attached to the surface of diaphragm rather than only two strain gauges.

Figure 7:
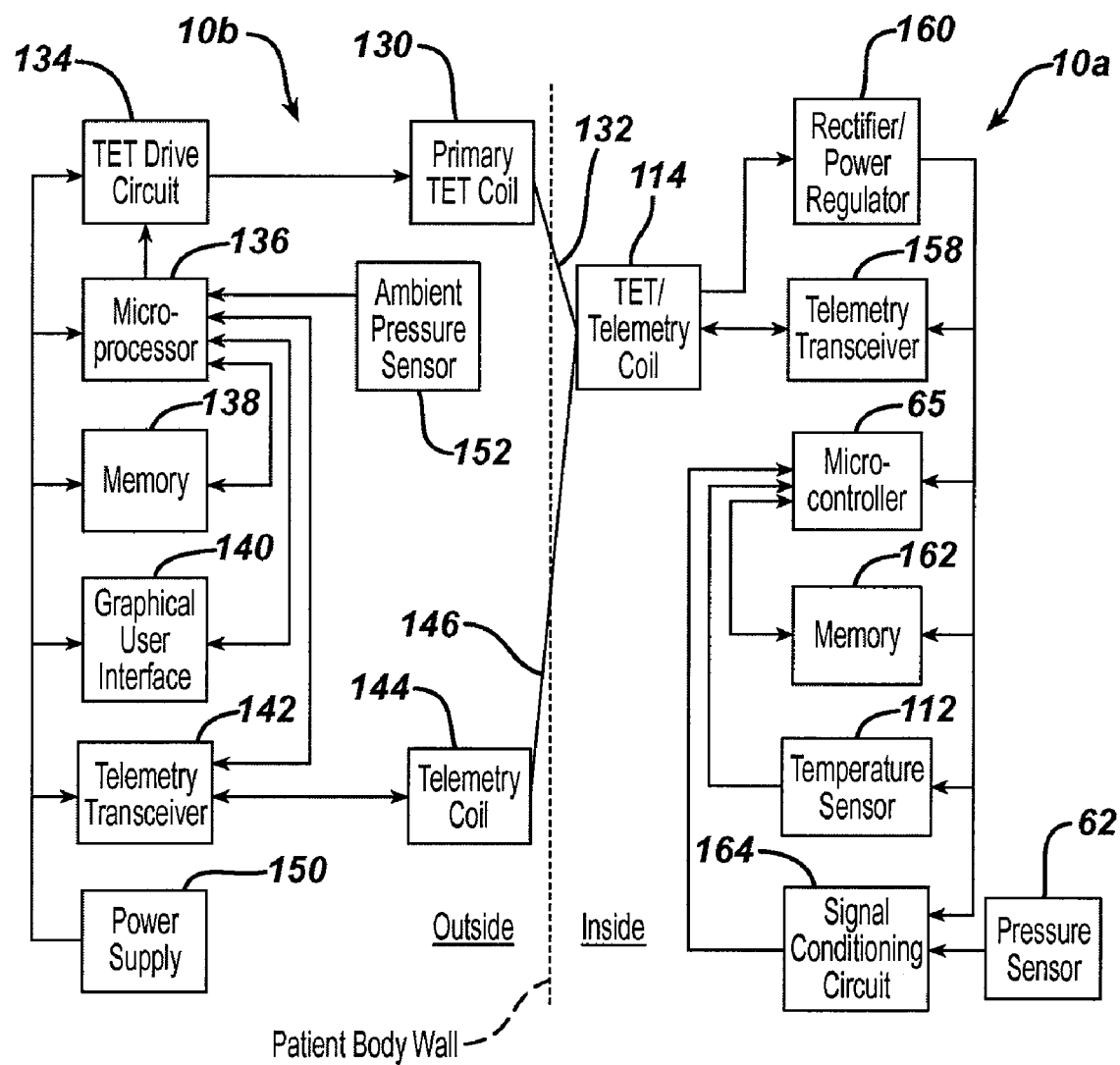
FIG. 7 is a block diagram showing an embodiment of internal and external components of the food intake restriction device of FIG. 1A.

FIG. 7 illustrates one embodiment of components included in the internal and external portions 10a, 10b. As shown in FIG. 7, the external portion 10b includes a primary TET coil 130 for transmitting a power signal 132 to the internal portion 10a. A telemetry coil 144 is also included for transmitting data signals to the internal portion 10a. The primary TET coil 130 and the telemetry coil 144 combine to form an antenna, e.g., the reading device 70. The external portion 10b, e.g., disposed in the control box 90, includes a TET drive circuit 134 for controlling the application of power to the primary TET coil 130. The TET drive circuit 134 is controlled by a microprocessor 136 having an associated memory 138. A graphical user interface 140 is connected to the microprocessor 136 for inputting patient information, displaying data and physician instructions, and/or printing data and physician instructions. Through the user interface 140, a user such as the patient or a clinician can transmit an adjustment request to the physician and also enter reasons for the request. Additionally, the user interface 140 can enable the patient to read and respond to instructions from the physician and/or pressure measurement alerts, as discussed further below.

The external portion 10b also includes a primary telemetry transceiver 142 for transmitting interrogation commands to and receiving response data, including sensed pressure data, from the implanted microcontroller 65. The primary transceiver 142 is electrically connected to the microprocessor 136 for inputting and receiving command and data signals. The primary transceiver 142 drives the telemetry coil 144 to resonate at a selected RF communication frequency. The resonating circuit can generate a downlink alternating magnetic field 146 that transmits command data to the microcontroller 65. Alternatively, the transceiver 142 can receive telemetry signals transmitted from a secondary TET/telemetry coil 114 in the internal portion 10a. The received data can be stored in the memory 138 associated with the microprocessor 136. A power supply 150 can supply energy to the control box 90 in order to power element(s) in the internal portion 10a. An ambient pressure sensor 152 is connected to microprocessor 136. The microprocessor 136 can use a signal from the ambient pressure sensor 152 to adjust the received pressure measurements for variations in atmospheric pressure due to, for example, variations in barometric conditions or altitude, in order to increase the accuracy of pressure measurements.

FIG. 7 also illustrates components of the internal portion 10a, which in this embodiment are included in the sensor housing 60 (e.g., on the circuit board 64). As shown in FIG. 7, the secondary TET/telemetry coil 114 receives the power/communication signal 132 from the external antenna. The secondary coil 114 forms a tuned tank circuit that is inductively coupled with either the primary TET coil 130 to power the implant or the primary telemetry coil 144 to receive and transmit data. A telemetry transceiver 158 controls data exchange with the secondary coil 114. Additionally, the internal portion 10a includes a rectifier/power regulator 160, the microcontroller 65, a memory 162 associated with the microcontroller 65, a temperature sensor 112, the pressure sensor 62, and a signal conditioning circuit 164. The implanted components can transmit pressure measurements (with or without adjustments due to temperature, etc.) from the sensor 62 to the control box 90 via the antenna (the primary TET coil 130 and the telemetry coil 144). Pressure measurements can be stored in the memory 138, adjusted for ambient pressure, shown on a display on the control box 90, and/or transmitted, possibly in real time, to a remote monitoring station at a location remote from the patient.

Figure 8:
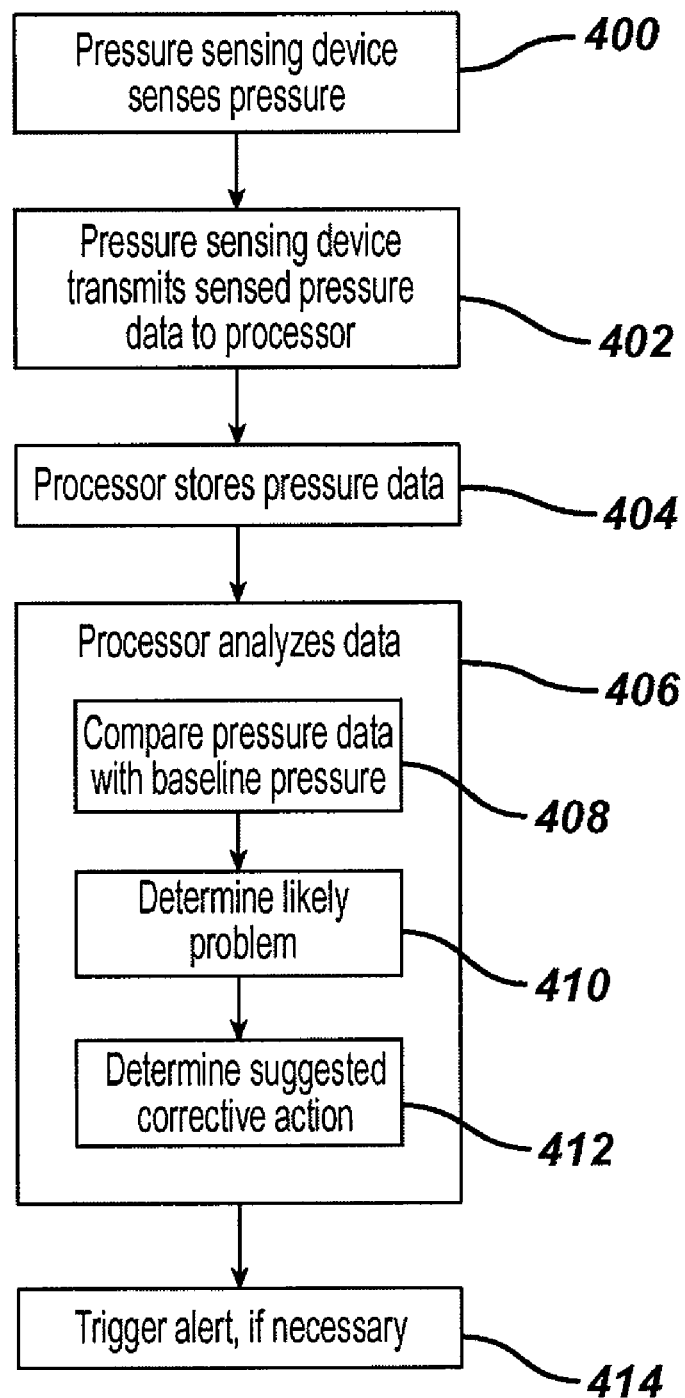
FIG. 8 is a flow diagram showing an embodiment of a data analysis protocol for data gathered by the pressure sensor of FIG. 5.
Figure 9:
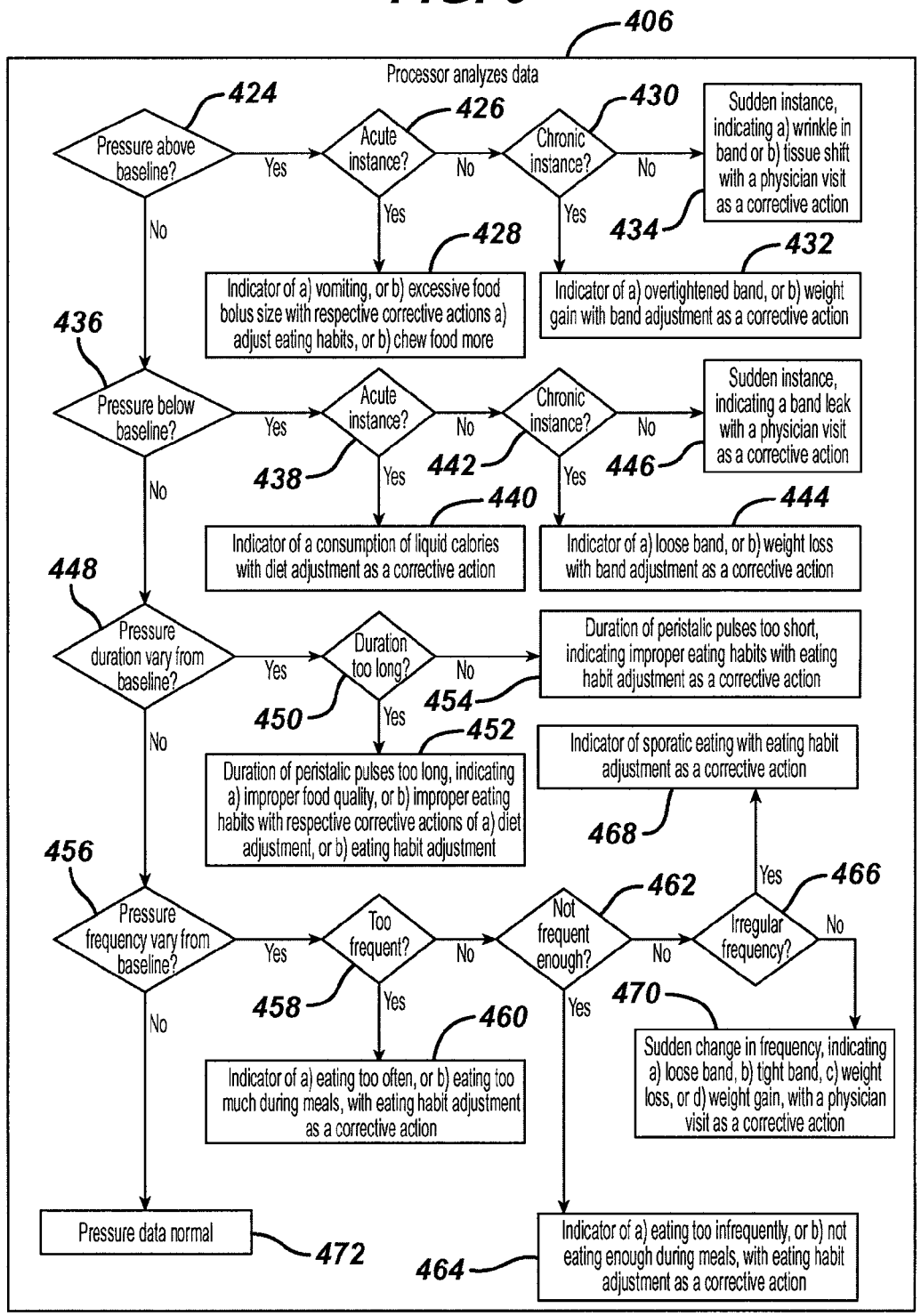
FIG. 9 is a flow diagram showing an expanded embodiment of the data analysis protocol of FIG. 8.

As illustrated in one embodiment of a process shown in FIGS. 8-9, the sensor housing 60 can generally sense pressure within the gastric band 20, analyze the sensed pressure data (e.g., using the microcontroller 65) to determine if the sensed pressure data varies from a baseline or typical pressure, and, if a variation exists, determine at least one possible cause of the variation and at least one suggested corrective action to address the determined possible cause of the variation. The sensor housing 60 can also provide an alert or alarm to the control box 90 (e.g., through the reading device 70) indicating the variation, the possible cause(s), and/or the suggested corrective action(s), which the control box 90 can provide to a user by, for example, displaying the alert (e.g., using the user interface 140). Such detection and diagnosis of a pressure variation can provide a patient, a physician, and/or any other user with evaluations of the efficacy of the band 20, including possible solutions to correct for any undesirable sensed data, thereby allowing for improved functionality of the band, for timely (possibly in real time) attention to problems before they worsen or adversely affect patient morale, and/or for other diagnostic or treatment advantages.

While the process shown in FIGS. 8-9 (and FIG. 22, below) is discussed with relation to the elements included in FIGS. 1A-7, a person skilled in the art will appreciate that the process can be modified to include more or fewer elements, reorganized or not, and can be performed in the system 10 or in another, similar system having other, similar elements. For example, the microcontroller 65 processes instructions in this embodiment, but any processor configured to process instructions for a system (e.g., a central processing unit, a microprocessor, a digital signal processing unit, application specific integrated circuits (ASICs), a state machine, an analog computer, an optical or photonic computer, logic circuitry, etc.) can be used. Furthermore, the sensor 62 in this illustrated embodiment measures fluid pressure, but any sensed pressure data related to the band 20 can be handled as discussed herein.

In use, the sensor housing 60 can sense 400 a pressure of fluid disposed within the band 20 using the sensor 62. The sensor 62 can transmit 402 measured signals, such as to the signal conditioning circuit 164, which can amplify the signals before the signal conditioning circuit 164 transmits the measured pressure data to the microcontroller 65. Alternatively, in some embodiments, the sensor 62 can directly transmit 402 signals to the microcontroller 65. In this embodiment, the pressure sensor 62 provides pressure data at an update rate of approximately 20 Hz. Such a rate can provide a telemetry/TET mode cycle completion approximately every 50 ms. For example, the TET/telemetry coil 114 can provide TET for the sensor housing 60 for approximately 45 ms to power the sensor housing 60 and then provide telemetry of pressure data for approximately 5 ms. Of course, any other switching topology can be used. It will also be appreciated that switching between TET and telemetry may be unnecessary. For example, the sensor housing 60 can be active, such that TET is not required. As another example, a second coil (not shown) can be added to the sensor housing 60, with one of the coils in the sensor housing 60 being dedicated to TET and the other to telemetry. Still other alternatives and variations will be apparent to those of ordinary skill in the art, such as a passive telemetry scheme such as those disclosed in WO 89/11701 of Peter A. Neukomm entitled "Interrogation and Remote Control Device" and in P. A. Neukomm and H. Kündig, "Passive Wireless Actuator Control and Sensor Signal Transmission," *Sensors and Actuators*, vol. A21-A23 (1990), pp. 258-262.

Having received sensed pressure data, the microcontroller 65 can store 404 the data, e.g., in the memory 162. Any type of memory can be used for the memory 162, including but not limited to one or more of volatile (e.g., SRAM, etc.), non-volatile (e.g., flash, hard drive, etc.), or other memory. The microcontroller 65 can store any or all portions of sensed pressure data in the memory 162. Although in this embodiment the microcontroller 65 stores pressure data before analyzing the pressure data as described below, the microcontroller 65 can store pressure data in the memory 162 before and/or after analyzing the data, if the microcontroller 65 stores the data in the memory 162 at all. Furthermore, the memory 162 can be used to store pre-selected information or pre-selected types of information. For example, the memory 162 can store maximum, minimum, and/or baseline pressure measurements, fluoroscopic images or video of a patient swallowing, and/or any other information. Other information suitable for storing in the memory 162 will be appreciated by those skilled in the art.

The microcontroller 65 (or any other processor as described herein) can analyze 406 pressure data in a variety of ways. Typically, the microcontroller 65 analyzes a sequence of pressure data values measured over a period of time rather than analyzing every discrete pressure measurement, thereby allowing analysis of pressure trends over time and saving processing resources by not necessarily having to continually analyze incoming data. In other words, the microcontroller 65 can store all sensed data in the memory 162 and retrieve and analyze any portion of the stored data every "X" minutes and/or upon signal from an external device. The microcontroller 65 can, however, evaluate individual pressure data measurements (and/or a range of data), e.g., to identify invalid data and discard any invalid data.

Generally, in analyzing pressure data, the microcontroller 65 compares 408 sensed pressure data with baseline pressure data within the band 20, typically correlating to a time the pressure data was gathered by the sensor 62 (e.g., breakfast, dinner, midnight to 1:00 a.m., 5:00 p.m. to 5:30 p.m., Saturday, etc.). Pressure data can be correlated to a time of day by, for example, being time-stamped or being determined to be related to a particular meal based on one or more factors considered by the microcontroller 65, such as a combination of a time of day when the sensor 62 measured the data and a duration of pressure values above the baseline pressure data. The baseline pressure is typically programmed into the microcontroller 65 by a physician based on historical band performance in the patient or, particularly for recently implanted bands, in a typical patient. Baseline pressure can therefore vary between patients and even for an individual patient as the patient loses weight or otherwise experiences changes that can affect the patient's treatment plan. Baseline pressure is typically expressed as pressure over time, e.g., a curve that may or may not have a constant pressure value over a particular time period. Moreover, the microcontroller 65 can generate the baseline pressure using previously sensed pressure data, e.g., data stored in the memory 162.

If the measured pressure varies from the baseline pressure, then the microcontroller 65 can determine 410 at least one likely problem that may have caused the variation. The microcontroller 65 can also determine 412 at least one suggested corrective action to address the likely problem(s), e.g., tighten the band 20, reduce caloric intake, etc. The microcontroller 65 can trigger 414 an alert to a physician, the patient, and/or to any number of other people indicating the likely problem(s) and/or the suggested corrective action(s). Alternatively, if the measured pressure does not vary from the baseline pressure, then pressure within the internal portion 10a is normal and no alert need be triggered 414, although in some embodiments, notice of a normal pressure reading can be provided.

The microcontroller 65 can trigger 414 an alert in a variety of ways. The microcontroller 65 can trigger an alert by, for example, communicating a signal to an external device (e.g., a patient feedback mechanism such as an external pack worn on the patient's wrist, belt, etc. or otherwise carried by or accessible to the patient, a mechanism included in the implanted portion 10a (e.g., in the port 30), the control box 90, etc.) indicating the likely problem(s) and/or the suggested corrective action(s) and triggering notice of the alert. An alert can include any one or more of the following: an e-mail, a phone call, a text message, an audible signal, a mechanical vibration, a light or other visual display, a tactile display, a message displayed on an external device, or any other type of alert. Different alert patterns (e.g., varying audio signals, varying vibration patterns, etc.) can be used to signify different conditions. Two or more alerts can be provided to multiple people under similar conditions, although alerts may not be provided simultaneously to multiple people or be provided to anyone at all. The type of an alert can also vary relative to the problem detected and/or to the recipient of the alert. For example, with respect to alerts for physicians or other medical personnel, such alerts may be limited to those provided upon an event requiring medical advice or intervention (e.g., undesirable band pressure, undesirable patient eating habits, etc.) or indicating that some component of the internal portion 10a has structurally failed (e.g., a kink in catheter 50, a leak in the band 20, etc.). With respect to alerts for patients, such alerts may be limited to patient activity such as those provided upon an indication that the patient is eating too infrequently, eating too quickly, or if the patient's bite sizes are too big. A variety of other conditions under which alerts can be directed to a physician, a patient, and/or another person will be understood by those skilled in the art. Other suitable processes for detecting alert triggers, as well as ways in which the alerts can be provided and the timing of providing the alerts (e.g., immediately, on a regular schedule such as every day or every hour, after detection of a certain milestone or pattern of data, etc.), will be appreciated by those skilled in the art.

Figure 10:
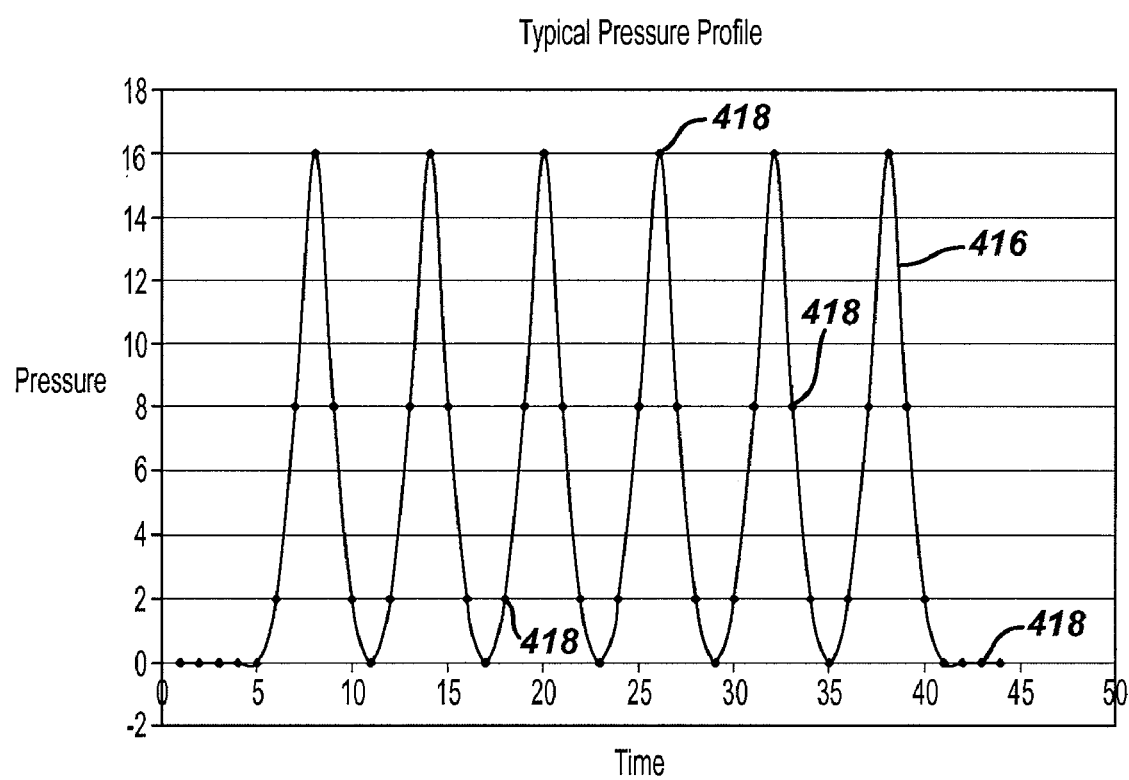
FIG. 10 is a graphical representation of an embodiment of a typical pressure measurement from the pressure sensor of FIG. 5.

One embodiment of the processor's analysis 406 of the pressure data is shown in FIG. 9. As non-limiting examples only, FIG. 10 shows an example sequence of baseline or typical pressure data 416 including a plurality of baseline data values 418 (not all data values labeled), and FIGS. 11-21 show example sequences of gathered or sensed pressure data 420 including a plurality of sensed data values 422 (not all data values labeled) that the microcontroller 65 can receive from the sensor 62. The pressure values and times shown in FIGS. 10-21 are examples only; the pressure values can include any values or ranges of values over any period of time. A person skilled in the art will appreciate that the baseline data values 418 can include sensed data values 422 previously gathered by the sensor 62, e.g., four hours ago, yesterday, last week, last month, etc. Furthermore, the baseline data 416 for a patient can change over time, e.g., as the patient gains or loses weight. Although analysis 406 of the pressure data is discussed with relation to the elements included in FIGS. 1A-7 and the pressure data included in FIGS. 10-21, a person skilled in the art will also appreciate that data analysis as described herein can be performed using any pressure data and these or similar elements.

Generally, the microcontroller 65 can follow a pre-programmed algorithm to analyze 406 gathered pressure data 420. The microcontroller 65 can determine if the sensed pressure data 420 varies from the baseline pressure data 416 and therefore reflects an atypical pressure condition such as overpressure, underpressure, unexpected pressure pulse duration, or unexpected pressure pulse frequency. If the sensed pressure data 420 does not vary from the baseline pressure data 416, then the data indicates 472 that the sensed pressure data 420 is normal.

Figure 11:
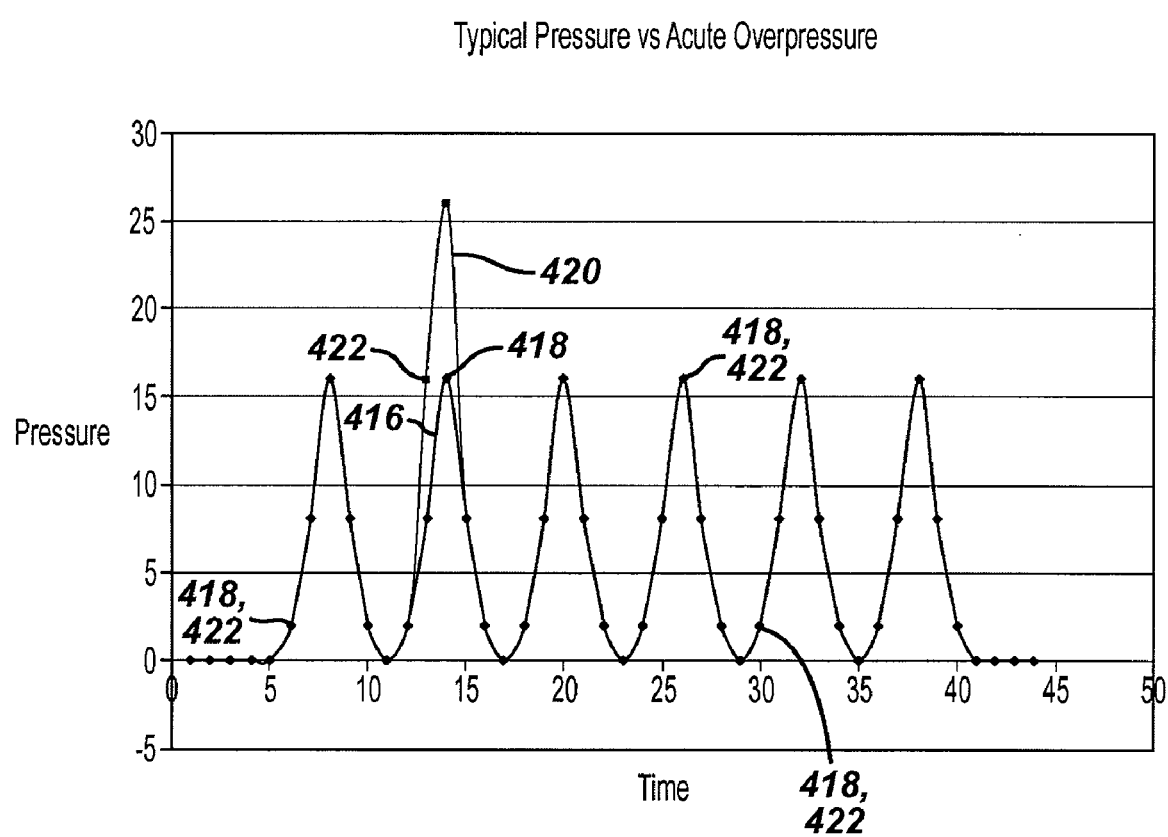
FIG. 11 is a graphical representation of an embodiment of acute overpressure and the typical pressure measurement of FIG. 10.
Figure 12:
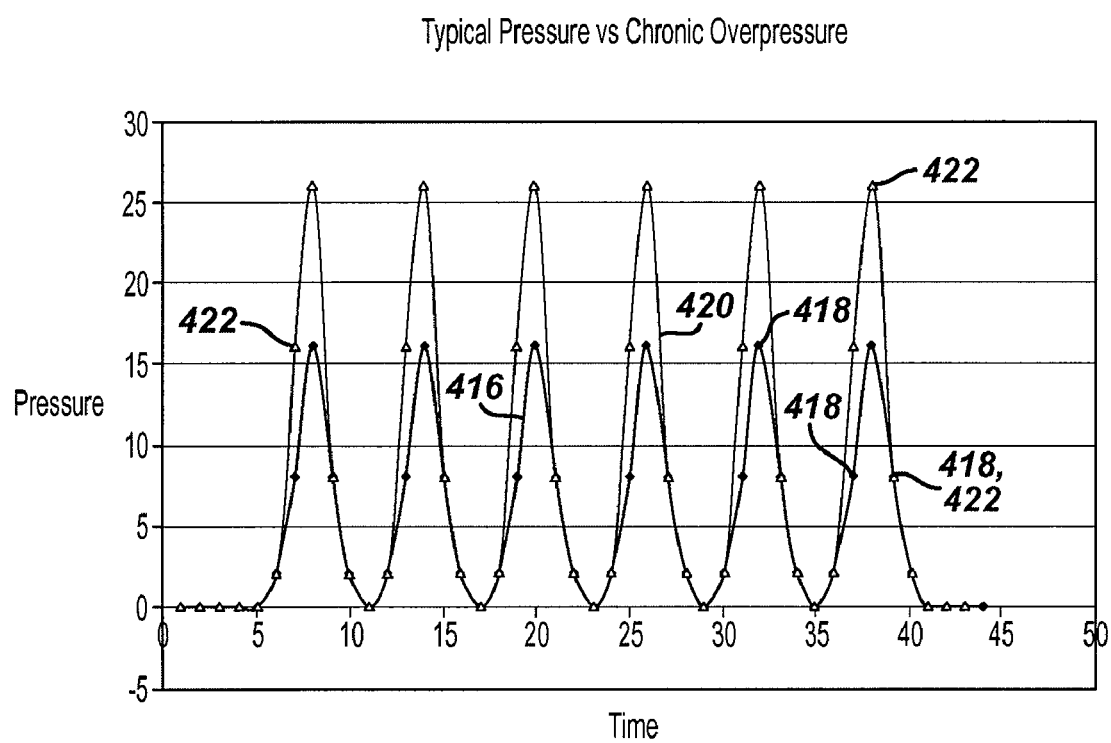
FIG. 12 is a graphical representation of an embodiment of chronic overpressure and the typical pressure measurement of FIG. 10.
Figure 13:
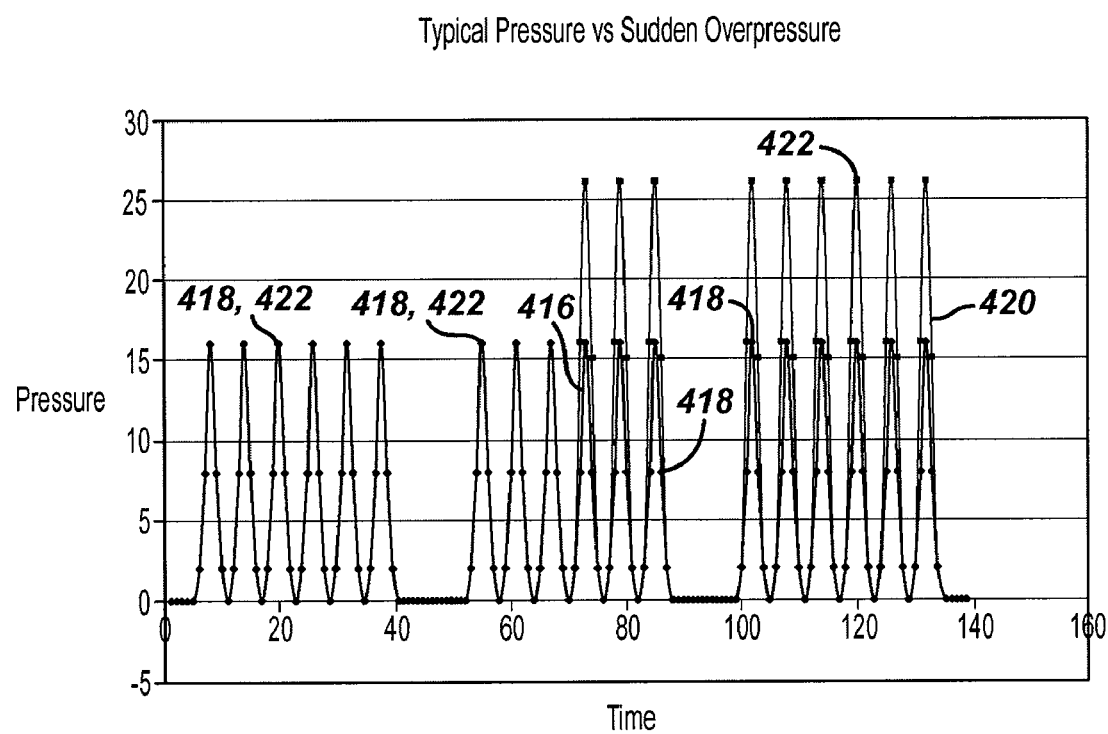
FIG. 13 is a graphical representation of an embodiment of sudden overpressure and the typical pressure measurement of FIG. 10.

More specifically, in analyzing 406 gathered pressure data 420, the microcontroller 65 can determine 424 if the sensed pressure data 420 is above the baseline pressure data 416 for any time(s) over a range of time. Although the microcontroller 65 first analyzes for overpressure in this embodiment, the microcontroller 65 can analyze gathered pressure data for atypical pressure conditions in any order, not limited to the order discussed with reference to FIG. 9. If the microcontroller 65 detects overpressure in the sensed pressure data 420, the microcontroller 65 can determine 426 if the overpressure exists as an acute instance, e.g., an isolated spike in pressure. An example of sensed pressure data 420 including acute overpressure is illustrated in FIG. 11, where acute overpressure exists between time 11 and time 14, with the sensed pressure 420 otherwise substantially equaling the baseline pressure 416 during times 1-11 and times 14-44. If acute overpressure exists, then the gathered pressure data 420 likely indicates 428 excessive food bolus size or vomiting, with respective suggested corrective actions of the patient chewing food more thoroughly and the patient adjusting eating habits. As with all likely indicators and suggested corrective actions discussed herein, these indicators and suggested corrective actions are provided as examples only, and these or other indicators and corrective actions can be programmed into the algorithm used by the microprocessor 65. If the overpressure is not acute, then the microcontroller 65 can determine 430 if the overpressure is chronic, e.g., persists over the analyzed range of time. If so, as shown in FIG. 12, then the gathered pressure data 420 likely indicates 432 that the band 20 is too tight or that the patient gained weight, with a suggested corrective action of band adjustment in either case. If overpressure exists but it is not acute or chronic, then the overpressure likely indicates 434 a sudden increase in pressure over the expected baseline that subsequently persists, such as shown in FIG. 13 where sudden overpressure starts at time 70. Sudden overpressure likely indicates an internal problem, such as a fill tube kink, a wrinkle in the band 20, or a shift in tissue proximate to the band 20, suggesting a physician's visit as a corrective action for patient inspection and likely band adjustment.

Figure 14:
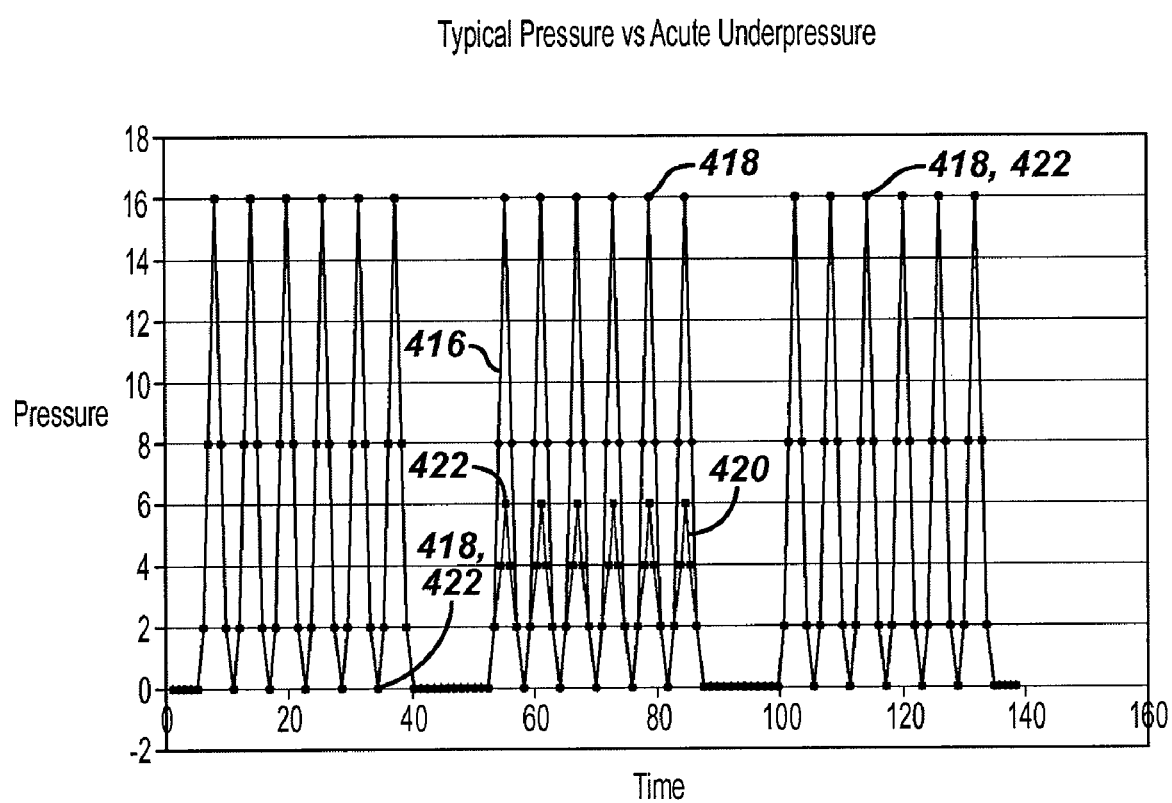
FIG. 14 is a graphical representation of an embodiment of acute underpressure and the typical pressure measurement of FIG. 10.
Figure 15:
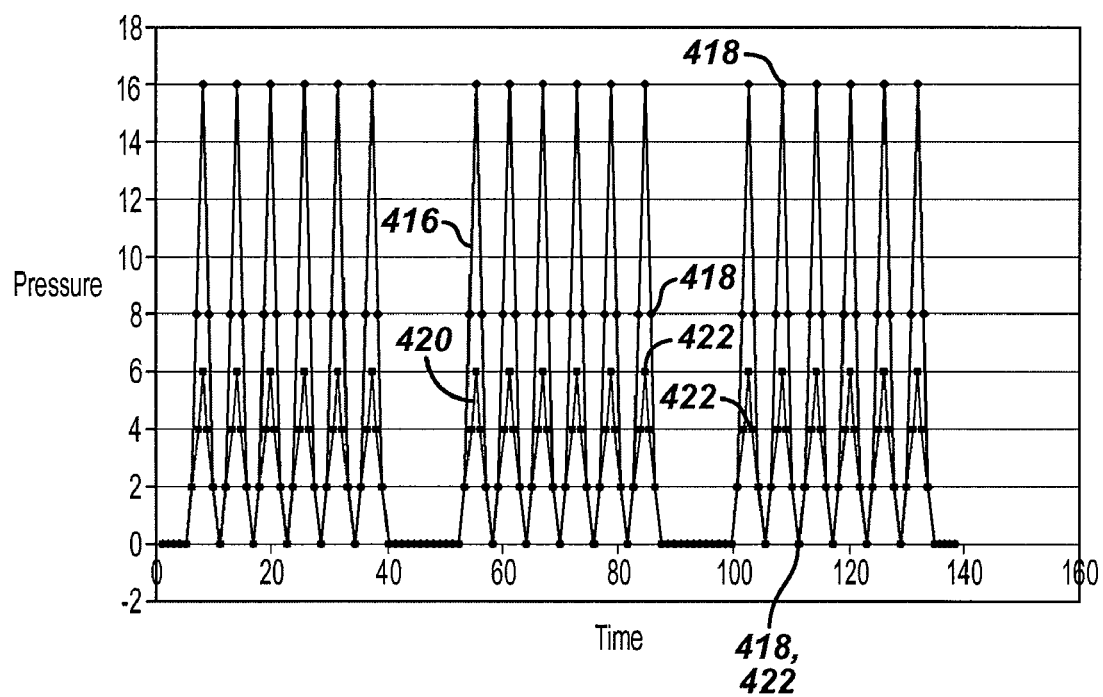
FIG. 15 is a graphical representation of an embodiment of chronic underpressure and the typical pressure measurement of FIG. 10.
Figure 16:
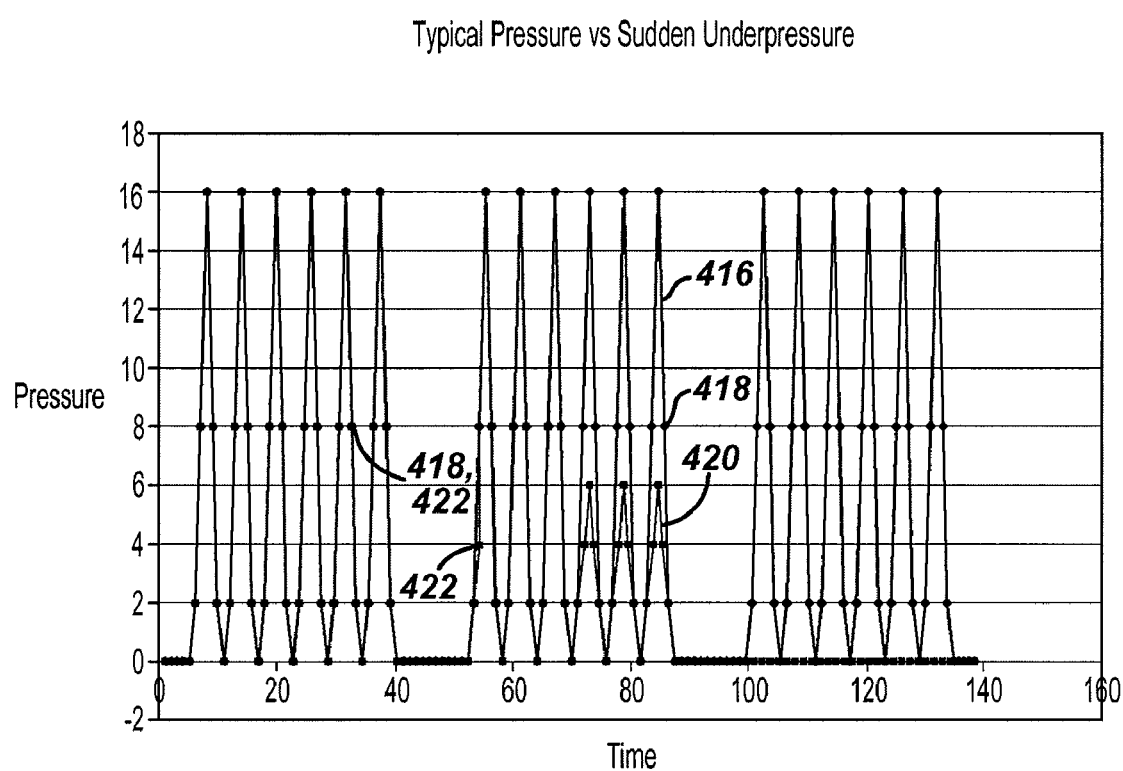
FIG. 16 is a graphical representation of an embodiment of sudden underpressure and the typical pressure measurement of FIG. 10.

The microcontroller 65 can also determine 436 if the sensed pressure data 420 is below the baseline pressure data 416 for any time(s) over a range of time. If the microcontroller 65 detects underpressure in the sensed pressure data 420, the microcontroller 65 can determine 438 if the underpressure exists an acute instance, e.g., an isolated drop in pressure. An example of sensed pressure data 420 including acute underpressure is illustrated in FIG. 14, where acute underpressure exists between time 52 and time 87, with the sensed pressure 420 otherwise substantially equaling the baseline pressure 416. If acute underpressure exists, then the gathered pressure data 420 likely indicates 440 patient consumption of liquid calories having a suggested corrective action of the patient adjusting diet, e.g., increasing consumption of solid food. If the underpressure is not acute, then the microcontroller 65 can determine 442 if the underpressure is chronic. If so, as shown in FIG. 15, then the gathered pressure data 420 likely indicates 444 that the band 20 is too loose or that the patient lost weight, with a suggested corrective action of band adjustment in either case. If underpressure exists but it is not acute or chronic, then the underpressure likely indicates 446 a sudden decrease in pressure under the expected baseline that subsequently persists, such as shown in FIG. 16 where sudden underpressure starts at time 70. Sudden underpressure likely indicates an internal problem, such as a leak in the band 20, suggesting a physician's visit as a corrective action for patient inspection and likely band adjustment.

Figure 17:
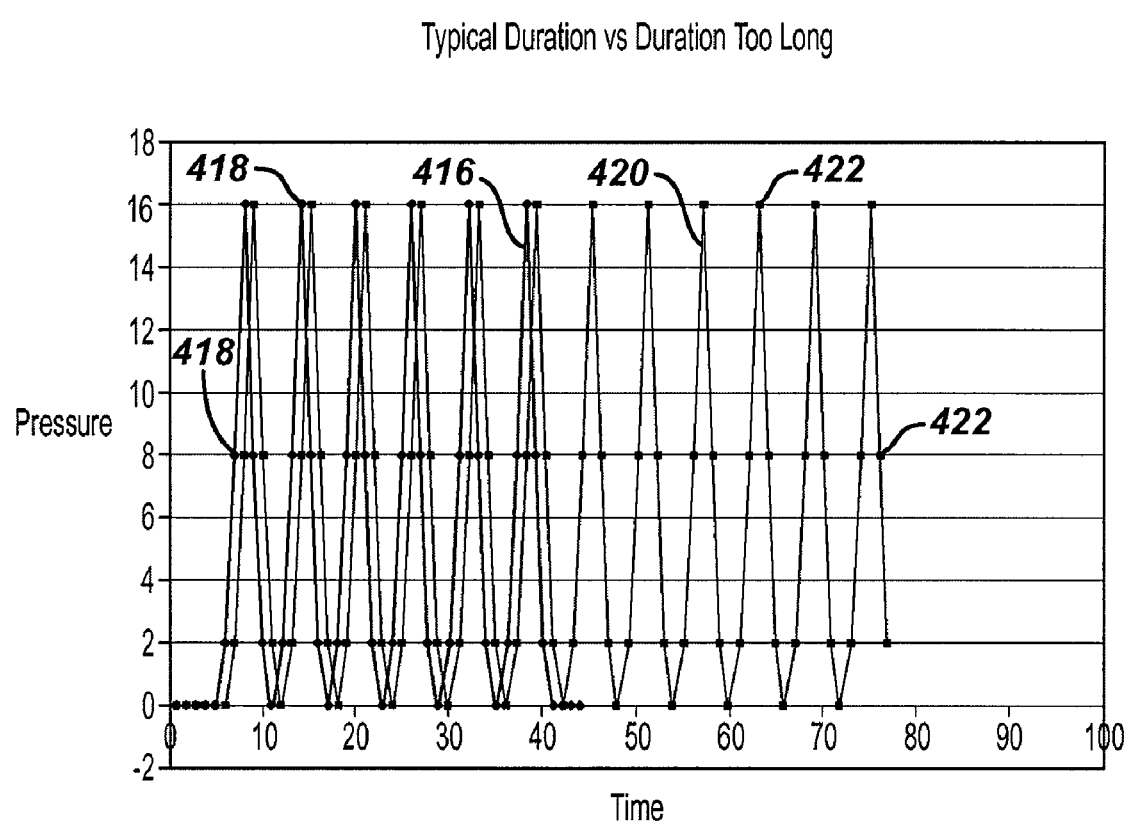
FIG. 17 is a graphical representation of an embodiment of pressure of long duration and the typical pressure measurement of FIG. 10.
Figure 18:
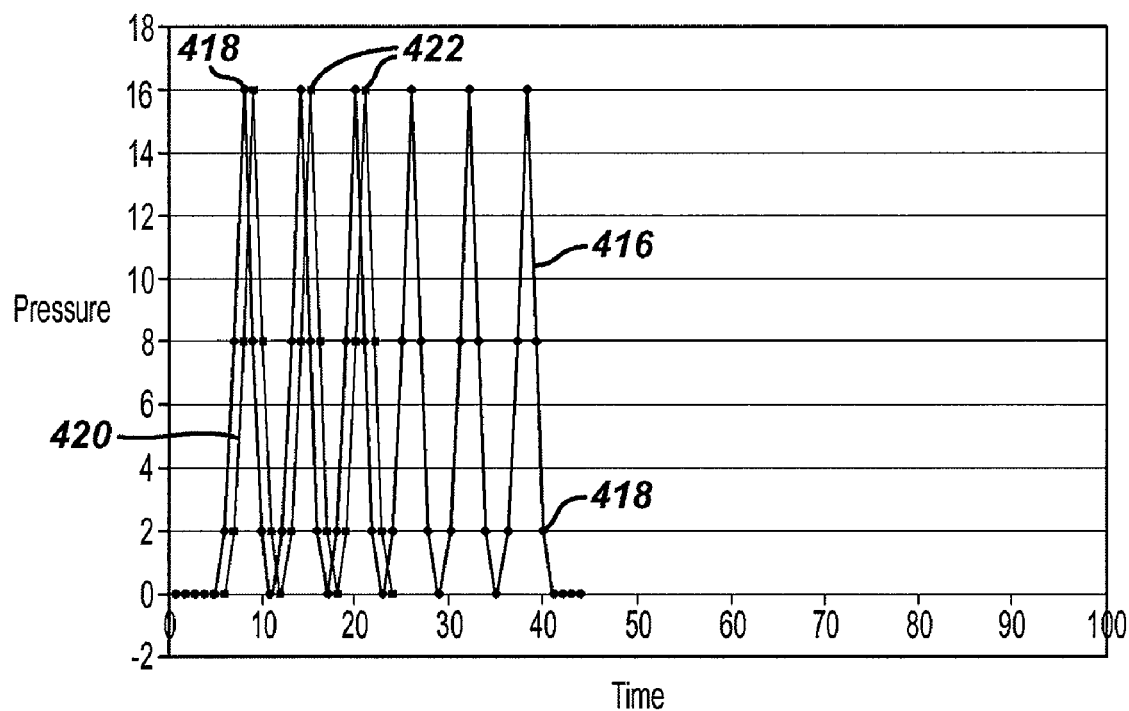
FIG. 18 is a graphical representation of an embodiment of pressure of short duration and the typical pressure measurement of FIG. 10.

The microcontroller 65 can also determine 448 if a duration of sensed peristaltic pulses varies from the baseline. If the microcontroller 65 detects an unexpected duration of peristaltic pulses, the microcontroller 65 can determine 450 if the duration of peristaltic pulses is too long, e.g., if the duration is excessive as indicated by the presence of sensed positive pressure data values 422 beyond an expected end time of typical pressure data 416. An example of excessively long pressure data 420 is illustrated in FIG. 17, where sensed peristaltic pulses continue beyond the baseline data 416 after time 42. If the duration of peristaltic pulses is too long, then the gathered pressure data 420 likely indicates 452 improper food quality (e.g., not enough solid foods consumed, consumption of pureed food, etc.) or improper eating habits, with respective suggested corrective actions including the patient adjusting diet (e.g., increasing consumption of solid food) and adjusting eating habits (e.g., eating for a shorter period of time). If the duration of peristaltic pulses is too short, such as shown in FIG. 18, then the gathered pressure data 420 likely indicates 454 improper eating habits with a suggested corrective action including the patient adjusting eating habits (e.g., eating for a longer period of time).

Figure 19:
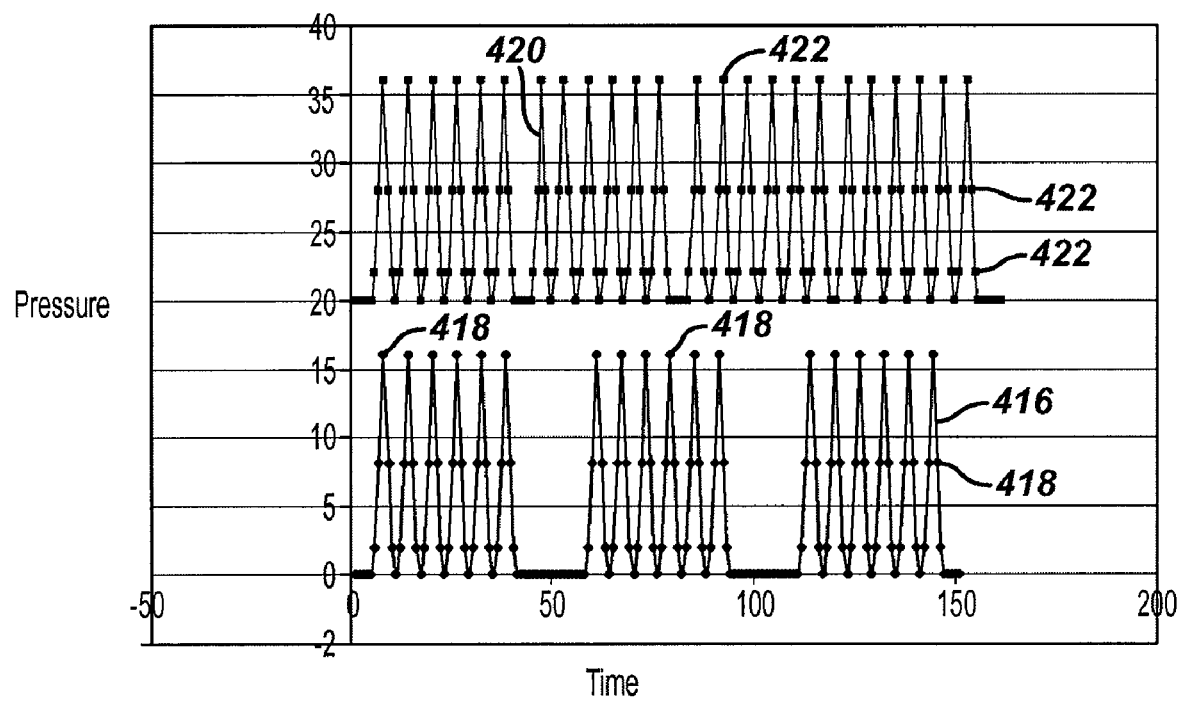
FIG. 19 is a graphical representation of an embodiment of too frequent pressure and the typical pressure measurement of FIG. 10.
Figure 20:
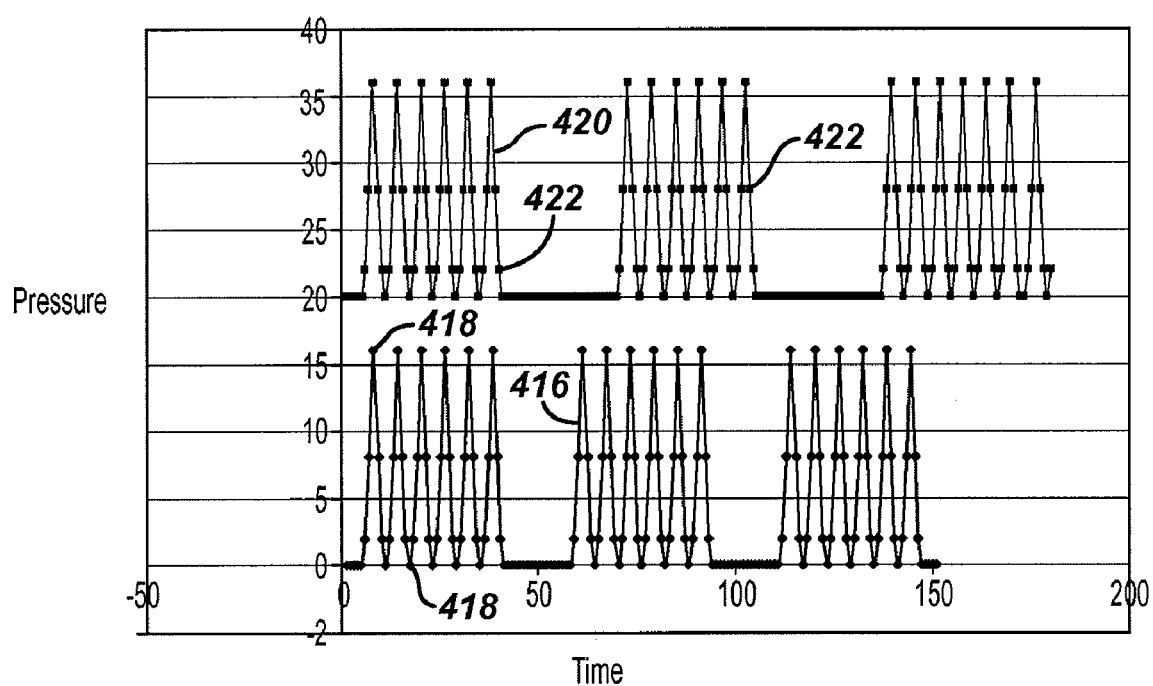
FIG. 20 is a graphical representation of an embodiment of too infrequent pressure and the typical pressure measurement of FIG. 10.
Figure 21:
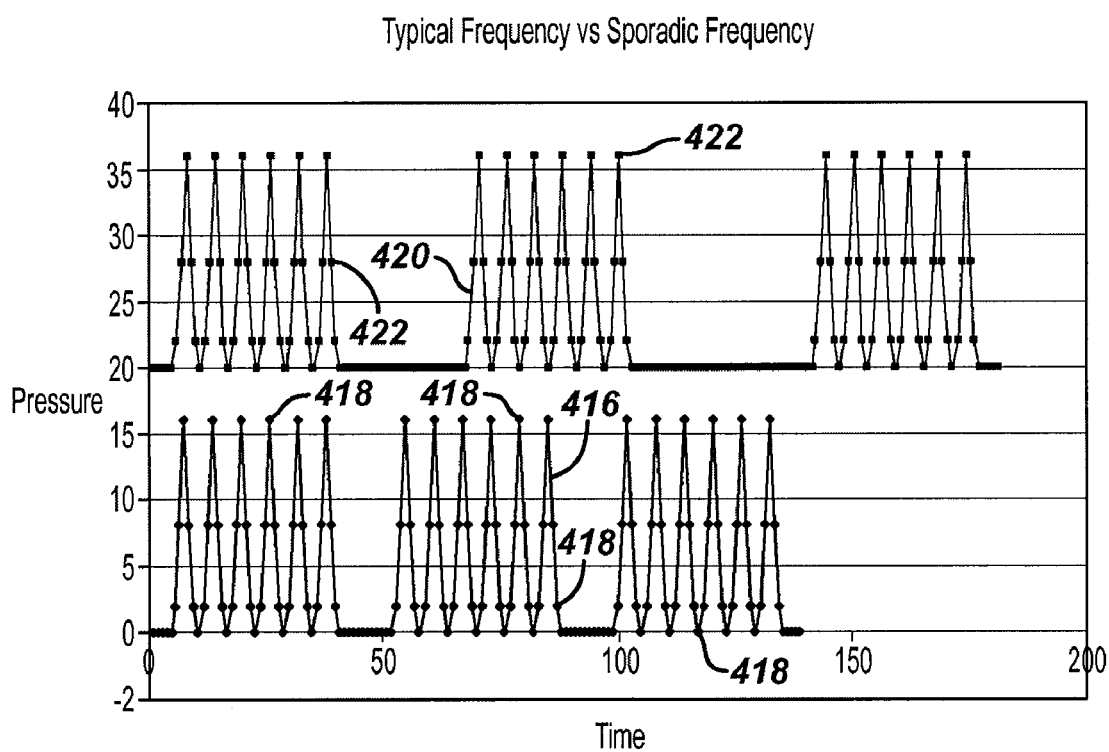
FIG. 21 is a graphical representation of an embodiment of sporadic pressure and the typical pressure measurement of FIG. 10.

The microcontroller 65 can also determine 456 if the sensed data values 420 have a frequency that varies from the baseline data values 418, e.g., if the sensed data values 420 are spaced irregularly over time compared to the baseline data values 418. If the microcontroller 65 detects an unexpected frequency of sensed data values 422, the microcontroller 65 can determine 458 if the sensed pressure data values 422 occur too frequently. An example of too frequent pressure data 420 is illustrated in FIG. 19. If the frequency of the sensed pressure data 420 is too great, then the sensed pressure data 420 likely indicates 460 that the patient is eating too frequently or eating too much during meals, with a suggested corrective action in either case including the patient adjusting eating habits (e.g., eating less often, eating less food per meal, etc.). If the data frequency is not excessive, then the microcontroller 65 can determine 462 if the sensed pressure data values 422 occur too infrequently. If so, as shown in FIG. 20, then the gathered pressure data 420 likely indicates 464 that the patient is eating too infrequently or not eating enough during meals, with a suggested corrective action in either case including the patient adjusting eating habits (e.g., eating more often, eating more food per meal, etc.). If the frequency of sensed data values 422 is neither too high or too low, the microprocessor 65 can determine 466 if the sensed pressure data values 422 occur sporadically, e.g., at an irregular frequency. If the sensed pressure data 420 is irregular, then the gathered pressure data 420 likely indicates 468 that the patient is eating sporadically, with a suggested corrective action of the patient adjusting eating habits (e.g., eating at regular intervals). If frequency of sensed data values 422 is atypical but not too high, too low, or irregular, then the atypical frequency likely indicates 470 a sudden change in frequency of eating, such as shown in FIG. 21. Such a sudden frequency change likely indicates an internal problem (e.g., the band 20 being too tight or too loose) or a change in patient weight (gain or loss), all of which suggest a physician's visit as a corrective action for patient inspection and likely band adjustment.

In analyzing 406 the sensed pressure data 420, the microcontroller 65 can discard sensed pressure data 420 related to one or more physiologic events and not determine such data to indicate a problem despite it otherwise appearing inconsistent with the baseline data 420. Non-limiting examples of physiologic events include supra events (e.g., coughing, vomiting, retching, etc.) and normal events (heartbeats, etc.). Physiologic events can result in measured pressure data that significantly differs from an expected level in magnitude, duration, occurrence (e.g., an unexpected time of day, such as midnight), and/or frequency from established patterns of patient eating. The microcontroller 65 can determine to retain gathered pressure data by analyzing the data for such a significant difference, such as by determining if any of the obtained pressure data includes a value above a pre-programmed threshold value typically not exceeded except in response to a physiologic event. The microcontroller 65 can also or instead determine if any of the obtained pressure data includes a value within a defined range of pressure values. Depending on the defined range, the microcontroller 65 can determine to discard data within the range (e.g., if the range reflects pressure readings of an expected frequency and magnitude caused by a normal event) or to retain data within the range (e.g., if the range includes any positive pressure values up to a threshold value typically not exceeded except by a physiologic event).

Figure 22:
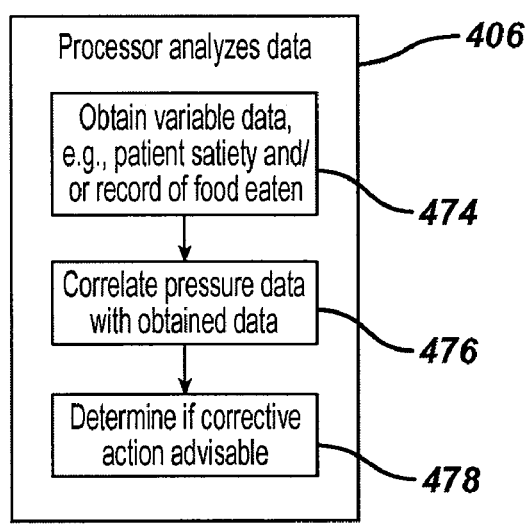
FIG. 22 is a flow diagram showing another expanded embodiment of the data analysis protocol of FIG. 8.
Figure 23:
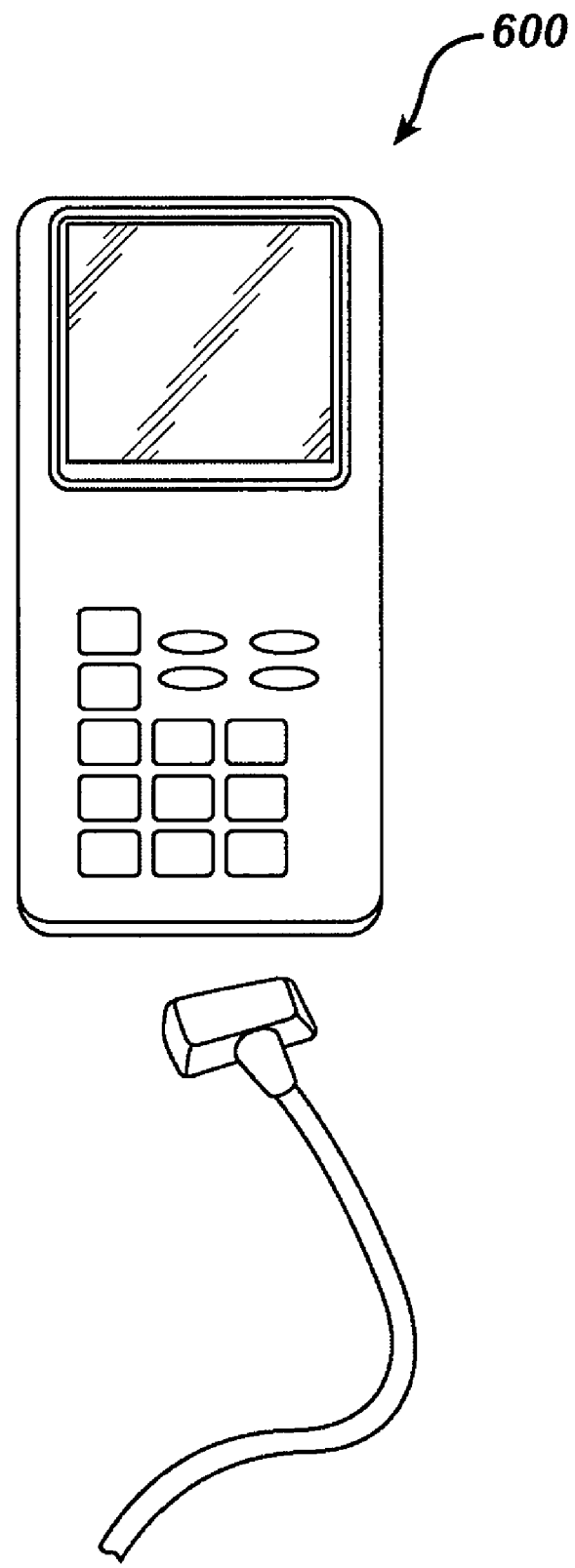
FIG. 23 is a perspective view of a display device.

The microcontroller 65 can in addition to or instead of analyzing pressure data for an atypical pressure condition, the microcontroller 65 can consider one or more variables in addition to pressure in analyzing 406 gathered pressure data. One embodiment of an analysis process considering such variables is shown in FIG. 22. In analyzing 406 the sensed pressure data 420, the microcontroller 65 can obtain 476 variable data related to the patient, such as a record of patient satiety levels or a record of food eaten by the patient. The microcontroller 65 can obtain 476 variable data in a variety of ways. For example, the patient can enter information about their levels of satiety one or more times a day (e.g., at regular intervals, a certain amount of time before or after a meal, etc.) into an input device such as a wired or wireless hand held display device 600, one embodiment of which is shown in FIG. 23. The patient can enter a number corresponding to their current level of satiety, e.g., based on a scale using one for hungry, three for satiated, five for content, seven for full, and nine for overstuffed. As another example, the patient can enter information about the types of food eaten at a certain time (e.g., a particular time or a time of day) into an input device, such the hand held device 600. The patient can enter a number corresponding to a particular food type (e.g., one for solid, two for liquid, etc.), select a food type from a provided list of specific foods or food types, take a picture of food to be eaten and upload it to the input device, etc.

Over the course of any number of input cycles (e.g., daily, every twelve hours, after a final input of the day as indicated by the patient or by a standard schedule, every week, etc.), the microcontroller 65 can correlate 476 sensed pressure data 420 for a certain time or for a range of time with input variable data corresponding to that certain time or range of time. Such correlation can involve the microcontroller 65 "learning" a baseline correlation between a variable input and pressure data. Similar to the analysis described above, the microcontroller 65 can determine 478 if a corrective action is advisable, in which case the microcontroller 65 can trigger 414 an alert as described above. For example, the microcontroller 65 can trigger 414 an alert indicating that the patient has had enough to eat based on gathered pressure data 420 (e.g., real time gathered pressure data) substantially equaling previous pressure data corresponding to a certain satiety level input by the patient. As another example, the microcontroller 65 can trigger 414 an alert indicating that a possible problem may exist, so a physician should consult with the patient because input satiety levels vary for substantially equal pressure measurements over the course of a certain number of input cycles. As still another example, solid foods such as breads and meats, as opposed to liquids, typically result in pressure data 420 having higher amplitude peaks, more peaks, and a longer duration of each peak as the patient's body works to move the consumed food through the restriction caused by the band 20. The microprocessor 65 can "learn" to recognize such a "food fingerprint" based on input food types and measured pressure levels and, for subsequently measured pressure data substantially the same, determine a suggested corrective action based on the previous (now baseline) data. As such, the microcontroller 65 can trigger 414 an alert suggesting a patient eating habit corrective action if gathered pressure data 420 substantially equals previous pressure measurements corresponding to an input record of food that can be modified (e.g., chew food more, eat more solid foods, etc.).

As mentioned above, data gathered by the sensor 62 (analyzed by the microcontroller 65 or not) can be uploaded to an external unit such as the control box 90 (and/or other units located local or remote to the patient) to allow a person to physically evaluate and/or the control box 90 to electronically evaluate the patient's treatment and/or performance of elements included in the internal portion 10*a* over a designated time period. In some embodiments, a processor included in the external portion 10*b* of the restriction system 10 (e.g., the microprocessor 136) can receive 402, store 404, and/or analyze 406 the data gathered by the sensor 62. Such an external processor can also trigger 414 an alert, if necessary.

Data stored in the implantable memory 162 can be communicated to an external device in a variety of ways. In some embodiments, the microcontroller 65 continually communicates data (via the telemetry transceiver 158 and the secondary coil 114), and the data is only received when an appropriate receiving device, such as the antenna (the primary TET coil 130 and the telemetry coil 144), moves into sufficient proximity of it. In some embodiments, a download of data from the memory 162 can be triggered when an external device (e.g., the reading device 70) telemetrically provides power to the sensor housing, e.g., when the external device is moved in proximity of the sensor housing 60. The external device can be mobile (e.g., a wand or hand-held unit that can be waved or otherwise placed in proximity of the sensor housing 60) or stationary (e.g., a bedside, desk-mounted, or car-mounted box that the patient can move near). Telemetrically providing power to the sensor housing 60 can save power in the internal portion 10*a* because download communication power is supplied by the external portion 10*b*.

The external device can be configured to store data received from the sensor housing 60. The external device can be further configured communicate the data to another external device, such as a base unit at a location remote from the patient. The external device (typically, the control box 90 or other device having a capability to display or otherwise provide an alert such as the hand held display device 600) can detect if the internal portion 10*a* communicated a signal indicating an alert and provide an alert as appropriate (e.g., displaying a warning notice, sending an e-mail message, etc.).

Figure 24:
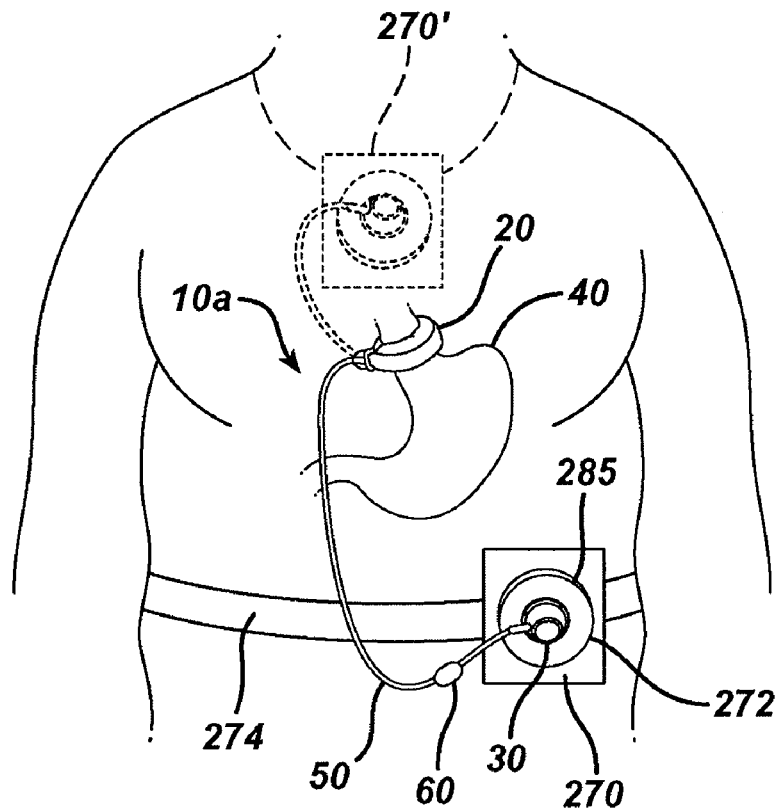
FIG. 24 is a schematic diagram of an embodiment of a data logger for recording pressure measurements related to the food intake restriction device of FIG. 1A.

FIG. 24 illustrates an embodiment of an external device, a data logger 270, that can include a processor that can analyze pressure measurements over a period of time. The data logger 270 can function as a removably attached data reading device 70, mentioned above. In this example, the data logger 270 includes a wearable pack external to the patient worn on a belt 274 and positioned over or within communication range of the region under which the sensor housing 60 is implanted within the patient. Alternatively, the data logger 270 can be worn about the patient's neck, as shown by a device 270', such as when the injection port 30 is implanted on the patient's sternum and the port 30 includes the pressure sensing device. In another embodiment, the data logger 270 is also implanted within the patient.

As shown in FIG. 24, the data logger 270 includes a TET coil 285 and a telemetry coil 272 which can be worn by the patient so as to lie adjacent to the internal portion 10*a*. The TET coil 285 can provide power to the implant, while the telemetry coil 272 can interrogate the implant and can receive data signals, including pressure measurements, through the secondary telemetry coil 114 in the implanted portion 10*a*. In another embodiment, the TET coil 285 and the telemetry coil 272 can be consolidated into a single coil and alternate between TET and telemetry functions at any suitable rate for any suitable durations.

The pressure within the band 20 can be repeatedly sensed and transmitted to the data logger 270 at an update rate sufficient to measure peristaltic pulses against the band 20. Typically, this update rate is in the range of 5-20 pressure measurements per second, but any update range can be used. The data logger 270 is typically worn during waking periods to record pressure variations during the patient's meals and daily routines. At the end of the day, or another set time period, the data logger 270 can be removed and recorded pressure data downloaded to the external memory 138. The pressure history can be uploaded from the memory 138 to a remote unit over one or more communication links during a subsequent communication session. Alternatively, pressure data can be directly uploaded from the data logger 270 to a remote unit using one or more communication links. A communication link can include any single or combination of two or more data transmission media including web-based systems utilizing high-speed cable or dial-up connections, public telephone lines, wireless RF networks, Bluetooth, ultrawideband (UWB), satellite, T1 lines or any other type of communication media suitable for transmitting data between remote locations. The data logger 270 can be configured to dock into another device, e.g., a docking station, that is configured to receive data communication from the data logger 270 and transmit the received data to a remote unit.

Figure 25:
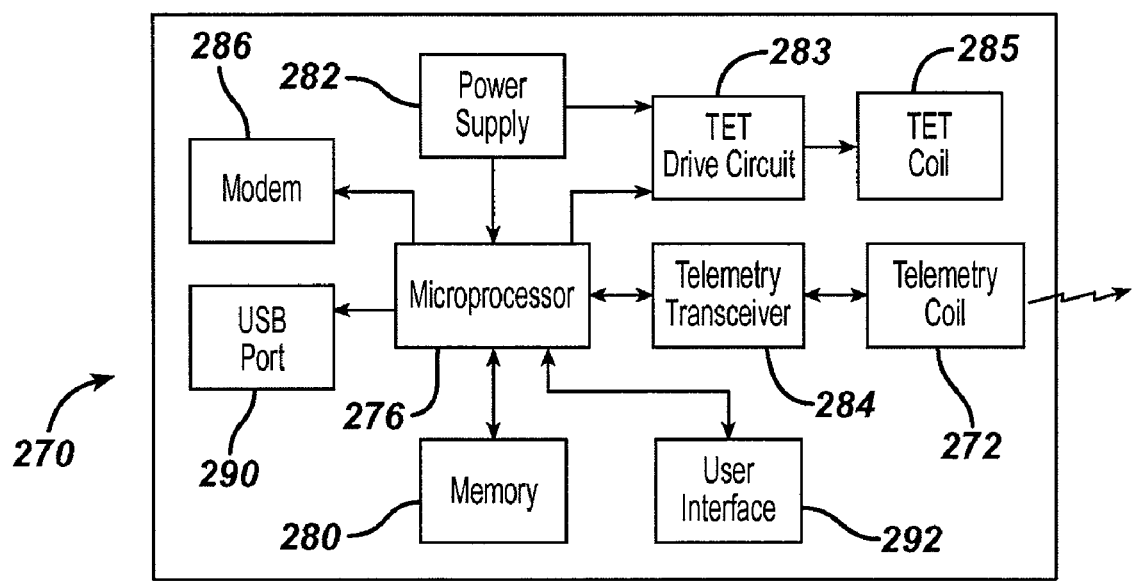
FIG. 25 is a block diagram showing an embodiment of components of the data logger of FIG. 24.

FIG. 25 shows the data logger 270 in greater detail. As shown in FIG. 25, the data logger 270 includes a microprocessor 276 for performing analysis as described above and/or for controlling telemetry communications with the internal portion 10a. The microprocessor 276 is connected to a memory 280 for, at least, storing pressure measurements from the internal portion 10a. In this embodiment, the memory 280 includes forty MB of Non-Volatile EEPROM or FLASH memory and is configured to store about one hundred hours of time stamped pressure data, but any other type of storage can be used, and the memory 280 can store any amount of and any type of data. By way of non-limiting example, any other type of volatile memory or any type of non-volatile memory can be used. While the data logger 270 in this example is operational, pressure can be read and stored in the memory 280 at a designated data rate controlled by the microprocessor 276.

The microprocessor 276 can be energized by a power supply 282. In one embodiment, the power supply 282 includes a rechargeable cell (not shown), such as a rechargeable battery. In some embodiments, the rechargeable cell is removable and can be recharged using a recharging unit and replaced with another rechargeable cell while the spent cell is recharging. In other embodiments, the rechargeable cell can be recharged by plugging a recharging adapter into the data logger 270 and a wall unit. In yet another embodiment, the rechargeable cell can be recharged wirelessly by a wireless recharging unit. In still another embodiment, the power supply 282 includes an ultra capacitor, which can also be recharged. Of course, any other type of power supply can be used.

To record pressure, the microprocessor 276 can initially transmit a power signal to the internal portion 10a via a TET drive circuit 283 and the TET coil 285. After transmitting the power signal, the microprocessor 276 can transmit an interrogation signal to the internal portion 10a via a telemetry transceiver 284 and the telemetry coil 272. The interrogation signal can be intercepted by the telemetry coil 114 and transmitted to the microcontroller 65. The microcontroller 65 can send a responsive, optionally-temperature-adjusted pressure reading from the sensor 62 via the transceiver 158 and the secondary telemetry coil 114. The pressure reading can be received through the telemetry coil 272 and directed by the transceiver 284 to the microprocessor 276. The microprocessor 276 can store the pressure measurement in its associated memory 280 and initiate the next interrogation request. If the microprocessor 65 can trigger an alert (in addition to or instead of the microprocessor 276 and/or any other processor), the microprocessor 276 can respond to an alert identified by the microcontroller 65, such as with a visual alert (e.g., flashing a light on the data logger 270, displaying a message on a user interface 292, etc.) and/or with an audible alert. The user interface 292 can include any number and types of features, including but not limited to a speaker, an LED, an LCD display, an on/off switch, etc. In some embodiments, the user interface 292 is configured to provide only output to the patient and does not permit the patient to provide input to the data logger 270. The user interface 292 thus includes an LED, which when lit shows that the power supply 282 is sufficiently charged and another, differently colored LED to show when the power supply 282 needs to be recharged, although such power indicators can be shown using any type and any combination of indicators such as one light that illuminates upon low power charge, an audible alert, an email alert, etc. In other embodiments, the user interface 292 can allow the patient to provide input to the data logger 270 and can accordingly include any suitable components and features.

When finished measuring and recording pressure, the data logger 270 can be removed from the patient and/or from the belt 274 and the recorded pressure data downloaded to the control box 90 (and/or to any other external device). The data logger 270 can include a modem 286 for transmitting sensed pressure data directly to a remote base unit using a communication link. For example, the patient can connect the modem 286 to a telephone line (or other communication link), dial the physician's modem (if necessary), and select a "send" button on the user interface 292. Once connected, the microprocessor 276 can transmit stored pressure history and/or pressure data analysis through the phone line to a processor included in the remote unit. Alternatively, the data logger 270 can include a USB port 290 for connecting the logger 270 to the control box 90. The logger USB port 290 can be connected to a USB port included on the control box 90 and the "send" switch activated to download pressure data to the memory 138 in the control box 90. After pressure data is downloaded, the data logger 270 can be turned off through the user interface 292 or reset and placed back on the patient and/or the belt 274 for continued pressure measurement.

Figure 26:
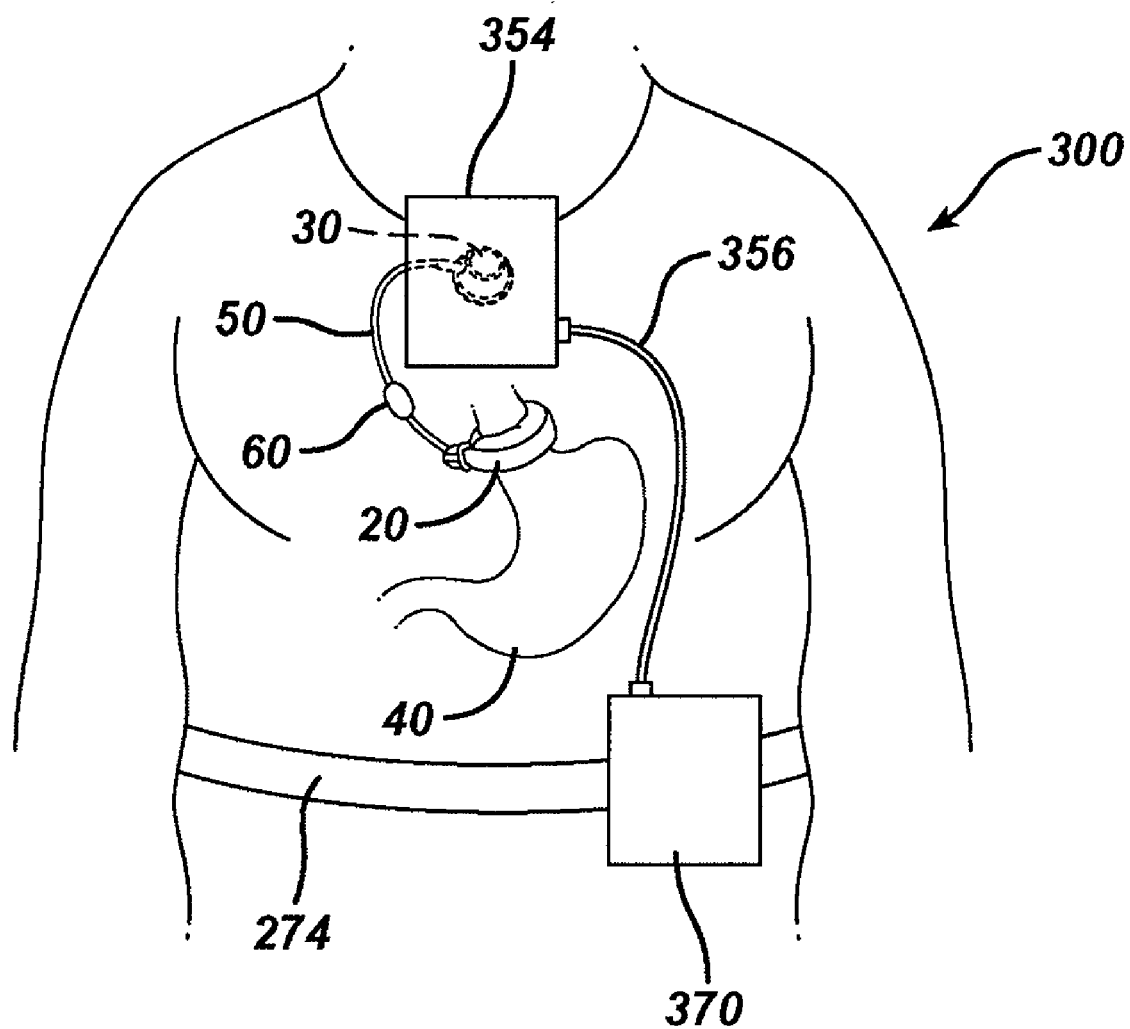
FIG. 26 is a schematic diagram of an embodiment of a data logging system for recording pressure measurements related to the food intake restriction device of FIG. 1A.

An alternate embodiment of a data logging system 300 is shown in FIG. 26. In this example, the data logging system 300 includes a coil head 354 and a data logger 370. The coil head 354 and the data logger 370 are in communication via a detachable cable 356. Any one or more suitable alternative communication links can be used in the place of the cable 356, including but not limited to a wireless transmitter/receiver system. In the illustrated embodiment, the coil head 354 is worn around the neck of the patient and is positioned generally over the injection port 30 and within communication range of the sensor housing 60. The data logger 370 is worn on the belt 274 about the patient's waist. Of course, these respective locations are merely exemplary, and either or both the coil head 354 and the data logger 370 can be positioned elsewhere. By way of non-limiting example, when the injection port 30 is implanted in the patient's abdomen, the coil head 354 can be worn on the belt 274. The coil head 354 and the data logger 370 are represented as simple blocks in FIG. 26 for illustrative purposes only, and either of the coil head 354 or the data logger 370 can be provided in a variety of shapes, sizes, and configurations.

Figure 27:
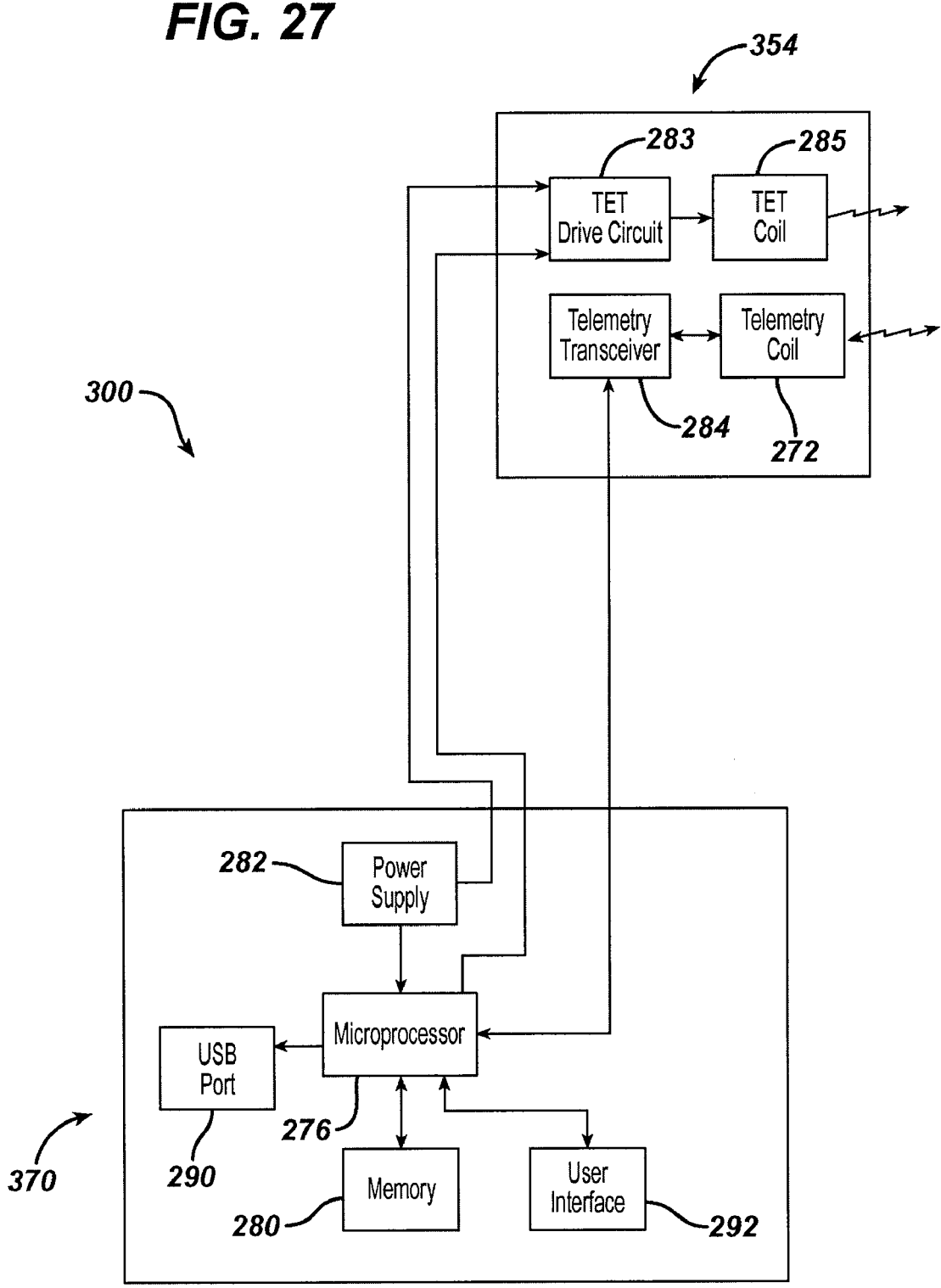
FIG. 27 is a is a block diagram showing an embodiment of components of the data logging system of FIG. 26.

Exemplary components of the data logging system 300 are shown in FIG. 27. As shown, the data logger 370 includes the microprocessor 276, the memory 280, the power supply 282, the USB port 290, and the user interface 292. The coil head 354 includes the TET drive circuit 283, the telemetry transceiver 284, the TET coil 285, and the telemetry coil 272. The TET drive circuit 283 is configured to receive power from the power supply 282 via the cable 356. The TET drive circuit 283 is further configured to receive signals from the microprocessor 276 via the cable 356. The telemetry transceiver 284 is configured to receive signals from the microprocessor 276 and transmit signals to the microprocessor 276, via the cable 356. In another embodiment, the telemetry transceiver 284 is configured to only transmit signals to the microprocessor 276. The above discussion of such components with reference to FIG. 25 can also be applied to the components shown in FIG. 27. In the embodiment illustrated in FIG. 27, the coil head 354 and the data logger 370 can be viewed as a separation of components including the data logger 270 (described above) into two physically separate units. It will be appreciated by a person skilled in the art that any of the components shown in FIG. 27, as well as their relationships, functions, etc., can be varied in any suitable way.

In the present example, the coil head 354 is configured similar to and functions in a manner similar to the antenna (the primary TET coil 130 and the telemetry coil 144) described above. The TET coil 285 of coil head 354 is configured to provide power to the injection port 30. Of course, to the extent that any other devices (e.g., a pump, etc.) are implanted in the patient that are configured to receive power from the TET coil 285, the TET coil 285 can also provide power to such devices. Power provided by the TET coil 285 can be provided to the TET coil 285 by and regulated by the TET drive circuit 285, which can itself receive power from the power supply 282 via the cable 356. Such power provided to the TET drive circuit 283 can be regulated by the microprocessor 276 via the cable 356. In addition, or in the alternative, the microprocessor 276 can regulate the manner in which the TET drive circuit 285 provides power to the TET coil 285. While the present example contemplates the use of RF signaling through the TET coil 285, any other type of powering technique, as well as alternative power communicators, can be used. Other suitable configurations and relationships between these components, as well as alternative ways in which they may operate, will be appreciated by those skilled in the art.

The telemetry coil 272 of the coil head 354 is configured to receive signals from the coil 114, including signals indicative of the pressure within the implanted band system (e.g., pressure of fluid within the injection port 30, within the catheter 50, and/or within the adjustable band 20, pressure obtained using the pressure sensor 62, etc.) and signals indicative of temperature. The telemetry coil 272 can also receive any other type of signal representing any other type of information from any other source. Signals received by the telemetry coil 272 can be communicated to the telemetry transceiver 284, which can communicate such signals to the microprocessor 276 via the cable 356. The telemetry transceiver 284 can perform any appropriate translation or processing of signals received from the telemetry coil 272 before communicating signals to the microprocessor 276. Other suitable configurations and relationships between these components, as well as alternative ways in which they may operate, will be appreciated by those skilled in the art. It will also be appreciated that components may be combined. By way of non-limiting example, the TET coil 285 and the telemetry coil 272 can be consolidated into a single coil and alternate between TET and telemetry functions at any suitable rate for any suitable durations. In addition, while the present example contemplates the use of RF signaling through the telemetry coil 272, it will be appreciated that any other type of communication technique (e.g., ultrasonic, magnetic, etc.), as well as alternative communicators other than a coil, can be used.

In one exemplary use, the patient wears the coil head 354 and the data logger 370 throughout the day to record pressure measurements in the memory 280. At night, the patient can decouple the data logger 370 from the coil head 354 and couple the data logger 370 with a docking station, e.g., the control box 90. While the data logger 370 and the control box 90 are coupled, the control box 90 can transmit data received from the data logger 370 to a remote unit. To the extent that the power supply 282 includes a rechargeable cell, the control box 90 can recharge the cell while the data logger 370 is coupled with the control box 90. However, a patient need not necessarily decouple the data logger 370 from the coil head 354 in order to couple the data logger 370 with the control box 90. Moreover, pressure measurements can be recorded in the memory 280 and/or analyzed by the microprocessor 276 during the night in addition to or as an alternative to recording and/or analyzing such measurements during the day, and pressure measurements can be recorded twenty-four hours a day. In that way, timing of pressure measurement taking, recordation, and analysis need not be limited to the daytime only.

As described above, the data logger 370 can receive, store, analyze, and communicate data relating to pressure within the restriction system. However, the data logger 370 can receive, store, analyze, and/or communicate a variety of other types of data. By way of non-limiting example, the data logger 370 can also receive, process, store, analyze, and/or communicate data relating to temperature, EKG measurements, eating frequency of the patient, the size of meals eaten by the patient, the amount of walking done by the patient, etc. It will therefore be appreciated by those skilled in the art that the data logger 370 can be configured to process received data to create additional data for communicating to the control box 90. For example, the data logger 370 can process pressure data obtained via the coil head 354 to create data indicative of the eating frequency of the patient. It will also be appreciated by those skilled in the art that the data logger 370 can include additional components to obtain non-pressure data. For example, the data logger 370 can include a pedometer or accelerometer (not shown) to obtain data relating to the amount of walking done by the patient. Data obtained by such additional components can be stored in the memory 280 and communicated to the control box 90 in a manner similar to pressure data. The data logger 370 can also include components for obtaining data to be factored in with internal pressure measurements to account for effects of various conditions on the pressure. For example, the data logger 370 can include a barometer for measuring atmospheric pressure. In some embodiments, the data logger 370 includes an inclinometer or similar device to determine the angle at which the patient is oriented (e.g., standing, lying down, etc.), which can be factored into pressure data to account for hydrostatic pressure effects caused by a patient's orientation. Alternatively, an inclinometer or other device for obtaining non-pressure data can be physically separate from the data logger 370 (e.g., implanted). Still other types of data, ways in which such data may be obtained, and ways in which such data may be used will be appreciated by those skilled in the art.

Figure 28:
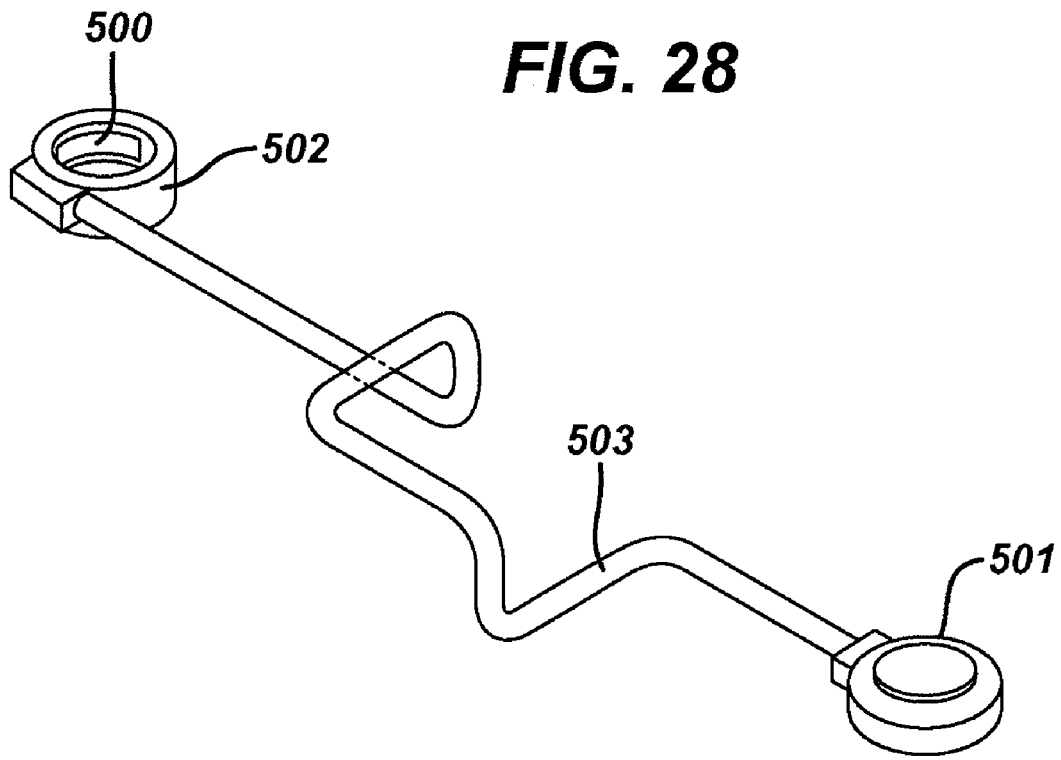
FIG. 28 is a perspective view of an embodiment of a gastric band system with a pressure sensor positioned along a catheter.

While embodiments described above include the use of the pressure sensor 62 within the sensor housing 60 removably joined to the catheter 50, a pressure sensor can be located elsewhere within a patient. For example, the pressure sensor 62 could be included in the port housing 30. In another embodiment, shown in FIG. 28, a pressure sensor 500 can be located within a gastric band 502, such as in an inflatable portion of gastric band 502. To the extent that the gastric band 502 includes a resilient portion and a non-resilient portion, the pressure sensor 500 can be secured to either or neither of the resilient portion or non-resilient portion. In any case, the pressure sensor 500 can sense and communicate fluid pressure within the gastric band 502 before, during, and after fluid is added to or withdrawn from gastric band 502 via an injection port 501 and a catheter 503. The pressure sensor 500 can be used when a pump (not shown) or any other device is used to adjust pressure within the gastric band 502.

Figure 29:
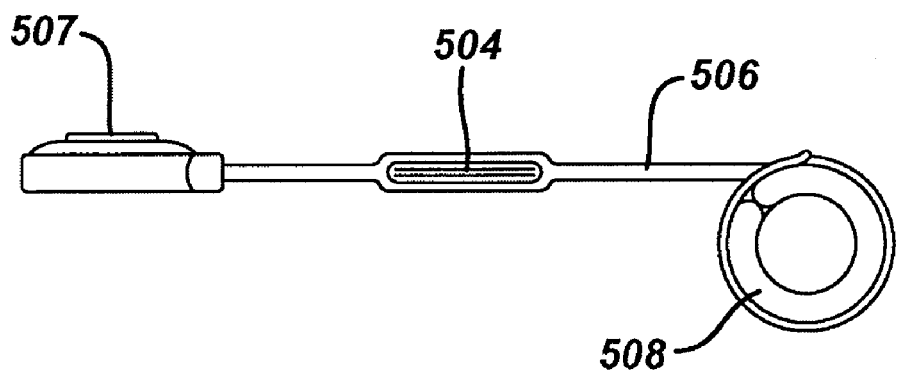
FIG. 29 is a schematic view of an embodiment of a gastric band system with a pressure sensor positioned within a catheter.
Figure 30:
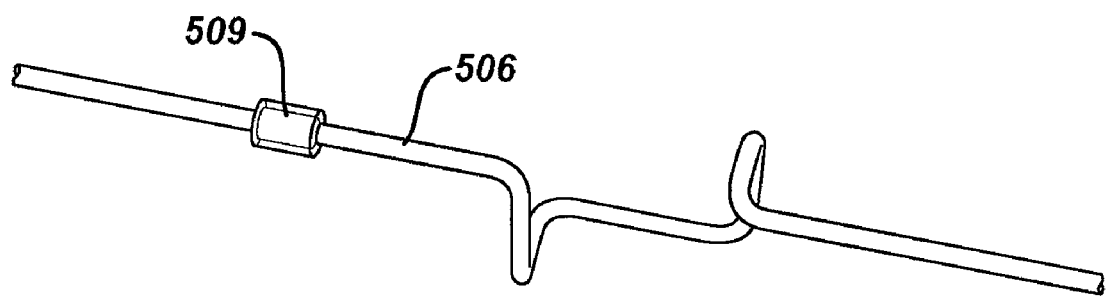
FIG. 30 is a perspective view of another embodiment of a gastric band system with a pressure sensor positioned along a catheter.

Alternatively, as shown in FIG. 29, a pressure sensor 504 can be located within a catheter 506 positioned between a gastric band 508 and a port 507, pump, reservoir, or other device in fluid communication with the catheter 506. As another variation, an example of which is shown in FIG. 30, a pressure sensor 509 can be fixedly secured in-line with a catheter 506, while not residing within catheter 506.

Figure 31:
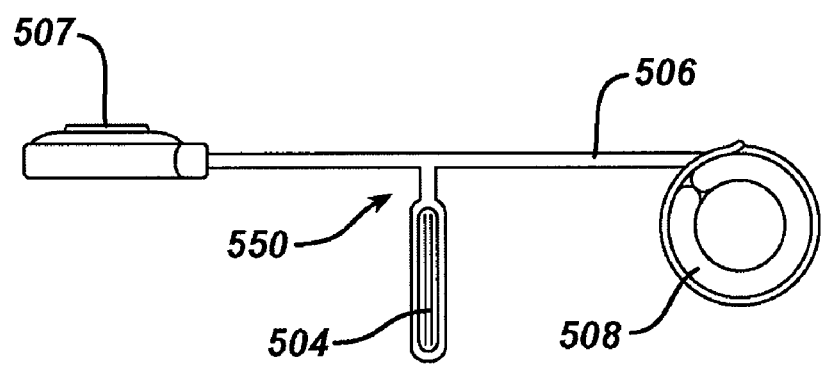
FIG. 31 is a schematic view of an embodiment of a gastric band system with a "T"-shaped pressure sensor and catheter configuration.

Yet another variation is shown in FIG. 31, which illustrates a catheter 506 having a "T"-shaped intersection 550. A pressure sensor 504 is disposed in the arm of the "T"-shaped intersection 550 that is perpendicular to the catheter 506 and is in fluid communication with the catheter 506. In one embodiment, the "T"-shaped intersection 550 is integrally formed with the catheter 506 (as shown). In another embodiment, the "T"-shaped intersection 550 is a separate component joined to the catheter 506 (e.g., using barbed connectors, etc.). Other suitable ways in which the "T"-shaped intersection 550 can be provided will be appreciated by those skilled in the art. Similarly, other ways in which a pressure sensor 504 can be provided within, in-line with, or adjacent to the catheter 506 will be appreciated by those skilled in the art.

In yet another embodiment (not depicted), a pressure sensor can be located at the interface of an injection port and a catheter, and/or at the interface of a gastric band and a catheter. Still other suitable locations for a pressure sensor will be appreciated by those skilled in the art, including but not limited to any location in or adjacent to the fluid path of a gastric band system. In addition, a pressure sensor can be positioned within (e.g., against an inner wall of) a gastric band, a catheter, and a buckle, or alternatively, a portion of such band, catheter, and buckle can include a protrusion extending outwardly therefrom to house at least a portion of the corresponding pressure sensor. Other suitable configurations for housing a pressure sensor within or adjacent to a band, catheter, or buckle will be appreciated by those skilled in the art.

In another embodiment, a plurality of pressure sensors can be used. For example, a gastric band system can include a pressure sensor within a gastric band in addition to a pressure sensor within a catheter that is in fluid communication with the gastric band. Such a plurality of pressure sensors can provide an indication of how well fluid pressure is distributed among components of a gastric band system. Such a plurality of pressure sensors can also provide greater accuracy in pressure readings, reduce the likelihood of catheter obstruction (e.g., pinching) affecting pressure reading, reduce effects of hydrostatic pressure changes from patient movement, and/or provide one or more other results. Any system that includes a plurality of pressure sensors can include a pressure sensor in a port housing and/or a pressure sensor external to the patient (e.g., a pressure sensor in a syringe or in a pressure sensor portion coupled with a syringe), in addition to any of the implanted pressure sensors described above. Furthermore, a device such as an internal or external inclinometer (or a substitute therefor) may be used to determine the angle at which the patient and/or the internal portion is oriented (e.g., standing, lying down, etc.), which may be factored into pressure data sensed by one or more sensors to account for hydrostatic pressure effects caused by a patient's orientation. Such a factor (or any other factor) may be accounted for prior to or in conjunction with the rendering of a pressure reading.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of monitoring a restriction in a patient, comprising:
   receiving a first set of data manually input by a patient, the first set of data including at least one of patient satiety level and a type of food eaten by the patient;
   correlating a first sequence of gathered pressure data values regarding a restriction device implanted in the patient to form a restriction with the first set of data to determine a baseline correlation;
   after determining the baseline correlation, receiving a second sequence of gathered pressure data values regarding the restriction device;
   comparing the baseline correlation against the second sequence of pressure data values characteristic of the patient;
   determining, if the second sequence of gathered pressure data values varies from the baseline correlation of pressure data values, a possible cause of the variation and a suggested corrective action to be performed by a user externally of the patient to address the determined possible cause of the variation;
   determining, based on the determined suggested corrective action, at least one user among a plurality of users to receive notice of the suggested corrective action; and
   providing notice of the possible cause of the variation and the suggested corrective action to the at least one user suggesting that the at least one user perform the suggested corrective action externally of the patient.

2. The method of claim 1, further comprising gathering the first sequence of pressure data values and the second sequence of pressure data values using an implantable pressure measuring device in communication with the restriction device.

3. The method of claim 1, further comprising gathering the first sequence of pressure data values and the second sequence of pressure data values using an external sensing system.

4. The method of claim 1, wherein the suggested corrective action to be performed by the user includes any one of more thoroughly chewing food, seeking medical attention, adjusting diet, and adjusting eating habits.

5. The method of claim 1, wherein providing notice of the suggested corrective action includes providing notice of the suggested corrective action to the user using a feedback mechanism immediately after determining of the suggested corrective action.

6. The method of claim 1, wherein the possible cause of the variation is any one of too much fluid disposed within the restriction device and too little fluid disposed within the restriction device.

7. The method of claim 1, wherein determining a possible cause of the variation includes determining whether the second sequence of gathered pressure data values includes pressure data values above and/or below pressure data values included in the baseline correlation.

8. The method of claim 1, wherein determining a possible cause of the variation includes determining whether a duration of the second sequence of gathered pressure data values varies from a duration of the baseline correlation.

9. The method of claim 1, wherein determining a possible cause of the variation includes determining whether a frequency of the second sequence of gathered pressure data values varies from a frequency of data values included in the baseline correlation.

10. The method of claim 1, further comprising comparing the type of food eaten by the patient with the patient's weight loss trend and determining, based on the comparing, if a corrective action should be taken.

11. The system of claim 1, wherein the user includes at least one of the patient and a physician.

12. The method of claim 1, wherein the first of data is manually inputted by the patient at regular time intervals.

13. A method of monitoring a restriction in a patient, comprising:
    determining if a pressure within an implantable restriction device configured to form a restriction in a patient measured over a period of time differs from an expected pressure over the period of time in frequency, magnitude, or duration;
    if the pressure varies from the expected pressure, determining at least one user among a plurality of users to receive notice of an alarm;
    triggering the alarm; and
    communicating the alarm to the at least one user in real time with determining if the pressure varies from the expected pressure, wherein the alarm informs the at least one user of an action for the patient to perform after receiving the alarm to address the difference between the measured pressure and the expected pressure, the action including an eating habit modification for a subsequent meal.

14. The method of claim 13, wherein triggering an alarm includes displaying on a display device a notice that the measured pressure over the period of time was determined to differ from the expected pressure over the period of time.

15. The method of claim 13, wherein the expected pressure includes historical pressure data for the implantable restriction device in the patient.

16. The method of claim 13, wherein the expected pressure includes an expected pressure for a typical patient.

17. The method of claim 13, further comprising diagnosing at least one possible cause of the difference between the measured pressure over the period of time and the expected pressure over the period of time.

18. The method of claim 17, further comprising choosing the alarm to be triggered based on at least one diagnosed possible cause.

19. A system for monitoring a restriction in a patient, comprising:
    a pressure measuring element configured to measure a pressure within an implantable restriction device configured to form a restriction in a patient;
    an input device configured to receive variable data manually input by the patient; and
    a processor configured to determine a baseline correlation between a pressure profile including two or more pressure data values measured by the pressure measuring element with the variable data collected by the input device and received by the processor;
    wherein the processor is configured to determine, if a measured correlation between the variable data input by the patient and the pressure profile varies from the baseline correlation, at least one possible cause of the difference and a possible corrective action to be performed by a user external to the patient to address the difference; and
    wherein the processor is configured to provide notice of the possible corrective action to the user suggesting that the user perform the possible corrective action externally of the patient if the measured correlation varies from the baseline correlation;
    wherein the variable data includes at least one of food type and satiety level of the patient, the food type being solid or liquid food.

20. The system of claim 19, wherein the pressure profile includes typical pressure data values for the patient over a time of day corresponding to a time of day when the pressure measuring element gathered the pressure data values included in the pressure profile.

21. The system of claim 19, wherein the pressure profile includes pressure data values for a typical patient over a time of day corresponding to a time of day when the pressure measuring element gathered the pressure data values included in the pressure profile.

22. The system of claim 19, further comprising a base unit including the processor, wherein the base unit is at a location remote from the patient.

23. The system of claim 19, further comprising an external storage mechanism including the processor, wherein the external storage mechanism is at a location local to the patient.

24. The system of claim 19, further comprising an external display device configured to provide the notice if the pressure profile differs from the baseline pressure profile.

25. The system of claim 24, wherein the display device is configured to allow the user to trigger the possible corrective action to address the difference.

26. The system of claim 19, further comprising a storage mechanism configured to store pressure data values measured by the pressure measuring element, wherein the processor is configured to retrieve stored pressure data values from the storage mechanism.

27. The system of claim 26, wherein the processor is configured to generate a pressure profile using pressure data values retrieved from the storage mechanism.

* * * * *